US008603478B2

(12) United States Patent
Whalen et al.

(10) Patent No.: US 8,603,478 B2

(45) Date of Patent: Dec. 10, 2013

(54) ANTI-RON ANTIBODIES

(75) Inventors: Kerry Whalen, Chelmsford, MA (US); Steve Bottega, Cambridge, MA (US); Andrea Boudrow, Peabody, MA (US); Lyne Breault, Roslindale, MA (US); Ting Chen, Acton, MA (US); James Gifford, Somerville, MA (US); May Han, Brookline, MA (US); Jinwei Jiang, Chestnut Hill, MA (US); Lorena Lerner, Newton Centre, MA (US); Qing Liu, Acton, MA (US); Kristan Meetze, Lexington, MA (US); Sylvie Vincent, Somerville, MA (US); Solly Weiler, Newton, MA (US); William M. Winston, Jr., Marlborough, MA (US); Jeno Gyuris, Lincoln, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 104 days.

(21) Appl. No.: 13/177,071

(22) Filed: Jul. 6, 2011

(65) Prior Publication Data

US 2012/0027773 A1 Feb. 2, 2012

Related U.S. Application Data

(60) Provisional application No. 61/361,808, filed on Jul. 6, 2010, provisional application No. 61/466,679, filed on Mar. 23, 2011.

(51) Int. Cl.
*A61K 39/395* (2006.01)

(52) U.S. Cl.
USPC .................................... 424/133.1; 424/139.1

(58) Field of Classification Search
None
See application file for complete search history.

(56) References Cited

U.S. PATENT DOCUMENTS

| | | | |
|---|---|---|---|
| 5,707,624 | A | 1/1998 | Nickoloff et al. |
| 7,235,523 | B2 | 6/2007 | Waltz et al. |
| 7,498,416 | B2 | 3/2009 | Yayon et al. |
| 2009/0136510 | A1 | 5/2009 | Pereira et al. |
| 2009/0202547 | A1 | 8/2009 | Yayon et al. |
| 2009/0226442 | A1 | 9/2009 | Huet et al. |

FOREIGN PATENT DOCUMENTS

| | | |
|---|---|---|
| WO | WO-2005/120557 | 12/2005 |
| WO | WO-2006/020258 | 2/2006 |
| WO | WO-2008/100624 | 8/2008 |
| WO | WO-2009/070294 | 6/2009 |
| WO | WO-2009/094148 | 7/2009 |
| WO | WO-2009/134776 | 11/2009 |
| WO | WO-2010/037835 | 4/2010 |
| WO | WO-2011/090761 | 7/2011 |

OTHER PUBLICATIONS

Burgess et al. (2006) "Fully Human Monoclonal Antibodies to Hepatocyte Growth Factor with Therapeutic Potential against Hepatocyte Growth Factor/c-Met-Dependent Human Tumors" Cancer Res. 66:1721-1729.

Camp et al. (2007) "Tyrosine Kinase Receptor RON in Human Pancreatic Cancer—Expression, Function, and Validation as a Target" Cancer 109:1030-1039.

Carter (2006) "Potent Antibody Therapeutics by Design" Nature Reviews. Immunology 6:343-357.

Han et al. (2010) "Anti-tumor activity of anti-RON antibodies and biomarker of response" European Journal of Cancer. Supplement. Nov. 18, 2010, Plenary Session 6. Proffered papers. Abstract 2LB.

Hayden-Ledbetter et al. (2009) "CD20-Directed Small Modular Immunopharmaceutical, TRU-015, Depletes Normal and Malignant B Cells" Clin. Cancer Res. 15:2739-2746.

Lu et al. (2007) "Multiple variants of the RON receptor tyrosine kinase: Biochemical properties, tumorigenic activities, and potential drug targets" Cancer Lett. 257:157-164.

Montero-Julian et al. (1998) "Characterization of Two Monoclonal Antibodies Against the RON Tyrosine Kinase Receptor" Hybridoma 17:541-551.

O'Toole et al. (2006) "Therapeutic Implications of a Human Neutralizing Antibody to the Macrophage-Stimulating Protein Receptor Tyrosine Kinase (RON), a c-MET Family Member" Cancer Research 66:9162-9170.

Qian et al. (2009) "Inhibition of Tumor Cell Growth, Invasion, and Metastasis by EXEL-2880 (XL880, GSK1363089), a Novel Inhibitor of HGF and VEGF Receptor Tyrosine Kinases" Cancer Res. 69:8009-8016.

Raeppel et al. (2010) "Identification of a novel series of potent RON receptor tyrosine kinase inhibitors" Bioorg Med Chem Lett 20:2745-9.

Rampino et al. (2007) "Neutralization of macrophage-stimulating protein ameliorates renal injury in anti-thy 1 glomerulonephritis" Journal of the American Society of Nephrology 18:1486-1496.

Schroeder et al. (2009) "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily" J. Med Chem. 52:1251-1254.

Secco et al. (2004) "Characterization of a single-chain intrabody directed against the human receptor tyrosine kinase Ron" Journal of Immunological Methods 285:99-109.

Wagh et al. (2008) "Met-Related Receptor Tyrosine Kinase Ron in Tumor Growth and Metastasis" Adv. Cancer Res. 100:1-33.

Wark et al. (2006) "Latest technologies for the enhancement of antibody affinity" Advanced Drug Delivery Reviews 58:657-670.

Yao et al. (2006) "Agonistic Monoclonal Antibodies Potentiate Tumorigenic and Invasive Activities of Splicing Variant of the RON Receptor Tyrosine Kinase" Cancer Biology and Therapy 5:1179-1186.

Zhang et al. (2008) "Identification of a Novel Recepteur d'Origine Nantais/c-Met Small-Molecule Kinase Inhibitor with Antitumor Activity In vivo" Cancer Res. 68:6680-6687.

(Continued)

*Primary Examiner* — Brian J Gangle
*Assistant Examiner* — Andrea McCollum
(74) *Attorney, Agent, or Firm* — Goodwin Procter LLP

(57) ABSTRACT

Monoclonal antibodies that bind and inhibit activation of human RON (Recepteur d' Origine Nantais) are disclosed. The antibodies can be used to treat certain forms of cancer that are associated with activation of RON.

14 Claims, 19 Drawing Sheets

(56) References Cited

OTHER PUBLICATIONS

Zhao et al. (2007) "Targeting CD37-positive lymphoid malignancies with a novel engineered small modular immunopharmaceutical" Blood 110:2569-2577.

Product insert for Human MSP R/Ron Antibody; Monoclonal Mouse IgG1 Clone # 99211; Catalog No. MAB691 (R&D Systems) (1 page), (2010).

International Search Report and Written Opinion, International Patent Application No. PCT/US2011/043056, mailed on Jan. 24, 2012 (27 pages).

Complete Heavy Chain Variable Region Amino Acid Alignments

| Antibody | | | CDR1 | | CDR2 | |
|---|---|---|---|---|---|---|
| 07F01 | (1) | EVKLLESGGGLVQPGGSLKLSCAASGFDFS | RHWMS | WVRLAPGKGLEWIA | EINPDSRTINYTPSLKE | KFII |
| 12B11 | (1) | EVQLVESGGGLVKPGGSLKLSCAASGFTFS | TYAMS | WIRQTPEKRLEWVA | GITNGGSFTYYPDTVKG | RFTI |
| 17F06 | (1) | EVKLVESGGGLVKPGASLKLSCAASGFIFS | SYGMS | WVRQTSDKRLEWVA | SISSGGGTTYYLDTVKG | RFTI |
| 18H09 | (1) | EVQLQESGPSLVKPSQTLSLTCYVTGDSIT | SDYWN | WIRKFPGNKLEYMG | YIS-YSGSTYYNPSLKS | RISI |
| 29B06 | (1) | EVQLQESGPSLVKPSQTLSLTCSVTGDSIT | SGYWN | WIRKFPGNKLEYMG | YIS-YSGKTYYNPSLKS | RISI |

| | | | CDR3 | | |
|---|---|---|---|---|---|
| 07F01 | (71) | SRDNAKNSLFLQMNRVRSEDTALYYCAR | RVRIHYYGAMDC | WGQGTSVTVSS | (SEQ ID NO: 2) |
| 12B11 | (71) | SRDNARNILYLQMSGLRSEDTAMYYCAR | QGYYGVNF--DY | WGQGTTLTVSS | (SEQ ID NO: 12) |
| 17F06 | (71) | SRENAKDTLYLQMSGLKSEDTALYYCTR | GQWLLKF---AY | WGQGTLVTVSA | (SEQ ID NO: 22) |
| 18H09 | (70) | TRDTSKNQFYLRLNSVTTEDTATYYCAR | THILTI----AY | WGQGTLVTVSA | (SEQ ID NO: 32) |
| 29B06 | (70) | TRDTSKNHYYLQLISVTAEDTATYYCAR | SKYDYAM---DY | WGQGTSVTVSS | (SEQ ID NO: 42) |

Fig.2

Heavy Chain CDR Amino Acid Alignments

| Antibody | CDR1 | CDR2 | CDR3 |
|---|---|---|---|
| 07F01 | RHWMS (SEQ ID NO: 5) | EINPDSRTINYTPSLKE (SEQ ID NO: 6) | RVRIHYYGAMDC (SEQ ID NO: 7) |
| 12B11 | TYAMS (SEQ ID NO: 15) | GITNGGSFTYYPDTVKG (SEQ ID NO: 16) | QGYYGVNF--DY (SEQ ID NO: 17) |
| 17F06 | SYGMS (SEQ ID NO: 25) | SISSGGGTTYYLDTVKG (SEQ ID NO: 26) | GQWLLKF---AY (SEQ ID NO: 27) |
| 18H09 | SDYWN (SEQ ID NO: 35) | YIS-YSGSTYYNPSLKS (SEQ ID NO: 36) | THILTI----AY (SEQ ID NO: 37) |
| 29B06 | SGYWN (SEQ ID NO: 45) | YIS-YSGKTYYNPSLKS (SEQ ID NO: 46) | SKYDYAM---DY (SEQ ID NO: 47) |

Fig.3

Complete Light (Kappa or Lambda) Chain Variable Region Amino Acid Alignments

```
                                                  CDR1                                  CDR2
Antibody
07F01   (1) DIVLTQSQKIVSTSTSVGARVSVTC KASQ-----NVGSSLV WYQQKPGQSPKTLIY SASFR----YS GVPDR
12B11   (1) DAVMTQTPLSLPVSLGDQASISC RSSQSLENSNGNTYLN WYLQKPGQSPQLLIY RVSNR----FS GVPDR
17F06   (1) QLVLTQSSS-ASFSLGASAKLTC TLSSQ----HTTYTIE WYQQLPLKPPKYVME LKKDGSHSTGV GIPDR
18H09   (1) QAVVTQESA-LTTSPGETVTLTC RSSAGAV--TTSNFAN WVQEKPDHLFTGLIG DTNIR----AP GVPAR
29B06   (1) DIVLTQSPASLAVSLGQRATISC RASEIVDN-FGISFMN WFQQKPGQPPKLLIY AASNQ----GS GVPAR

                                                      CDR3
07F01  (62) FTGSGSGTDFTLTISNVQSEDLADYFC QQYNNYP----LT FGAGTKLELK  (SEQ ID NO: 4)
12B11  (67) FSGSGSGTDFTLKIIRVEAEDLGLYFC LQVTHVP----HT FGGGTKLELK  (SEQ ID NO: 14)
17F06  (66) FSGSSSGADRYLTISNIQPEDEAIYIC GVGETIEDQFVYV FGGGTKVTVL  (SEQ ID NO: 24)
18H09  (64) FSGSLIGDKAALTITGAQTEDEAIYFC ALWYSNHY---WV FGGGTKLTVL  (SEQ ID NO: 34)
29B06  (66) FSGSGSGTDFSLNIHPVEEDDTAMYFC QQSKEVP----PT FGGGTKLEIK  (SEQ ID NO: 44)
```

Fig.4

Light (Kappa or Lambda) Chain CDR Amino Acid Alignments

| Antibody | CDR1 | CDR2 | CDR3 |
|---|---|---|---|
| 07F01 | KASQ-----NVGSSLV (SEQ ID NO: 8) | SASFR----YS (SEQ ID NO: 9) | QQYNNYP----LT (SEQ ID NO: 10) |
| 12B11 | RSSQSLENSNGNTYLN (SEQ ID NO: 18) | RVSNR----FS (SEQ ID NO: 19) | LQVTHVP----HT (SEQ ID NO: 20) |
| 17F06 | TLSSQ----HTTYTIE (SEQ ID NO: 28) | LKKDGSHSTGV (SEQ ID NO: 29) | GVGETIEDQFVYV (SEQ ID NO: 30) |
| 18H09 | RSSAGAV--TTSNFAN (SEQ ID NO: 38) | DTNIR----AP (SEQ ID NO: 39) | ALWYSNHY---WV (SEQ ID NO: 40) |
| 29B06 | RASEIVDN-FGISFMN (SEQ ID NO: 48) | AASNQ----GS (SEQ ID NO: 49) | QQSKEVP----PT (SEQ ID NO: 50) |

Fig.5

Complete Heavy Chain Variable Region Amino Acid Alignments

```
Antibody                                                               CDR1                       CDR2
                       07F01 EVKLLESGGGLVQPGGSLKLSCAASGFDFS RHWMS WVRLAPGKGLEWIA EINPDSRTINYTPSLKE KFII
          Chimeric 07F01 C102S EVKLLESGGGLVQPGGSLKLSCAASGFDFS RHWMS WVRLAPGKGLEWIA EINPDSRTINYTPSLKE KFII
               Sh07F01 Hv3-48 EVQLVESGGGLVQPGGSLRLSCAASGFDFS RHWMS WVRQAPGKGLEWVS EINPDSRTINYTPSLKE RFTI
Sh07F01 Hv3-48 D28T T60A L63V E65G EVQLVESGGGLVQPGGSLRLSCAASGFTFS RHWMS WVRQAPGKGLEWVS EINPDSRTINYAPSVKG RFTI

                                                                     CDR3
                       07F01 SRDNAKNSLFLQMNRVRSEDTALYYCAR RVRIHYYGAMDC WGQGTSVTVSS (SEQ ID NO: 2)
          Chimeric 07F01 C102S SRDNAKNSLFLQMNRVRSEDTALYYCAR RVRIHYYGAMDS WGQGTSVTVSS (SEQ ID NO: 133)
               Sh07F01 Hv3-48 SRDNAKNSLYLQMNSLRAEDTAVYYCAR RVRIHYYGAMDS WGQGTTVTVSS (SEQ ID NO: 135)
Sh07F01 Hv3-48 D28T T60A L63V E65G SRDNAKNSLYLQMNSLRAEDTAVYYCAR RVRIHYYGAMDS WGQGTTVTVSS (SEQ ID NO: 137)
```

Fig. 12A

```
Antibody                                                                 CDR1                        CDR2
                          29B06 EVQLQESGPSLVKPSQTLSLTCSVTGDSIT SGYWN WIRKFPGNKLEYMG YISYSGKTYYNPSLKS RISIT
                   Sh29B06_Hv4-59 QVQLQESGPGLVKPSETLSLTCTVSGGSIS SGYWN WIRQPPGKGLEWIG YISYSGKTYYNPSLKS RVTIS
                    Hu29B06 Hv4-59 QVQLQESGPGLVKPSETLSLTCTVSGDSIT SGYWN WIRKPPGKKLEYMG YISYSGKTYYNPSLKS RITIS
Hu29B06 Hv4-59 D27G T30S M48I I67V Y78F QVQLQESGPGLVKPSETLSLTCTVSGGSIS SGYWN WIRKPPGKKLEYIG YISYSGKTYYNPSLKS RVTIS

                                                                       CDR3
                          29B06 RDTSKNHYYLQLISVTAEDTATYYCAR SKYDYAMDY WGQGTSVTVSS (SEQ ID NO: 42)
                   Sh29B06_Hv4-59 VDTSKNQFSLKLSSVTAADTAVYYCAR SKYDYAMDY WGQGTLVTVSS (SEQ ID NO: 143)
                    Hu29B06 Hv4-59 RDTSKNQYSLKLSSVTAADTAVYYCAR SKYDYAMDY WGQGTLVTVSS (SEQ ID NO: 145)
Hu29B06 Hv4-59 D27G T30S M48I I67V Y78F RDTSKNQFSLKLSSVTAADTAVYYCAR SKYDYAMDY WGQGTLVTVSS (SEQ ID NO: 147)
```

Fig. 12B

Heavy Chain CDR Amino Acid Alignments

| Antibody | CDR1 | CDR2 | CDR3 |
|---|---|---|---|
| 07F01 | RHWMS (SEQ ID NO: 5) | EINPDSRTINYTPSLKE (SEQ ID NO: 6) | RVRIHYYGAMDC (SEQ ID NO: 7) |
| Chimeric 07F01 C102S | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 D28T T60A L63V E65G | RHWMS (SEQ ID NO: 5) | EINPDSRTINYAPSVKG (SEQ ID NO: 122) | RVRIHYYGAMDS (SEQ ID NO: 123) |

Fig. 13A

| Antibody | CDR1 | CDR2 | CDR3 |
|---|---|---|---|
| 29B06 | SGYWN (SEQ ID NO: 45) | YISYSGKTYYNPSLKS (SEQ ID NO: 46) | SKYDYAMDY (SEQ ID NO: 47) |
| Sh29B06_Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 D27G T30S M48I I67V Y78F | SGYWN (SEQ ID NO: 45) | YISYSGKTYYNPSLKS (SEQ ID NO: 46) | SKYDYAMDY (SEQ ID NO: 47) |

Fig. 13B

Complete Light (Kappa) Chain Variable Region Amino Acid Alignments

```
Antibody                                               CDR1                                         CDR2
          07F01 DIVLTQSQKIVSTSVGARVSVTC[KASQNVGSSLV]WYQQKPGQSPKTLIY[SASFRYS]GVPDRFTGSGSGTD
HE L 07F01 Kv1-9 DIQLTQSQSFVSTSVGDRVTVTC[RASQNVGSSLV]WYQQKPGKSPKTLIY[SASFLYS]GVPSRFSGSGSGTE
Sh07F01 Kv1-9 F1 DIQLTQSPSFLSASVGDRVTITC[RASQNVGSSLV]WYQQKPGKAPKTLIY[SASFLYS]GVPSRFSGSGSGTE

                                           CDR3
          07F01 FTLTISNVQSEDLADYFC[QQYNNYPLT]FGAGTKLELK  (SEQ ID NO: 4)
HE L 07F01 Kv1-9 FTLTISSVQPEDFADYFC[QQYNNYPLT]FGGGTKVEIK  (SEQ ID NO: 139)
Sh07F01 Kv1-9 F1 FTLTISSLQPEDFATYYC[QQYNNYPLT]FGGGTKVEIK  (SEQ ID NO: 141)
```

Fig. 14A

```
Antibody                                              CDR1                                          CDR2
         29B06 DIVLTQSPASLAVSLGQRATISC[RASEIVDNFGISFMN]WFQQKPGQPPKLLIY[AASNQGS]GVPARFSGSG
Sh29B06 Kv2-28 DIVMTQSPLSLPVTPGEPASISC[RASEIVDNFGISFMN]WYLQKPGQSPQLLIY[AASNQGS]GVPDRFSGSG

                                             CDR3
         29B06 SGTDFSLNIHPVEEDDTAMYFC[QQSKEVPPT]FGGGTKLEIK  (SEQ ID NO: 44)
Sh29B06 Kv2-28 SGTDFTLKISRVEAEDVGVYYC[QQSKEVPPT]FGGGTKVEIK  (SEQ ID NO: 149)
```

Fig. 14B

Light (Kappa) Chain CDR Amino Acid Alignments

| Antibody | CDR1 | CDR2 | CDR3 |
|---|---|---|---|
| 07F01 | KASQNVGSSLV (SEQ ID NO: 8) | SASFRYS (SEQ ID NO: 9) | QQYNNYPLT (SEQ ID NO: 10) |
| HE L 07F01 Kv1-9 | RASQNVGSSLV (SEQ ID NO: 130) | SASFLYS (SEQ ID NO: 131) | QQYNNYPLT (SEQ ID NO: 10) |
| Sh07F01 Kv1-9 F1 | RASQNVGSSLV (SEQ ID NO: 130) | SASFLYS (SEQ ID NO: 131) | QQYNNYPLT (SEQ ID NO: 10) |

Fig. 15A

| Antibody | CDR1 | CDR2 | CDR3 |
|---|---|---|---|
| 29B06 | RASEIVDNFGISFMN (SEQ ID NO: 48) | AASNQGS (SEQ ID NO: 49) | QQSKEVPPT (SEQ ID NO: 50) |
| Sh29B06 Kv2-28 | RASEIVDNFGISFMN (SEQ ID NO: 48) | AASNQGS (SEQ ID NO: 49) | QQSKEVPPT (SEQ ID NO: 50) |

Fig. 15B

SEQUENCE LISTING

```
<160> NUMBER OF SEQ ID NOS: 178

<210> SEQ ID NO 1
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gaggtgaagc ttctcgagtc tggaggtggc ctggtgcagc cgggtggatc cctgaaactc     60

tcctgtgcag cctcaggatt cgattttagt agacactgga tgagttgggt ccggctggct    120

ccagggaaag ggctagaatg gatcgcagaa attaatccag atagcagaac gataaactat    180
```

```
acgccatctc taaaggagaa attcatcatc tccagagaca acgccaaaaa ttcgctgttt    240

ctgcaaatga acagagtgag atctgaggac acagcccttt attactgtgc aagacgggta    300

agaattcatt actacggcgc tatggactgc tggggtcaag gaacctcagt caccgtctcc    360

tca                                                                  363
```

```
<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Cys Trp Gly
            100                 105                 110

Gln Gly Thr Ser Val Thr Val Ser Ser
        115                 120
```

```
<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

gacattgtgt tgacccagtc tcaaaaaatc gtgtccacat cagtaggagc cagggtcagc     60

gtcacctgca aggccagtca gaatgtgggt tctagtttag tctggtatca acagaaacca    120

ggtcaatctc ctaaaacact gatttactcg gcatccttcc ggtacagtgg agtccctgat    180

cgcttcacag gcagtggatc tgggacagat ttcactctca ccatcagcaa tgtgcagtct    240

gaagacttgg cagattattt ctgtcaacaa tataataact atccgctcac gttcggtgct    300

gggaccaagc tggagctgaa a                                              321
```

```
<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Leu Thr Gln Ser Gln Lys Ile Val Ser Thr Ser Val Gly
1               5                   10                  15
```

```
Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys
            100                 105


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg His Trp Met Ser
1               5


<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Asn Pro Asp Ser Arg Thr Ile Asn Tyr Thr Pro Ser Leu Lys
1               5                   10                  15

Glu


<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Val Arg Ile His Tyr Tyr Gly Ala Met Asp Cys
1               5                   10


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Ala Ser Gln Asn Val Gly Ser Ser Leu Val
1               5                   10


<210> SEQ ID NO 9
<211> LENGTH: 7
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Ser Ala Ser Phe Arg Tyr Ser
1               5
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Gln Gln Tyr Asn Asn Tyr Pro Leu Thr
1               5
```

<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gaggtgcagt tagtggagtc tgggggaggc ttagtgaagc ctggagggtc cctgaaactc      60

tcctgtgcag cctctggatt cactttcagt acctatgcca tgtcttggat tcgccagact     120

ccggagaaga ggctggagtg ggtcgcagga atcactaatg gtggtagttt cacctactat     180

ccagacactg tgaagggacg attcaccatc tccagagaca atgccaggaa catcctatac     240

ctgcaaatga gcggtctgag gtctgaggac acggccatgt attattgtgc aagacagggt     300

tactatggtg ttaactttga ctactggggc caaggcacca ctctcacagt ctcctca        357
```

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Ile Arg Gln Thr Pro Glu Lys Arg Leu Glu Trp Val
        35                  40                  45

Ala Gly Ile Thr Asn Gly Gly Ser Phe Thr Tyr Tyr Pro Asp Thr Val
    50                  55                  60

Lys Gly Arg Phe Thr Ile Ser Arg Asp Asn Ala Arg Asn Ile Leu Tyr
65                  70                  75                  80

Leu Gln Met Ser Gly Leu Arg Ser Glu Asp Thr Ala Met Tyr Tyr Cys
                85                  90                  95

Ala Arg Gln Gly Tyr Tyr Gly Val Asn Phe Asp Tyr Trp Gly Gln Gly
            100                 105                 110
```

```
Thr Thr Leu Thr Val Ser Ser
        115


<210> SEQ ID NO 13
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

gatgctgtga tgacccaaac tccactctcc ctgcctgtca gtcttggaga tcaagcctcc     60

atctcttgca ggtctagtca gagccttgaa aacagtaacg gaaacactta tttgaactgg    120

tacctccaga aaccaggcca gtctccacag ctcctgatct acagggtttc caaccgattt    180

tctggggtcc cagacaggtt cagtggtagt ggatcaggga cagatttcac actgaaaatc    240

atcagagtgg aggctgagga tttgggactt tatttctgcc tccaagttac acatgtcccg    300

cacacgttcg gagggggac caaactggaa ttaaaa                               336


<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ile Arg Val Glu Ala Glu Asp Leu Gly Leu Tyr Phe Cys Leu Gln Val
                85                  90                  95

Thr His Val Pro His Thr Phe Gly Gly Gly Thr Lys Leu Glu Leu Lys
            100                 105                 110


<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Tyr Ala Met Ser
1               5


<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 16

Gly Ile Thr Asn Gly Gly Ser Phe Thr Tyr Tyr Pro Asp Thr Val Lys
1 5 10 15

Gly

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Gln Gly Tyr Tyr Gly Val Asn Phe Asp Tyr
1 5 10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Ser Ser Gln Ser Leu Glu Asn Ser Asn Gly Asn Thr Tyr Leu Asn
1 5 10 15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Arg Val Ser Asn Arg Phe Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Leu Gln Val Thr His Val Pro His Thr
1 5

<210> SEQ ID NO 21
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
gaagtgaagc tggtggagtc gggggaggc ttagtgaagc ctggagcgtc tctgaaactc 60
tcctgtgcag cctctggatt cattttcagt tcctatggca tgtcttgggt tcgccagact 120
tcagacaaga ggctggagtg ggtcgcttcc attagtagtg gtggtggtac cacctactat 180

```
ctagacactg taaagggccg attcaccatc tccagagaga atgccaagga caccctgtac    240

ctgcaaatga gtggtctgaa gtctgaagac acggccttgt attactgtac aagaggccaa    300

tggttactaa agtttgctta ctggggccaa gggactctgg tcactgtctc tgca          354


<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Gly Thr Thr Tyr Tyr Leu Asp Thr Val
    50                  55                  60

Lys Gly Arg Phe Thr Ile Ser Arg Glu Asn Ala Lys Asp Thr Leu Tyr
65                  70                  75                  80

Leu Gln Met Ser Gly Leu Lys Ser Glu Asp Thr Ala Leu Tyr Tyr Cys
                85                  90                  95

Thr Arg Gly Gln Trp Leu Leu Lys Phe Ala Tyr Trp Gly Gln Gly Thr
            100                 105                 110

Leu Val Thr Val Ser Ala
        115


<210> SEQ ID NO 23
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

caacttgtgc tcactcagtc atcttcagcc tctttctccc tgggagcctc agcaaaactc     60

acgtgcacct tgagtagtca gcacactacg tacaccattg aatggtatca gcaactgcca    120

ctcaagcctc ctaagtatgt gatggagctt aagaaagatg gaagccacag cacaggtgtt    180

gggattcctg atcgcttctc tggatccagc tctggtgctg atcgctacct taccatttcc    240

aacatccagc ctgaagatga agcaatatac atctgtggtg tgggtgagac aattgaggac    300

caatttgtgt atgttttcgg cggtggcacc aaggtcactg tccta                    345


<210> SEQ ID NO 24
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Thr Thr Tyr Thr
```

```
            20                  25                  30

Ile Glu Trp Tyr Gln Gln Leu Pro Leu Lys Pro Pro Lys Tyr Val Met
        35                  40                  45

Glu Leu Lys Lys Asp Gly Ser His Ser Thr Gly Val Gly Ile Pro Asp
    50                  55                  60

Arg Phe Ser Gly Ser Ser Ser Gly Ala Asp Arg Tyr Leu Thr Ile Ser
65                  70                  75                  80

Asn Ile Gln Pro Glu Asp Glu Ala Ile Tyr Ile Cys Gly Val Gly Glu
                85                  90                  95

Thr Ile Glu Asp Gln Phe Val Tyr Val Phe Gly Gly Gly Thr Lys Val
            100                 105                 110

Thr Val Leu
        115
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Ser Tyr Gly Met Ser
1               5
```

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

```
Ser Ile Ser Ser Gly Gly Gly Thr Thr Tyr Tyr Leu Asp Thr Val Lys
1               5                   10                  15

Gly
```

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

```
Gly Gln Trp Leu Leu Lys Phe Ala Tyr
1               5
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

```
Thr Leu Ser Ser Gln His Thr Thr Tyr Thr Ile Glu
1               5                   10
```

<210> SEQ ID NO 29

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Lys Lys Asp Gly Ser His Ser Thr Gly Val
1               5                   10


<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Gly Glu Thr Ile Glu Asp Gln Phe Val Tyr Val
1               5                   10


<210> SEQ ID NO 31
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

gaggtgcagc ttcaggagtc aggacctagc ctcgtgaaac cttctcagac tctgtccctc      60

acctgttatg tcactggcga ctccatcacc agtgattact ggaattggat ccggaaattc     120

ccaggaaata aacttgagta catgggatat atcagctaca gtggtagcac ttactacaat     180

ccatctctca aaagtcgaat ctccatcact cgagacacat ccaagaacca gttctacctt     240

cggttgaatt ctgtgactac tgaggacaca gccacatatt actgtgcaag aacccatata     300

cttacgattg cttactgggg ccaagggact ctggtcactg tctctgca                  348


<210> SEQ ID NO 32
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Gln Glu Ser Gly Pro Ser Leu Val Lys Pro Ser Gln
1               5                   10                  15

Thr Leu Ser Leu Thr Cys Tyr Val Thr Gly Asp Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Phe Tyr Leu
65                  70                  75                  80

Arg Leu Asn Ser Val Thr Thr Glu Asp Thr Ala Thr Tyr Tyr Cys Ala
                85                  90                  95

Arg Thr His Ile Leu Thr Ile Ala Tyr Trp Gly Gln Gly Thr Leu Val
            100                 105                 110
```

```
Thr Val Ser Ala
        115


<210> SEQ ID NO 33
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

caggctgttg tgactcagga atctgcactc accacatcac ctggtgaaac agtcacactc     60

acttgtcgct caagtgccgg ggctgttaca actagtaact ttgccaactg ggtccaagaa    120

aaaccagatc atttattcac tggtctaata ggtgatacca acatccgagc tccaggtgtt    180

cctgccagat tctcaggctc cctgattgga gacaaggctg ccctcaccat cacaggggca    240

cagactgagg atgaggcaat atatttctgt gctctttggt acagcaacca ttactgggtg    300

ttcggtggag gaaccaaact gactgtccta                                     330


<210> SEQ ID NO 34
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Phe Ala Asn Trp Val Gln Glu Lys Pro Asp His Leu Phe Thr Gly
        35                  40                  45

Leu Ile Gly Asp Thr Asn Ile Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Tyr Trp Val Phe Gly Gly Gly Thr Lys Leu Thr Val Leu
            100                 105                 110


<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Asp Tyr Trp Asn
1               5


<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 36

```
Tyr Ile Ser Tyr Ser Gly Ser Thr Tyr Tyr Asn Pro Ser Leu Lys Ser
1               5                   10                  15
```

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

```
Thr His Ile Leu Thr Ile Ala Tyr
1               5
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Arg Ser Ser Ala Gly Ala Val Thr Thr Ser Asn Phe Ala Asn
1               5                   10
```

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Asp Thr Asn Ile Arg Ala Pro
1               5
```

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

```
Ala Leu Trp Tyr Ser Asn His Tyr Trp Val
1               5                   10
```

<210> SEQ ID NO 41
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
gaggtgcagc ttcaggagtc aggacctagc ctcgtgaaac cttctcagac tctgtccctc     60

acctgttctg tcactggcga ctccatcacc agtggttact ggaactggat ccggaaattc    120

ccagggaata aacttgagta catggggtac ataagctaca gtggtaaaac ttactacaat    180
```

```
ccatctctca aaagtcgaat ctccatcact cgagacacat ccaagaacca ttactacctg    240

cagttgattt ctgtgactgc tgaggacaca gccacatatt actgtgcaag gtctaagtac    300

gactatgcta tggactactg gggtcaagga acctcagtca ccgtctcctc a             351


<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
            100                 105                 110

Val Thr Val Ser Ser
        115


<210> SEQ ID NO 43
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

gacattgtgc tgacccaatc tccagcttct ttggctgtgt ctctaggaca gagggccacc     60

atctcctgca gagccagcga aattgttgat aattttggca ttagttttat gaactggttc    120

caacagaaac caggacagcc acccaaactc ctcatctatg ctgcatccaa ccaaggatcc    180

ggggtccctg ccaggtttag tggcagtggg tctgggacag acttcagcct caacatccat    240

cctgtggagg aggatgatac tgcaatgtat ttctgtcagc aaagtaagga ggttcctccg    300

acgttcggtg gaggcaccaa gctggaaatc aaa                                 333


<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ile Val Asp Asn Phe
            20                  25                  30
```

```
Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys
            100                 105                 110


<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Tyr Trp Asn
1               5


<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Ile Ser Tyr Ser Gly Lys Thr Tyr Tyr Asn Pro Ser Leu Lys Ser
1               5                   10                  15


<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Lys Tyr Asp Tyr Ala Met Asp Tyr
1               5


<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Glu Ile Val Asp Asn Phe Gly Ile Ser Phe Met Asn
1               5                   10                  15


<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 49

Ala Ala Ser Asn Gln Gly Ser
1 5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Gln Ser Lys Glu Val Pro Pro Thr
1 5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Phe Asp Phe Ser Arg His
1 5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Asn Pro Asp Ser Arg Thr
1 5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gly Phe Thr Phe Ser Thr Tyr
1 5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Thr Asn Gly Gly Ser Phe
1 5

<210> SEQ ID NO 55
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 55

Gly Phe Ile Phe Ser Ser Tyr
1 5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Ser Ser Gly Gly Gly Thr
1 5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Asp Ser Ile Thr Ser Asp
1 5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ser Tyr Ser Gly Ser
1 5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Asp Ser Ile Thr Ser Gly
1 5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Ser Tyr Ser Gly Lys
1 5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Phe Asp Phe Ser Arg His Trp
1 5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Ile Asn Pro Asp Ser Arg Thr Ile
1 5

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Ala Arg Arg Val Arg Ile His Tyr Tyr Gly Ala Met Asp Cys
1 5 10

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Phe Thr Phe Ser Thr Tyr Ala
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Ile Thr Asn Gly Gly Ser Phe Thr
1 5

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

```
Ala Arg Gln Gly Tyr Tyr Gly Val Asn Phe Asp Tyr
1               5                   10


<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Ile Phe Ser Ser Tyr Gly
1               5


<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Ser Ser Gly Gly Gly Thr Thr
1               5


<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Arg Gly Gln Trp Leu Leu Lys Phe Ala Tyr
1               5                   10


<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Asp Ser Ile Thr Ser Asp Tyr
1               5


<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Ser Tyr Ser Gly Ser Thr
1               5


<210> SEQ ID NO 72
<211> LENGTH: 10
<212> TYPE: PRT
<213> ORGANISM: Artificial Sequence
<220> FEATURE:
```

<223> OTHER INFORMATION: Description of Artificial Sequence: Synthetic peptide

<400> SEQUENCE: 72

Ala Arg Thr His Ile Leu Thr Ile Ala Tyr
1 5 10

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gly Asp Ser Ile Thr Ser Gly Tyr
1 5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Ile Ser Tyr Ser Gly Lys Thr
1 5

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ala Arg Ser Lys Tyr Asp Tyr Ala Met Asp Tyr
1 5 10

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Gln Asn Val Gly Ser Ser
1 5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Gln Ser Leu Glu Asn Ser Asn Gly Asn Thr Tyr
1 5 10

<210> SEQ ID NO 78

<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Ser Gln His Thr Thr Tyr Thr
1 5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Leu Lys Lys Asp Gly Ser His
1 5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Ala Gly Ala Val Thr Thr Ser Asn Phe
1 5

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Glu Ile Val Asp Asn Phe Gly Ile Ser Phe
1 5 10

<210> SEQ ID NO 82
<211> LENGTH: 972
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82
gccaaaacga cacccccatc tgtctatcca ctggcccctg gatctgctgc ccaaactaac 60
tccatggtga ccctgggatg cctggtcaag ggctatttcc ctgagccagt gacagtgacc 120
tggaactctg gatccctgtc cagcggtgtg cacaccttcc cagctgtcct gcagtctgac 180
ctctacactc tgagcagctc agtgactgtc ccctccagca cctggcccag cgagaccgtc 240
acctgcaacg ttgcccaccc ggccagcagc accaaggtgg acaagaaaat tgtgcccagg 300
gattgtggtt gtaagccttg catatgtaca gtcccagaag tatcatctgt cttcatcttc 360
cccccaaagc ccaaggatgt gctcaccatt actctgactc ctaaggtcac gtgtgttgtg 420
gtagacatca gcaaggatga tcccgaggtc cagttcagct ggtttgtaga tgatgtggag 480

```
gtgcacacag ctcagacgca accccgggag gagcagttca acagcacttt ccgctcagtc    540

agtgaacttc ccatcatgca ccaggactgg ctcaatggca aggagttcaa atgcagggtc    600

aacagtgcag ctttccctgc ccccatcgag aaaaccatct ccaaaaccaa aggcagaccg    660

aaggctccac aggtgtacac cattccacct cccaaggagc agatggccaa ggataaagtc    720

agtctgacct gcatgataac agacttcttc cctgaagaca ttactgtgga gtggcagtgg    780

aatgggcagc cagcggagaa ctacaagaac actcagccca tcatggacac agatggctct    840

tacttcgtct acagcaagct caatgtgcag aagagcaact gggaggcagg aaatactttc    900

acctgctctg tgttacatga gggcctgcac aaccaccata ctgagaagag cctctcccac    960

tctcctggta aa                                                        972
```

```
<210> SEQ ID NO 83
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270
```

```
Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 84
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
gccaaaacaa cagccccatc ggtctatcca ctggcccctg tgtgtggaga tacaactggc     60
tcctcggtga ctctaggatg cctggtcaag ggttatttcc ctgagccagt gaccttgacc    120
tggaactctg gatccctgtc cagtggtgtg cacaccttcc cagctgtcct gcagtctgac    180
ctctacaccc tcagcagctc agtgactgta acctcgagca cctggcccag ccagtccatc    240
acctgcaatg tggcccaccc ggcaagcagc accaaggtgg acaagaaaat tgagcccaga    300
gggcccacaa tcaagccctg tcctccatgc aaatgcccag cacctaacct cttgggtgga    360
ccatccgtct tcatcttccc tccaaagatc aaggatgtac tcatgatctc cctgagcccc    420
atagtcacat gtgtggtggt ggatgtgagc gaggatgacc cagatgtcca gatcagctgg    480
tttgtgaaca acgtggaagt acacacagct cagacacaaa cccatagaga ggattacaac    540
agtactctcc gggtggtcag tgccctcccc atccagcacc aggactggat gagtggcaag    600
gagttcaaat gcaaggtcaa caacaaagac ctcccagcgc ccatcgagag aaccatctca    660
aaacccaaag ggtcagtaag agctccacag gtatatgtct tgcctccacc agaagaagag    720
atgactaaga aacaggtcac tctgacctgc atggtcacag acttcatgcc tgaagacatt    780
tacgtggagt ggaccaacaa cgggaaaaca gagctaaact acaagaacac tgaaccagtc    840
ctggactctg atggttctta cttcatgtac agcaagctga gagtggaaaa gaagaactgg    900
gtggaaagaa atagctactc ctgttcagtg gtccacgagg gtctgcacaa tcaccacacg    960
actaagagct tctcccggac tccgggtaaa                                     990
```

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60
```

```
Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 86
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
cgggctgatg ctgcaccaac tgtatccatc ttcccaccat ccagtgagca gttaacatct     60

ggaggtgcct cagtcgtgtg cttcttgaac aacttctacc ccaaagacat caatgtcaag    120

tggaagattg atggcagtga acgacaaaat ggcgtcctga acagttggac tgatcaggac    180

agcaaagaca gcacctacag catgagcagc accctcacgt tgaccaagga cgagtatgaa    240

cgacataaca gctatacctg tgaggccact cacaagacat caacttcacc cattgtcaag    300

agcttcaaca ggaatgagtg t                                              321
```

<210> SEQ ID NO 87
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 87

```
Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

<210> SEQ ID NO 88
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
ggccagccca agtcttcgcc atcagtcacc ctgtttccac cttcctctga agagctcgag     60

actaacaagg ccacactggt gtgtacgatc actgatttct acccaggtgt ggtgacagtg    120

gactggaagg tagatggtac ccctgtcact cagggtatgg agacaaccca gccttccaaa    180

cagagcaaca acaagtacat ggctagcagc tacctgaccc tgacagcaag agcatgggaa    240

aggcatagca gttacagctg ccaggtcact catgaaggtc acactgtgga gaagagtttg    300

tcccgtgctg actgttcc                                                  318
```

<210> SEQ ID NO 89
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105
```

<210> SEQ ID NO 90
<211> LENGTH: 315
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90
ggtcagccca agtccactcc cactctcacc gtgtttccac cttcctctga ggagctcaag 60
gaaaacaaag ccacactggt gtgtctgatt tccaactttt ccccgagtgg tgtgacagtg 120
gcctggaagg caaatggtac acctatcacc cagggtgtgg acacttcaaa tcccaccaaa 180
gagggcaaca agttcatggc cagcagcttc ctacatttga catcggacca gtggagatct 240
cacaacagtt ttacctgtca agttacacat gaaggggaca ctgtggagaa gagtctgtct 300
cctgcagaat gtctc 315

<210> SEQ ID NO 91
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Gly Gln Pro Lys Ser Thr Pro Thr Leu Thr Val Phe Pro Pro Ser Ser
1 5 10 15

Glu Glu Leu Lys Glu Asn Lys Ala Thr Leu Val Cys Leu Ile Ser Asn
20 25 30

Phe Ser Pro Ser Gly Val Thr Val Ala Trp Lys Ala Asn Gly Thr Pro
35 40 45

Ile Thr Gln Gly Val Asp Thr Ser Asn Pro Thr Lys Glu Gly Asn Lys
50 55 60

Phe Met Ala Ser Ser Phe Leu His Leu Thr Ser Asp Gln Trp Arg Ser
65 70 75 80

His Asn Ser Phe Thr Cys Gln Val Thr His Glu Gly Asp Thr Val Glu
85 90 95

Lys Ser Leu Ser Pro Ala Glu Cys Leu
100 105

<210> SEQ ID NO 92
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 92
gaggtgaagc ttctcgagtc tggaggtggc ctggtgcagc cgggtggatc cctgaaactc 60
tcctgtgcag cctcaggatt cgattttagt agacactgga tgagttgggt ccggctggct 120
ccagggaaag ggctagaatg gatcgcagaa attaatccag atagcagaac gataaactat 180
acgccatctc taaaggagaa attcatcatc tccagagaca acgccaaaaa ttcgctgttt 240
ctgcaaatga acagagtgag atctgaggac acagcccttt attactgtgc aagacgggta 300
agaattcatt actacggcgc tatggactgc tggggtcaag gaacctcagt caccgtctcc 360
tcagccaaaa cgacaccccc atctgtctat ccactggccc ctggatctgc tgcccaaact 420

```
aactccatgg tgaccctggg atgcctggtc aagggctatt tccctgagcc agtgacagtg    480

acctggaact ctggatccct gtccagcggt gtgcacacct tcccagctgt cctgcagtct    540

gacctctaca ctctgagcag ctcagtgact gtcccctcca gcacctggcc cagcgagacc    600

gtcacctgca acgttgccca cccggccagc agcaccaagg tggacaagaa aattgtgccc    660

agggattgtg gttgtaagcc ttgcatatgt acagtcccag aagtatcatc tgtcttcatc    720

ttccccccaa agcccaagga tgtgctcacc attactctga ctcctaaggt cacgtgtgtt    780

gtggtagaca tcagcaagga tgatcccgag gtccagttca gctggtttgt agatgatgtg    840

gaggtgcaca cagctcagac gcaaccccgg gaggagcagt tcaacagcac tttccgctca    900

gtcagtgaac ttcccatcat gcaccaggac tggctcaatg gcaaggagtt caaatgcagg    960

gtcaacagtg cagctttccc tgcccccatc gagaaaacca tctccaaaac caaaggcaga   1020

ccgaaggctc cacaggtgta caccattcca cctcccaagg agcagatggc caaggataaa   1080

gtcagtctga cctgcatgat aacagacttc ttccctgaag acattactgt ggagtggcag   1140

tggaatgggc agccagcgga gaactacaag aacactcagc ccatcatgga cacagatggc   1200

tcttacttcg tctacagcaa gctcaatgtg cagaagagca actgggaggc aggaaatact   1260

ttcacctgct ctgtgttaca tgagggcctg cacaaccacc atactgagaa gagcctctcc   1320

cactctcctg gtaaa                                                    1335
```

```
<210> SEQ ID NO 93
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Cys Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190
```

```
Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445


<210> SEQ ID NO 94
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

gacattgtgt tgacccagtc tcaaaaaatc gtgtccacat cagtaggagc cagggtcagc     60

gtcacctgca aggccagtca gaatgtgggt tctagtttag tctggtatca acagaaacca    120

ggtcaatctc ctaaaacact gatttactcg gcatccttcc ggtacagtgg agtccctgat    180

cgcttcacag gcagtggatc tgggacagat ttcactctca ccatcagcaa tgtgcagtct    240

gaagacttgg cagattattt ctgtcaacaa tataataact atccgctcac gttcggtgct    300

gggaccaagc tggagctgaa acgggctgat gctgcaccaa ctgtatccat cttcccacca    360

tccagtgagc agttaacatc tggaggtgcc tcagtcgtgt gcttcttgaa caacttctac    420

cccaaagaca tcaatgtcaa gtggaagatt gatggcagtg aacgacaaaa tggcgtcctg    480

aacagttgga ctgatcagga cagcaaagac agcacctaca gcatgagcag caccctcacg    540

ttgaccaagg acgagtatga acgacataac agctatacct gtgaggccac tcacaagaca    600

tcaacttcac ccattgtcaa gagcttcaac aggaatgagt gt                       642
```

<210> SEQ ID NO 95
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Asp Ile Val Leu Thr Gln Ser Gln Lys Ile Val Ser Thr Ser Val Gly
1               5                   10                  15

Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 96
<211> LENGTH: 1329
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
gaggtgcagt tagtggagtc tgggggaggc ttagtgaagc ctggagggtc cctgaaactc     60

tcctgtgcag cctctggatt cactttcagt acctatgcca tgtcttggat tcgccagact    120

ccggagaaga ggctggagtg ggtcgcagga atcactaatg gtggtagttt cacctactat    180

ccagacactg tgaagggacg attcaccatc tccagagaca atgccaggaa catcctatac    240

ctgcaaatga gcggtctgag gtctgaggac acggccatgt attattgtgc aagacagggt    300

tactatggtg ttaactttga ctactggggc caaggcacca ctctcacagt ctcctcagcc    360

aaaacgacac ccccatctgt ctatccactg gcccctggat ctgctgccca aactaactcc    420

atggtgaccc tgggatgcct ggtcaagggc tatttccctg agccagtgac agtgacctgg    480
```

```
aactctggat ccctgtccag cggtgtgcac accttcccag ctgtcctgca gtctgacctc    540

tacactctga gcagctcagt gactgtcccc tccagcacct ggcccagcga gaccgtcacc    600

tgcaacgttg cccacccggc cagcagcacc aaggtggaca agaaaattgt gcccagggat    660

tgtggttgta agccttgcat atgtacagtc ccagaagtat catctgtctt catcttcccc    720

ccaaagccca aggatgtgct caccattact ctgactccta aggtcacgtg tgttgtggta    780

gacatcagca aggatgatcc cgaggtccag ttcagctggt ttgtagatga tgtggaggtg    840

cacacagctc agacgcaacc ccgggaggag cagttcaaca gcactttccg ctcagtcagt    900

gaacttccca tcatgcacca ggactggctc aatggcaagg agttcaaatg cagggtcaac    960

agtgcagctt tccctgcccc catcgagaaa accatctcca aaaccaaagg cagaccgaag   1020

gctccacagg tgtacaccat tccacctccc aaggagcaga tggccaagga taaagtcagt   1080

ctgacctgca tgataacaga cttcttccct gaagacatta ctgtggagtg gcagtggaat   1140

gggcagccag cggagaacta caagaacact cagcccatca tggacacaga tggctcttac   1200

ttcgtctaca gcaagctcaa tgtgcagaag agcaactggg aggcaggaaa tactttcacc   1260

tgctctgtgt tacatgaggg cctgcacaac caccatactg agaagagcct ctcccactct   1320

cctggtaaa                                                           1329
```

```
<210> SEQ ID NO 97
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Ile Arg Gln Thr Pro Glu Lys Arg Leu Glu Trp Val
        35                  40                  45

Ala Gly Ile Thr Asn Gly Gly Ser Phe Thr Tyr Tyr Pro Asp Thr Val
    50                  55                  60

Lys Gly Arg Phe Thr Ile Ser Arg Asp Asn Ala Arg Asn Ile Leu Tyr
65                  70                  75                  80

Leu Gln Met Ser Gly Leu Arg Ser Glu Asp Thr Ala Met Tyr Tyr Cys
                85                  90                  95

Ala Arg Gln Gly Tyr Tyr Gly Val Asn Phe Asp Tyr Trp Gly Gln Gly
            100                 105                 110

Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205
```

```
Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 98
<211> LENGTH: 657
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
gatgctgtga tgacccaaac tccactctcc ctgcctgtca gtcttggaga tcaagcctcc     60

atctcttgca ggtctagtca gagccttgaa aacagtaacg gaaacactta tttgaactgg    120

tacctccaga aaccaggcca gtctccacag ctcctgatct acagggtttc caaccgattt    180

tctggggtcc cagacaggtt cagtggtagt ggatcaggga cagatttcac actgaaaatc    240

atcagagtgg aggctgagga tttgggactt tatttctgcc tccaagttac acatgtcccg    300

cacacgttcg gaggggggac caaactggaa ttaaaacggg ctgatgctgc accaactgta    360

tccatcttcc caccatccag tgagcagtta acatctggag gtgcctcagt cgtgtgcttc    420

ttgaacaact tctaccccaa agacatcaat gtcaagtgga agattgatgg cagtgaacga    480

caaaatggcg tcctgaacag ttggactgat caggacagca aagacagcac ctacagcatg    540

agcagcaccc tcacgttgac caaggacgag tatgaacgac ataacagcta tacctgtgag    600

gccactcaca agacatcaac ttcacccatt gtcaagagct tcaacaggaa tgagtgt       657
```

<210> SEQ ID NO 99
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ile Arg Val Glu Ala Glu Asp Leu Gly Leu Tyr Phe Cys Leu Gln Val
                85                  90                  95

Thr His Val Pro His Thr Phe Gly Gly Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 100
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
gaagtgaagc tggtggagtc gggggaggc ttagtgaagc ctggagcgtc tctgaaactc      60

tcctgtgcag cctctggatt cattttcagt tcctatggca tgtcttgggt tcgccagact     120

tcagacaaga ggctggagtg ggtcgcttcc attagtagtg gtggtggtac cacctactat     180

ctagacactg taaagggccg attcaccatc tccagagaga atgccaagga caccctgtac     240

ctgcaaatga gtggtctgaa gtctgaagac acggccttgt attactgtac aagaggccaa     300

tggttactaa agtttgctta ctggggccaa gggactctgg tcactgtctc tgcagccaaa     360

acaacagccc catcggtcta tccactggcc cctgtgtgtg gagatacaac tggctcctcg     420

gtgactctag gatgcctggt caagggttat ttccctgagc cagtgacctt gacctggaac     480

tctggatccc tgtccagtgg tgtgcacacc ttcccagctg tcctgcagtc tgacctctac     540
```

```
accctcagca gctcagtgac tgtaacctcg agcacctggc ccagccagtc catcacctgc    600

aatgtggccc acccggcaag cagcaccaag gtggacaaga aaattgagcc cagagggccc    660

acaatcaagc cctgtcctcc atgcaaatgc ccagcaccta acctcttggg tggaccatcc    720

gtcttcatct tccctccaaa gatcaaggat gtactcatga tctccctgag ccccatagtc    780

acatgtgtgg tggtggatgt gagcgaggat gacccagatg tccagatcag ctggtttgtg    840

aacaacgtgg aagtacacac agctcagaca caaacccata gagaggatta caacagtact    900

ctccgggtgg tcagtgccct ccccatccag caccaggact ggatgagtgg caaggagttc    960

aaatgcaagg tcaacaacaa agacctccca gcgcccatcg agagaaccat ctcaaaaccc   1020

aaagggtcag taagagctcc acaggtatat gtcttgcctc caccagaaga agagatgact   1080

aagaaacagg tcactctgac ctgcatggtc acagacttca tgcctgaaga catttacgtg   1140

gagtggacca acaacgggaa aacagagcta aactacaaga acactgaacc agtcctggac   1200

tctgatggtt cttacttcat gtacagcaag ctgagagtgg aaaagaagaa ctgggtggaa   1260

agaaatagct actcctgttc agtggtccac gagggtctgc acaatcacca cacgactaag   1320

agcttctccc ggactccggg taaa                                          1344
```

```
<210> SEQ ID NO 101
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Gly Thr Thr Tyr Tyr Leu Asp Thr Val
    50                  55                  60

Lys Gly Arg Phe Thr Ile Ser Arg Glu Asn Ala Lys Asp Thr Leu Tyr
65                  70                  75                  80

Leu Gln Met Ser Gly Leu Lys Ser Glu Asp Thr Ala Leu Tyr Tyr Cys
                85                  90                  95

Thr Arg Gly Gln Trp Leu Leu Lys Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
```

```
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly Lys
        435                 440                 445
```

<210> SEQ ID NO 102
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
caacttgtgc tcactcagtc atcttcagcc tctttctccc tgggagcctc agcaaaactc     60

acgtgcacct tgagtagtca gcacactacg tacaccattg aatggtatca gcaactgcca    120

ctcaagcctc ctaagtatgt gatggagctt aagaaagatg gaagccacag cacaggtgtt    180

gggattcctg atcgcttctc tggatccagc tctggtgctg atcgctacct taccatttcc    240

aacatccagc ctgaagatga agcaatatac atctgtggtg tgggtgagac aattgaggac    300

caatttgtgt atgttttcgg cggtggcacc aaggtcactg tcctaggtca gcccaagtcc    360

actcccactc tcaccgtgtt tccaccttcc tctgaggagc tcaaggaaaa caaagccaca    420

ctggtgtgtc tgatttccaa cttttccccg agtggtgtga cagtggcctg gaaggcaaat    480

ggtacaccta tcacccaggg tgtggacact tcaaatccca ccaaagaggg caacaagttc    540

atggccagca gcttcctaca tttgacatcg gaccagtgga gatctcacaa cagttttacc    600

tgtcaagtta cacatgaagg ggacactgtg gagaagagtc tgtctcctgc agaatgtctc    660
```

<210> SEQ ID NO 103
<211> LENGTH: 220

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Thr Thr Tyr Thr
            20                  25                  30

Ile Glu Trp Tyr Gln Gln Leu Pro Leu Lys Pro Pro Lys Tyr Val Met
        35                  40                  45

Glu Leu Lys Lys Asp Gly Ser His Ser Thr Gly Val Gly Ile Pro Asp
    50                  55                  60

Arg Phe Ser Gly Ser Ser Ser Gly Ala Asp Arg Tyr Leu Thr Ile Ser
65                  70                  75                  80

Asn Ile Gln Pro Glu Asp Glu Ala Ile Tyr Ile Cys Gly Val Gly Glu
                85                  90                  95

Thr Ile Glu Asp Gln Phe Val Tyr Val Phe Gly Gly Gly Thr Lys Val
            100                 105                 110

Thr Val Leu Gly Gln Pro Lys Ser Thr Pro Thr Leu Thr Val Phe Pro
        115                 120                 125

Pro Ser Ser Glu Glu Leu Lys Glu Asn Lys Ala Thr Leu Val Cys Leu
    130                 135                 140

Ile Ser Asn Phe Ser Pro Ser Gly Val Thr Val Ala Trp Lys Ala Asn
145                 150                 155                 160

Gly Thr Pro Ile Thr Gln Gly Val Asp Thr Ser Asn Pro Thr Lys Glu
                165                 170                 175

Gly Asn Lys Phe Met Ala Ser Ser Phe Leu His Leu Thr Ser Asp Gln
            180                 185                 190

Trp Arg Ser His Asn Ser Phe Thr Cys Gln Val Thr His Glu Gly Asp
        195                 200                 205

Thr Val Glu Lys Ser Leu Ser Pro Ala Glu Cys Leu
    210                 215                 220


<210> SEQ ID NO 104
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

gaggtgcagc ttcaggagtc aggacctagc ctcgtgaaac cttctcagac tctgtccctc     60

acctgttatg tcactggcga ctccatcacc agtgattact ggaattggat ccggaaattc    120

ccaggaaata aacttgagta catgggatat atcagctaca gtggtagcac ttactacaat    180

ccatctctca aaagtcgaat ctccatcact cgagacacat ccaagaacca gttctacctt    240

cggttgaatt ctgtgactac tgaggacaca gccacatatt actgtgcaag aacccatata    300

cttacgattg cttactgggg ccaagggact ctggtcactg tctctgcagc caaaacgaca    360

cccccatctg tctatccact ggcccctgga tctgctgccc aaactaactc catggtgacc    420

ctgggatgcc tggtcaaggg ctatttccct gagccagtga cagtgacctg gaactctgga    480

tccctgtcca gcggtgtgca caccttccca gctgtcctgc agtctgacct ctacactctg    540

agcagctcag tgactgtccc ctccagcacc tggcccagcg agaccgtcac ctgcaacgtt    600
```

```
gcccacccgg ccagcagcac caaggtggac aagaaaattg tgcccaggga ttgtggttgt    660

aagccttgca tatgtacagt cccagaagta tcatctgtct tcatcttccc cccaaagccc    720

aaggatgtgc tcaccattac tctgactcct aaggtcacgt gtgttgtggt agacatcagc    780

aaggatgatc ccgaggtcca gttcagctgg tttgtagatg atgtggaggt gcacacagct    840

cagacgcaac ccgggagga gcagttcaac agcactttcc gctcagtcag tgaacttccc    900

atcatgcacc aggactggct caatggcaag gagttcaaat gcagggtcaa cagtgcagct    960

ttccctgccc ccatcgagaa aaccatctcc aaaaccaaag gcagaccgaa ggctccacag   1020

gtgtacacca ttccacctcc caaggagcag atggccaagg ataaagtcag tctgacctgc   1080

atgataacag acttcttccc tgaagacatt actgtggagt ggcagtggaa tgggcagcca   1140

gcggagaact acaagaacac tcagcccatc atggacacag atggctctta cttcgtctac   1200

agcaagctca atgtgcagaa gagcaactgg gaggcaggaa atactttcac ctgctctgtg   1260

ttacatgagg gcctgcacaa ccaccatact gagaagagcc tctcccactc tcctggtaaa   1320


<210> SEQ ID NO 105
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Gln Glu Ser Gly Pro Ser Leu Val Lys Pro Ser Gln
1               5                   10                  15

Thr Leu Ser Leu Thr Cys Tyr Val Thr Gly Asp Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Phe Tyr Leu
65                  70                  75                  80

Arg Leu Asn Ser Val Thr Thr Glu Asp Thr Ala Thr Tyr Tyr Cys Ala
                85                  90                  95

Arg Thr His Ile Leu Thr Ile Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240
```

```
Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 106
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

caggctgttg tgactcagga atctgcactc accacatcac ctggtgaaac agtcacactc      60

acttgtcgct caagtgccgg ggctgttaca actagtaact ttgccaactg ggtccaagaa     120

aaaccagatc atttattcac tggtctaata ggtgatacca acatccgagc tccaggtgtt     180

cctgccagat tctcaggctc cctgattgga gacaaggctg ccctcaccat cacaggggca     240

cagactgagg atgaggcaat atatttctgt gctctttggt acagcaacca ttactgggtg     300

ttcggtggag gaaccaaact gactgtccta ggccagccca agtcttcgcc atcagtcacc     360

ctgtttccac cttcctctga agagctcgag actaacaagg ccacactggt gtgtacgatc     420

actgatttct acccaggtgt ggtgacagtg gactggaagg tagatggtac ccctgtcact     480

cagggtatgg agacaaccca gccttccaaa cagagcaaca acaagtacat ggctagcagc     540

tacctgaccc tgacagcaag agcatgggaa aggcatagca gttacagctg ccaggtcact     600

catgaaggtc acactgtgga gaagagtttg tcccgtgctg actgttcc                  648

<210> SEQ ID NO 107
<211> LENGTH: 216
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 107

```
Gln Ala Val Val Thr Gln Glu Ser Ala Leu Thr Thr Ser Pro Gly Glu
1               5                   10                  15

Thr Val Thr Leu Thr Cys Arg Ser Ser Ala Gly Ala Val Thr Thr Ser
            20                  25                  30

Asn Phe Ala Asn Trp Val Gln Glu Lys Pro Asp His Leu Phe Thr Gly
        35                  40                  45

Leu Ile Gly Asp Thr Asn Ile Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Tyr Trp Val Phe Gly Gly Gly Thr Lys Leu Thr Val Leu Gly Gln
            100                 105                 110

Pro Lys Ser Ser Pro Ser Val Thr Leu Phe Pro Pro Ser Ser Glu Glu
        115                 120                 125

Leu Glu Thr Asn Lys Ala Thr Leu Val Cys Thr Ile Thr Asp Phe Tyr
    130                 135                 140

Pro Gly Val Val Thr Val Asp Trp Lys Val Asp Gly Thr Pro Val Thr
145                 150                 155                 160

Gln Gly Met Glu Thr Thr Gln Pro Ser Lys Gln Ser Asn Asn Lys Tyr
                165                 170                 175

Met Ala Ser Ser Tyr Leu Thr Leu Thr Ala Arg Ala Trp Glu Arg His
            180                 185                 190

Ser Ser Tyr Ser Cys Gln Val Thr His Glu Gly His Thr Val Glu Lys
        195                 200                 205

Ser Leu Ser Arg Ala Asp Cys Ser
    210                 215
```

<210> SEQ ID NO 108
<211> LENGTH: 1323
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 108

```
gaggtgcagc ttcaggagtc aggacctagc ctcgtgaaac cttctcagac tctgtccctc     60

acctgttctg tcactggcga ctccatcacc agtggttact ggaactggat ccggaaattc    120

ccagggaata aacttgagta catggggtac ataagctaca gtggtaaaac ttactacaat    180

ccatctctca aaagtcgaat ctccatcact cgagacacat ccaagaacca ttactacctg    240

cagttgattt ctgtgactgc tgaggacaca gccacatatt actgtgcaag gtctaagtac    300

gactatgcta tggactactg gggtcaagga acctcagtca ccgtctcctc agccaaaacg    360

acacccccat ctgtctatcc actggcccct ggatctgctg cccaaactaa ctccatggtg    420

accctgggat gcctggtcaa gggctatttc cctgagccag tgacagtgac ctggaactct    480

ggatccctgt ccagcggtgt gcacaccttc ccagctgtcc tgcagtctga cctctacact    540

ctgagcagct cagtgactgt cccctccagc acctggccca gcgagaccgt cacctgcaac    600

gttgcccacc cggccagcag caccaaggtg gacaagaaaa ttgtgcccag ggattgtggt    660

tgtaagcctt gcatatgtac agtcccagaa gtatcatctg tcttcatctt ccccccaaag    720
```

```
cccaaggatg tgctcaccat tactctgact cctaaggtca cgtgtgttgt ggtagacatc    780

agcaaggatg atcccgaggt ccagttcagc tggtttgtag atgatgtgga ggtgcacaca    840

gctcagacgc aaccccggga ggagcagttc aacagcactt tccgctcagt cagtgaactt    900

cccatcatgc accaggactg gctcaatggc aaggagttca aatgcagggt caacagtgca    960

gctttccctg cccccatcga gaaaaccatc tccaaaacca aaggcagacc gaaggctcca   1020

caggtgtaca ccattccacc tcccaaggag cagatggcca aggataaagt cagtctgacc   1080

tgcatgataa cagacttctt ccctgaagac attactgtgg agtggcagtg gaatgggcag   1140

ccagcggaga actacaagaa cactcagccc atcatggaca cagatggctc ttacttcgtc   1200

tacagcaagc tcaatgtgca gaagagcaac tgggaggcag gaaatacttt cacctgctct   1260

gtgttacatg agggcctgca caaccaccat actgagaaga gcctctccca ctctcctggt   1320

aaa                                                                 1323
```

```
<210> SEQ ID NO 109
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Lys Ile Val Pro Arg Asp Cys Gly Cys Lys Pro Cys
    210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
```

```
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415

Phe Thr Cys Ser Val Leu His Glu Gly Leu His Asn His His Thr Glu
            420                 425                 430

Lys Ser Leu Ser His Ser Pro Gly Lys
        435                 440


<210> SEQ ID NO 110
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

gacattgtgc tgacccaatc tccagcttct ttggctgtgt ctctaggaca gagggccacc     60

atctcctgca gagccagcga aattgttgat aattttggca ttagttttat gaactggttc    120

caacagaaac caggacagcc acccaaactc ctcatctatg ctgcatccaa ccaaggatcc    180

ggggtccctg ccaggtttag tggcagtggg tctgggacag acttcagcct caacatccat    240

cctgtggagg aggatgatac tgcaatgtat ttctgtcagc aaagtaagga ggttcctccg    300

acgttcggtg gaggcaccaa gctggaaatc aaacgggctg atgctgcacc aactgtatcc    360

atcttcccac catccagtga gcagttaaca tctggaggtg cctcagtcgt gtgcttcttg    420

aacaacttct accccaaaga catcaatgtc aagtggaaga ttgatggcag tgaacgacaa    480

aatggcgtcc tgaacagttg gactgatcag gacagcaaag acagcaccta cagcatgagc    540

agcaccctca cgttgaccaa ggacgagtat gaacgacata acagctatac ctgtgaggcc    600

actcacaaga catcaacttc acccattgtc aagagcttca acaggaatga gtgt          654


<210> SEQ ID NO 111
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 111

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ile Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 112

```
cgactggagc acgaggacac tga                                              23
```

<210> SEQ ID NO 113
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 113

```
ctaatacgac tcactatagg gcaagcagtg gtatcaacgc agagt                      45
```

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
ctaatacgac tcactatagg gc 22

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
tatgcaaggc ttacaaccac a 21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
aggacagggc ttgattgtgg g 21

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
ctcattcctg ttgaagctct tgacaat 27

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
gcacgggaca aactcttctc 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
cacagtgtcc ccttcatgtg 20

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gtaaaacgac ggccagt 17

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
caggaaacag ctatgacc 18

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

```
Glu Ile Asn Pro Asp Ser Arg Thr Ile Asn Tyr Ala Pro Ser Val Lys
1               5                   10                  15

Gly
```

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

```
Arg Val Arg Ile His Tyr Tyr Gly Ala Met Asp Ser
1               5                   10
```

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

```
Gly Phe Thr Phe Ser Arg His
1               5
```

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

```
Arg Val Arg Ile His Tyr Tyr Gly Ala Met Asp Ser
1               5                   10
```

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Gly Gly Ser Ile Ser Ser Gly
1 5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Gly Phe Thr Phe Ser Arg His Trp
1 5

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Ala Arg Arg Val Arg Ile His Tyr Tyr Gly Ala Met Asp Ser
1 5 10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Gly Gly Ser Ile Ser Ser Gly Tyr
1 5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Arg Ala Ser Gln Asn Val Gly Ser Ser Leu Val
1 5 10

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Ser Ala Ser Phe Leu Tyr Ser
1 5

<210> SEQ ID NO 132
<211> LENGTH: 363
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 132

gaggtgaagc ttctcgagtc tggaggtggc ctggtgcagc cgggtggatc cctgaaactc     60

tcctgtgcag cctcaggatt cgattttagt agacactgga tgagttgggt ccggctggct    120

ccagggaaag ggctagaatg gatcgcagaa attaatccag atagcagaac gataaactat    180

acgccatctc taaaggagaa attcatcatc tccagagaca acgccaaaaa ttcgctgttt    240

ctgcaaatga acagagtgag atctgaggac acagcccttt attactgtgc aagacgggta    300

agaattcatt actacggcgc tatggacagc tggggtcaag gaacctcagt caccgtctcc    360

tca                                                                  363


<210> SEQ ID NO 133
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Ser Trp Gly
            100                 105                 110

Gln Gly Thr Ser Val Thr Val Ser Ser
        115                 120


<210> SEQ ID NO 134
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

gaggttcagc tggtagaatc cggaggaggg ttggtccaac ctggtggatc actcagactt     60

tcatgcgccg ccagcggctt tgacttctca cgacattgga tgagctgggt ccggcaggct    120

ccaggcaagg gcctcgagtg ggttagcgag atcaatccag acagcagaac cattaactat    180

acacccagtc tgaaggagcg gttcaccata agccgtgata atgccaagaa ctccctgtac    240

ttgcagatga actccttgcg cgctgaagat acagctgtgt actattgtgc aaggcgcgtg    300

cgaatccact attacggggc aatggattct tggggccagg gtactaccgt gactgtgagt    360

tct                                                                  363
```

<210> SEQ ID NO 135
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 135

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Thr Pro Ser Leu
    50                  55                  60

Lys Glu Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110

Gln Gly Thr Thr Val Thr Val Ser Ser
        115                 120
```

<210> SEQ ID NO 136
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
gaggttcagc tggtagaatc cggaggaggg ttggtccaac ctggtggatc actcagactt     60

tcatgcgccg ccagcggctt taccttctca cgacattgga tgagctgggt ccggcaggct    120

ccaggcaagg gcctcgagtg ggttagcgag atcaatccag acagcagaac cattaactat    180

gcccccagtg tgaagggccg gttcaccata agccgtgata atgccaagaa ctccctgtac    240

ttgcagatga actccttgcg cgctgaagat acagctgtgt actattgtgc aaggcgcgtg    300

cgaatccact attacggggc aatggattct tggggccagg gtactaccgt gactgtgagt    360

tct                                                                   363
```

<210> SEQ ID NO 137
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Trp Met Ser Trp Val Arg Gln Ala Pro Gly Lys Gly Leu Glu Trp Val
        35                  40                  45
```

```
Ser Glu Ile Asn Pro Asp Ser Arg Thr Ile Asn Tyr Ala Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110

Gln Gly Thr Thr Val Thr Val Ser Ser
        115                 120


<210> SEQ ID NO 138
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138

gatatccagt tgactcagtc tcagtccttt gtgagtacat cagtgggcga cagggtcacc     60

gtgacctgcc gagcatcaca gaacgttgga agctctcttg tctggtatca gcaaaagcct    120

gggaagagcc ccaaaaccct catctattct gcttcctttc tgtactccgg cgtaccaagt    180

agattctctg gtagcggatc cgggacagag ttcactctca caattagcag tgtgcagcct    240

gaggatttcg ccgactactt ctgtcagcaa tacaataact atcccctgac ttttggtggc    300

ggcaccaaag tggaaatcaa g                                              321


<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Leu Thr Gln Ser Gln Ser Phe Val Ser Thr Ser Val Gly
1               5                   10                  15

Asp Arg Val Thr Val Thr Cys Arg Ala Ser Gln Asn Val Gly Ser Ser
            20                  25                  30

Leu Val Trp Tyr Gln Gln Lys Pro Gly Lys Ser Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Ala Asp Tyr Phe Cys Gln Gln Tyr Asn Asn Tyr Pro Leu
                85                  90                  95

Thr Phe Gly Gly Gly Thr Lys Val Glu Ile Lys
            100                 105


<210> SEQ ID NO 140
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 140

```
gacattcagc tgactcagtc gccgtcgttt ttgtcggcgt ccgtgggtga cagagtgact     60

atcacatgtc gcgcttcgca aaacgtcgga tcatcgcttg tgtggtatca gcagaaaccc    120

ggtaaagccc ctaagaccct catctattca gcgtcatttc tgtatagcgg ggtcccctca    180

cggttcagcg gatccggctc cgggaccgag ttcacactca ctatttcgag cttgcagccg    240

gaagattttg caacgtacta ctgccagcaa tacaataact acccactcac gttcggaggg    300

ggaacgaagg tagagatcaa g                                               321
```

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asn Val Gly Ser Ser
            20                  25                  30

Leu Val Trp Tyr Gln Gln Lys Pro Gly Lys Ala Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys
            100                 105
```

<210> SEQ ID NO 142
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

```
caagttcagc tgcaagaatc cggaccagga ttggtcaaac cttcagagac actcagcctg     60

acttgcaccg tgagcggtgg cagcatatcc tccggttatt ggaactggat ccggcagcca    120

ccaggcaagg gcctcgagtg gattggctac atcagctata gcgggaaaac ctattacaac    180

cccagtctga agagccgagt gaccataagc gtcgatacaa gtaagaacca gttctccctg    240

aagctctcat ccgtgaccgc cgctgataca gctgtgtact attgtgcaag gtcaaagtat    300

gactacgcaa tggactattg gggccagggt actctggtga ctgtgagttc t             351
```

<210> SEQ ID NO 143
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
        115
```

<210> SEQ ID NO 144
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
caagttcagc tgcaagaatc cggaccagga ttggtcaaac ccagcgaaac actctctctt     60

acatgcaccg tgagcggcga ctctatcacc tcagggtatt ggaattggat tcggaaaccc    120

ccaggcaaga agctcgagta catgggttac atcagttaca gcgggaaaac ctactataac    180

cccagtctga agagcagaat caccataagc cgtgatacct ctaagaacca gtactccctg    240

aagctgagtt ccgtaacagc agctgataca gctgtgtact attgtgcaag gagtaagtat    300

gactacgcaa tggactattg gggccagggt actcttgtga ctgtgagttc t             351
```

<210> SEQ ID NO 145
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Lys Pro Pro Gly Lys Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
```

115

<210> SEQ ID NO 146
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 146

```
caagttcagc tgcaagaatc cggaccagga ttggtcaaac cttcagagac actcagcctg     60

acttgcaccg tgagcggtgg cagcatatcc tccggttatt ggaactggat ccggaagcca    120

ccaggcaaga agctcgagta cattggctac atcagctata gcgggaaaac ctattacaac    180

cccagtctga agagccgagt gaccataagc agggatacaa gtaagaacca gttctccctg    240

aagctctcat ccgtgaccgc cgctgataca gctgtgtact attgtgcaag gtcaaagtat    300

gactacgcaa tggactattg gggccagggt actctggtga ctgtgagttc t            351
```

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Lys Pro Pro Gly Lys Lys Leu Glu Tyr Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser
        115
```

<210> SEQ ID NO 148
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148

```
gatatcgtta tgacccagag cccacttagt ttgcctgtta ctcctggcga gcctgccagt     60

atttcttgcc gtgctagcga aatcgtggat aactttggta tatcattcat gaattggtat    120

ctccaaaaac ctggccaaag cccccagctc cttatctacg ccgctagcaa ccaggggtcc    180

ggggtacctg atagattttc aggcagcggc tctggaaccg acttcacact gaagatttcc    240

cgggtggagg ccgaggacgt gggcgtgtac tattgtcaac agtccaagga agtccctccc    300
```

```
actttcggcg gtgggacaaa ggttgagatt aag                              333


<210> SEQ ID NO 149
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ile Val Asp Asn Phe
            20                  25                  30

Gly Ile Ser Phe Met Asn Trp Tyr Leu Gln Lys Pro Gly Gln Ser Pro
        35                  40                  45

Gln Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Lys
                85                  90                  95

Glu Val Pro Pro Thr Phe Gly Gly Gly Thr Lys Val Glu Ile Lys
            100                 105                 110


<210> SEQ ID NO 150
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

gcctcaacaa aaggaccaag tgtgttccca ctcgcccccta gcagcaagag tacatccggg      60

ggcactgcag cactcggctg cctcgtcaag gattattttc cagagccagt aaccgtgagc     120

tggaacagtg gagcactcac ttctggtgtc catacttttc ctgctgtcct gcaaagctct     180

ggcctgtact cactcagctc cgtcgtgacc gtgccatctt catctctggg cactcagacc     240

tacatctgta atgtaaacca caagcctagc aatactaagg tcgataagcg ggtggaaccc     300

aagagctgcg acaagactca cacttgtccc ccatgccctg cccctgaact tctgggcggt     360

cccagcgtct tttgttccc accaaagcct aaagatactc tgatgataag tagaacaccc      420

gaggtgacat gtgttgttgt agacgtttcc cacgaggacc cagaggttaa gttcaactgg     480

tacgttgatg gagtcgaagt acataatgct aagaccaagc ctagagagga gcagtataat     540

agtacatacc gtgtagtcag tgttctcaca gtgctgcacc aagactggct caacggcaaa     600

gaatacaaat gcaaagtgtc caacaaagca ctcccagccc ctatcgagaa gactattagt     660

aaggcaaagg ggcagcctcg tgaaccacag gtgtacactc tgccacccag tagagaggaa     720

atgacaaaga accaagtctc attgacctgc ctggtgaaag gcttctaccc cagcgacatc     780

gccgttgagt gggagagtaa cggtcagcct gagaacaatt acaagacaac ccccccagtg     840

ctggatagtg acgggtcttt ctttctgtac agtaagctga ctgtggacaa gtcccgctgg     900

cagcagggta acgtcttcag ctgttccgtg atgcacgagg cattgcacaa ccactacacc     960

cagaagtcac tgagcctgag cccagggaag                                      990
```

<210> SEQ ID NO 151
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 152
<211> LENGTH: 321
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 152

```
cgcacagtcg ccgctccctc cgtgttcatc tttccaccaa gtgatgagca actgaagtct      60

ggtactgctt cagtcgtgtg tctgctgaac aatttctacc ctcgagaagc caaagtccaa     120

tggaaggtag acaacgcact gcagtccggc aatagccaag aatcagttac cgaacaggat     180

tcaaaggaca gtacatattc cctgagcagc actctgaccc tgtcaaaggc cgattacgag     240

aaacacaagg tctatgcttg cgaagtgaca catcagggac tgtccagccc agtgacaaaa     300

tcttttaacc gtggggagtg t                                               321
```

<210> SEQ ID NO 153
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

```
cgcacagttg ctgcccccag cgtgttcatt ttcccaccta gcgatgagca gctgaaaagc      60

ggtactgcct ctgtcgtatg cttgctcaac aacttttacc cacgtgaggc taaggtgcag     120

tggaaagtgg ataatgcact tcaatctgga aacagtcaag agtccgtgac agaacaggac     180

agcaaagact caacttattc actctcttcc accctgactc tgtccaaggc agactatgaa     240

aaacacaagg tatacgcctg cgaggttaca caccagggtt tgtctagtcc tgtcaccaag     300

tccttcaata ggggcgaatg t                                               321
```

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 155
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

```
gaggtgaagc ttctcgagtc tggaggtggc ctggtgcagc cgggtggatc cctgaaactc      60
tcctgtgcag cctcaggatt cgattttagt agacactgga tgagttgggt ccggctggct     120
ccagggaaag ggctagaatg gatcgcagaa attaatccag atagcagaac gataaactat     180
acgccatctc taaaggagaa attcatcatc tccagagaca acgccaaaaa ttcgctgttt     240
ctgcaaatga acagagtgag atctgaggac acagcccttt attactgtgc aagacgggta     300
agaattcatt actacggcgc tatggacagc tggggtcaag gaacctcagt caccgtctcc     360
tcagcctcaa caaaaggacc aagtgtgttc ccactcgccc ctagcagcaa gagtacatcc     420
gggggcactg cagcactcgg ctgcctcgtc aaggattatt ttccagagcc agtaaccgtg     480
agctggaaca gtggagcact cacttctggt gtccatactt ttcctgctgt cctgcaaagc     540
tctggcctgt actcactcag ctccgtcgtg accgtgccat cttcatctct gggcactcag     600
acctacatct gtaatgtaaa ccacaagcct agcaatacta aggtcgataa gcgggtggaa     660
cccaagagct gcgacaagac tcacacttgt cccccatgcc ctgcccctga acttctgggc     720
ggtcccagcg tctttttgtt cccaccaaag cctaaagata ctctgatgat aagtagaaca     780
cccgaggtga catgtgttgt tgtagacgtt tcccacgagg acccagaggt taagttcaac     840
tggtacgttg atggagtcga agtacataat gctaagacca agcctagaga ggagcagtat     900
aatagtacat accgtgtagt cagtgttctc acagtgctgc accaagactg gctcaacggc     960
aaagaataca aatgcaaagt gtccaacaaa gcactcccag cccctatcga gaagactatt    1020
agtaaggcaa aggggcagcc tcgtgaacca caggtgtaca ctctgccacc cagtagagag    1080
gaaatgacaa agaaccaagt ctcattgacc tgcctggtga aaggcttcta ccccagcgac    1140
atcgccgttg agtgggagag taacggtcag cctgagaaca attacaagac aaccccccca    1200
gtgctggata gtgacgggtc tttctttctg tacagtaagc tgactgtgga caagtcccgc    1260
tggcagcagg gtaacgtctt cagctgttcc gtgatgcacg aggcattgca caaccactac    1320
acccagaagt cactgagcct gagcccaggg aag                                 1353
```

<210> SEQ ID NO 156
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg His
            20                  25                  30

Trp Met Ser Trp Val Arg Leu Ala Pro Gly Lys Gly Leu Glu Trp Ile
        35                  40                  45

Ala Glu Ile Asn Pro Asp Ser Arg Thr Ile Asn Tyr Thr Pro Ser Leu
    50                  55                  60

Lys Glu Lys Phe Ile Ile Ser Arg Asp Asn Ala Lys Asn Ser Leu Phe
65                  70                  75                  80

Leu Gln Met Asn Arg Val Arg Ser Glu Asp Thr Ala Leu Tyr Tyr Cys
                85                  90                  95

Ala Arg Arg Val Arg Ile His Tyr Tyr Gly Ala Met Asp Ser Trp Gly
            100                 105                 110
```

```
Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 157
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157

```
gacattgtgt tgacccagtc tcaaaaaatc gtgtccacat cagtaggagc cagggtcagc     60
```

```
gtcacctgca aggccagtca gaatgtgggt tctagtttag tctggtatca acagaaacca    120

ggtcaatctc ctaaaacact gatttactcg gcatccttcc ggtacagtgg agtccctgat    180

cgcttcacag gcagtggatc tgggacagat ttcactctca ccatcagcaa tgtgcagtct    240

gaagacttgg cagattattt ctgtcaacaa tataataact atccgctcac gttcggtgct    300

gggaccaagc tggagctgaa acgcacagtc gccgctccct ccgtgttcat ctttccacca    360

agtgatgagc aactgaagtc tggtactgct tcagtcgtgt gtctgctgaa caatttctac    420

cctcgagaag ccaaagtcca atggaaggta gacaacgcac tgcagtccgg caatagccaa    480

gaatcagtta ccgaacagga ttcaaaggac agtacatatt ccctgagcag cactctgacc    540

ctgtcaaagg ccgattacga gaaacacaag gtctatgctt gcgaagtgac acatcaggga    600

ctgtccagcc cagtgacaaa atcttttaac cgtggggagt gt                       642
```

<210> SEQ ID NO 158
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Asp Ile Val Leu Thr Gln Ser Gln Lys Ile Val Ser Thr Ser Val Gly
1               5                   10                  15

Ala Arg Val Ser Val Thr Cys Lys Ala Ser Gln Asn Val Gly Ser Ser
            20                  25                  30

Leu Val Trp Tyr Gln Gln Lys Pro Gly Gln Ser Pro Lys Thr Leu Ile
        35                  40                  45

Tyr Ser Ala Ser Phe Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 159
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
gaggtgcagc ttcaggagtc aggacctagc ctcgtgaaac cttctcagac tctgtccctc     60
acctgttctg tcactggcga ctccatcacc agtggttact ggaactggat ccggaaattc    120
ccagggaata aacttgagta catggggtac ataagctaca gtggtaaaac ttactacaat    180
ccatctctca aaagtcgaat ctccatcact cgagacacat ccaagaacca ttactacctg    240
cagttgattt ctgtgactgc tgaggacaca gccacatatt actgtgcaag gtctaagtac    300
gactatgcta tggactactg gggtcaagga acctcagtca ccgtctcctc agcctcaaca    360
aaaggaccaa gtgtgttccc actcgcccct agcagcaaga gtacatccgg gggcactgca    420
gcactcggct gcctcgtcaa ggattatttt ccagagccag taaccgtgag ctggaacagt    480
ggagcactca cttctggtgt ccatactttt cctgctgtcc tgcaaagctc tggcctgtac    540
tcactcagct ccgtcgtgac cgtgccatct tcatctctgg gcactcagac ctacatctgt    600
aatgtaaacc acaagcctag caatactaag gtcgataagc gggtggaacc caagagctgc    660
gacaagactc acacttgtcc cccatgccct gcccctgaac ttctgggcgg tcccagcgtc    720
tttttgttcc caccaaagcc taaagatact ctgatgataa gtagaacacc cgaggtgaca    780
tgtgttgttg tagacgtttc ccacgaggac ccagaggtta agttcaactg gtacgttgat    840
ggagtcgaag tacataatgc taagaccaag cctagagagg agcagtataa tagtacatac    900
cgtgtagtca gtgttctcac agtgctgcac caagactggc tcaacggcaa agaatacaaa    960
tgcaaagtgt ccaacaaagc actcccagcc cctatcgaga agactattag taaggcaaag   1020
gggcagcctc gtgaaccaca ggtgtacact ctgccaccca gtagagagga aatgacaaag   1080
aaccaagtct cattgacctg cctggtgaaa ggcttctacc ccagcgacat cgccgttgag   1140
tgggagagta acggtcagcc tgagaacaat tacaagacaa cccccccagt gctggatagt   1200
gacgggtctt tctttctgta cagtaagctg actgtggaca agtcccgctg gcagcagggt   1260
aacgtcttca gctgttccgt gatgcacgag gcattgcaca accactacac ccagaagtca   1320
ctgagcctga gcccagggaa g                                              1341
```

<210> SEQ ID NO 160
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Ser Ile Thr Arg Asp Thr Ser Lys Asn His Tyr Tyr Leu
65                  70                  75                  80

Gln Leu Ile Ser Val Thr Ala Glu Asp Thr Ala Thr Tyr Tyr Cys Ala
                85                  90                  95

Arg Ser Lys Tyr Asp Tyr Ala Met Asp Tyr Trp Gly Gln Gly Thr Ser
```

```
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 161
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161

```
gacattgtgc tgacccaatc tccagcttct ttggctgtgt ctctaggaca gagggccacc      60

atctcctgca gagccagcga aattgttgat aattttggca ttagttttat gaactggttc     120
```

```
caacagaaac caggacagcc acccaaactc ctcatctatg ctgcatccaa ccaaggatcc    180

ggggtccctg ccaggtttag tggcagtggg tctgggacag acttcagcct caacatccat    240

cctgtggagg aggatgatac tgcaatgtat ttctgtcagc aaagtaagga ggttcctccg    300

acgttcggtg gaggcaccaa gctggaaatc aaacgcacag tcgccgctcc ctccgtgttc    360

atctttccac caagtgatga gcaactgaag tctggtactg cttcagtcgt gtgtctgctg    420

aacaatttct accctcgaga agccaaagtc caatggaagg tagacaacgc actgcagtcc    480

ggcaatagcc aagaatcagt taccgaacag gattcaaagg acagtacata ttccctgagc    540

agcactctga ccctgtcaaa ggccgattac gagaaacaca aggtctatgc ttgcgaagtg    600

acacatcagg gactgtccag cccagtgaca aaatctttta accgtgggga gtgt          654
```

<210> SEQ ID NO 162
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 162

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ile Val Asp Asn Phe
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 163
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163

```
gaggttcagc tggtagaatc cggaggaggg ttggtccaac ctggtggatc actcagactt     60
tcatgcgccg ccagcggctt tgacttctca cgacattgga tgagctgggt ccggcaggct    120
ccaggcaagg gcctcgagtg ggttagcgag atcaatccag acagcagaac cattaactat    180
acacccagtc tgaaggagcg gttcaccata agccgtgata atgccaagaa ctccctgtac    240
ttgcagatga actccttgcg cgctgaagat acagctgtgt actattgtgc aaggcgcgtg    300
cgaatccact attacggggc aatggattct tggggccagg gtactaccgt gactgtgagt    360
tctgcctcaa caaaaggacc aagtgtgttc ccactcgccc ctagcagcaa gagtacatcc    420
gggggcactg cagcactcgg ctgcctcgtc aaggattatt ttccagagcc agtaaccgtg    480
agctggaaca gtggagcact cacttctggt gtccatactt ttcctgctgt cctgcaaagc    540
tctggcctgt actcactcag ctccgtcgtg accgtgccat cttcatctct gggcactcag    600
acctacatct gtaatgtaaa ccacaagcct agcaatacta aggtcgataa gcgggtggaa    660
cccaagagct gcgacaagac tcacacttgt cccccatgcc ctgcccctga acttctgggc    720
ggtcccagcg tctttttgtt cccaccaaag cctaaagata ctctgatgat aagtagaaca    780
cccgaggtga catgtgttgt tgtagacgtt tcccacgagg acccagaggt taagttcaac    840
tggtacgttg atggagtcga agtacataat gctaagacca agcctagaga ggagcagtat    900
aatagtacat accgtgtagt cagtgttctc acagtgctgc accaagactg gctcaacggc    960
aaagaataca aatgcaaagt gtccaacaaa gcactcccag cccctatcga gaagactatt   1020
agtaaggcaa aggggcagcc tcgtgaacca caggtgtaca ctctgccacc cagtagagag   1080
gaaatgacaa agaaccaagt ctcattgacc tgcctggtga aaggcttcta ccccagcgac   1140
atcgccgttg agtgggagag taacggtcag cctgagaaca attacaagac aacccccccca   1200
gtgctggata gtgacgggtc tttctttctg tacagtaagc tgactgtgga caagtcccgc   1260
tggcagcagg gtaacgtctt cagctgttcc gtgatgcacg aggcattgca caaccactac   1320
acccagaagt cactgagcct gagcccaggg aag                                 1353
```

```
<210> SEQ ID NO 164
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Thr Pro Ser Leu
    50                  55                  60

Lys Glu Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110
```

```
Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 165
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165

gaggttcagc tggtagaatc cggaggaggg ttggtccaac ctggtggatc actcagactt     60

tcatgcgccg ccagcggctt taccttctca cgacattgga tgagctgggt ccggcaggct    120
```

```
ccaggcaagg gcctcgagtg ggttagcgag atcaatccag acagcagaac cattaactat    180

gcccccagtg tgaagggccg gttcaccata agccgtgata atgccaagaa ctccctgtac    240

ttgcagatga actccttgcg cgctgaagat acagctgtgt actattgtgc aaggcgcgtg    300

cgaatccact attacggggc aatggattct tggggccagg gtactaccgt gactgtgagt    360

tctgcctcaa caaaaggacc aagtgtgttc ccactcgccc ctagcagcaa gagtacatcc    420

gggggcactg cagcactcgg ctgcctcgtc aaggattatt ttccagagcc agtaaccgtg    480

agctggaaca gtggagcact cacttctggt gtccatactt ttcctgctgt cctgcaaagc    540

tctggcctgt actcactcag ctccgtcgtg accgtgccat cttcatctct gggcactcag    600

acctacatct gtaatgtaaa ccacaagcct agcaatacta aggtcgataa gcgggtggaa    660

cccaagagct gcgacaagac tcacacttgt cccccatgcc ctgcccctga acttctgggc    720

ggtcccagcg tctttttgtt cccaccaaag cctaaagata ctctgatgat aagtagaaca    780

cccgaggtga catgtgttgt tgtagacgtt tcccacgagg acccagaggt taagttcaac    840

tggtacgttg atggagtcga agtacataat gctaagacca agcctagaga ggagcagtat    900

aatagtacat accgtgtagt cagtgttctc acagtgctgc accaagactg gctcaacggc    960

aaagaataca aatgcaaagt gtccaacaaa gcactcccag cccctatcga gaagactatt   1020

agtaaggcaa aggggcagcc tcgtgaacca caggtgtaca ctctgccacc cagtagagag   1080

gaaatgacaa agaaccaagt ctcattgacc tgcctggtga aaggcttcta ccccagcgac   1140

atcgccgttg agtgggagag taacggtcag cctgagaaca attacaagac aacccccccca   1200

gtgctggata gtgacgggtc tttctttctg tacagtaagc tgactgtgga caagtcccgc   1260

tggcagcagg gtaacgtctt cagctgttcc gtgatgcacg aggcattgca caaccactac   1320

acccagaagt cactgagcct gagcccaggg aag                                1353
```

```
<210> SEQ ID NO 166
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg His
            20                  25                  30

Trp Met Ser Trp Val Arg Gln Ala Pro Gly Lys Gly Leu Glu Trp Val
        35                  40                  45

Ser Glu Ile Asn Pro Asp Ser Arg Thr Ile Asn Tyr Ala Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Val Arg Ile His Tyr Tyr Gly Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 167
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

gatatccagt tgactcagtc tcagtccttt gtgagtacat cagtgggcga cagggtcacc     60

gtgacctgcc gagcatcaca gaacgttgga agctctcttg tctggtatca gcaaaagcct    120

gggaagagcc ccaaaaccct catctattct gcttcctttc tgtactccgg cgtaccaagt    180

agattctctg gtagcggatc cgggacagag ttcactctca caattagcag tgtgcagcct    240
```

```
gaggatttcg ccgactactt ctgtcagcaa tacaataact atcccctgac ttttggtggc    300

ggcaccaaag tggaaatcaa gcgcacagtt gctgccccca gcgtgttcat tttcccacct    360

agcgatgagc agctgaaaag cggtactgcc tctgtcgtat gcttgctcaa caacttttac    420

ccacgtgagg ctaaggtgca gtggaaagtg gataatgcac ttcaatctgg aaacagtcaa    480

gagtccgtga cagaacagga cagcaaagac tcaacttatt cactctcttc caccctgact    540

ctgtccaagg cagactatga aaaacacaag gtatacgcct gcgaggttac acaccagggt    600

ttgtctagtc ctgtcaccaa gtccttcaat aggggcgaat gt                       642
```

<210> SEQ ID NO 168
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Asp Ile Gln Leu Thr Gln Ser Gln Ser Phe Val Ser Thr Ser Val Gly
1               5                   10                  15

Asp Arg Val Thr Val Thr Cys Arg Ala Ser Gln Asn Val Gly Ser Ser
            20                  25                  30

Leu Val Trp Tyr Gln Gln Lys Pro Gly Lys Ser Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Val Gln Pro
65                  70                  75                  80

Glu Asp Phe Ala Asp Tyr Phe Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 169
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169

```
gacattcagc tgactcagtc gccgtcgttt ttgtcggcgt ccgtgggtga cagagtgact     60
```

```
atcacatgtc gcgcttcgca aaacgtcgga tcatcgcttg tgtggtatca gcagaaaccc    120

ggtaaagccc ctaagaccct catctattca gcgtcatttc tgtatagcgg ggtcccctca    180

cggttcagcg gatccggctc cgggaccgag ttcacactca ctatttcgag cttgcagccg    240

gaagattttg caacgtacta ctgccagcaa tacaataact acccactcac gttcggaggg    300

ggaacgaagg tagagatcaa gcgcacagtt gctgccccca gcgtgttcat tttcccacct    360

agcgatgagc agctgaaaag cggtactgcc tctgtcgtat gcttgctcaa caacttttac    420

ccacgtgagg ctaaggtgca gtggaaagtg gataatgcac ttcaatctgg aaacagtcaa    480

gagtccgtga cagaacagga cagcaaagac tcaacttatt cactctcttc caccctgact    540

ctgtccaagg cagactatga aaaacacaag gtatacgcct gcgaggttac acaccagggt    600

ttgtctagtc ctgtcaccaa gtccttcaat aggggcgaat gt                      642
```

<210> SEQ ID NO 170
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asn Val Gly Ser Ser
            20                  25                  30

Leu Val Trp Tyr Gln Gln Lys Pro Gly Lys Ala Pro Lys Thr Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 171
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 171

```
caagttcagc tgcaagaatc cggaccagga ttggtcaaac cttcagagac actcagcctg     60
acttgcaccg tgagcggtgg cagcatatcc tccggttatt ggaactggat ccggcagcca    120
ccaggcaagg gcctcgagtg gattggctac atcagctata gcgggaaaac ctattacaac    180
cccagtctga agagccgagt gaccataagc gtcgatacaa gtaagaacca gttctccctg    240
aagctctcat ccgtgaccgc cgctgataca gctgtgtact attgtgcaag gtcaaagtat    300
gactacgcaa tggactattg gggccagggt actctggtga ctgtgagttc tgcctcaaca    360
aaaggaccaa gtgtgttccc actcgcccct agcagcaaga gtacatccgg gggcactgca    420
gcactcggct gcctcgtcaa ggattatttt ccagagccag taaccgtgag ctggaacagt    480
ggagcactca cttctggtgt ccatactttt cctgctgtcc tgcaaagctc tggcctgtac    540
tcactcagct ccgtcgtgac cgtgccatct tcatctctgg gcactcagac ctacatctgt    600
aatgtaaacc acaagcctag caatactaag gtcgataagc gggtggaacc caagagctgc    660
gacaagactc acacttgtcc cccatgccct gcccctgaac ttctgggcgg tcccagcgtc    720
tttttgttcc caccaaagcc taaagatact ctgatgataa gtagaacacc cgaggtgaca    780
tgtgttgttg tagacgtttc ccacgaggac ccagaggtta agttcaactg gtacgttgat    840
ggagtcgaag tacataatgc taagaccaag cctagagagg agcagtataa tagtacatac    900
cgtgtagtca gtgttctcac agtgctgcac caagactggc tcaacggcaa agaatacaaa    960
tgcaaagtgt ccaacaaagc actcccagcc cctatcgaga agactattag taaggcaaag   1020
gggcagcctc gtgaaccaca ggtgtacact ctgccaccca gtagagagga aatgacaaag   1080
aaccaagtct cattgacctg cctggtgaaa ggcttctacc ccagcgacat cgccgttgag   1140
tgggagagta acggtcagcc tgagaacaat tacaagacaa ccccccccagt gctggatagt   1200
gacgggtctt tctttctgta cagtaagctg actgtggaca agtcccgctg gcagcagggt   1260
aacgtcttca gctgttccgt gatgcacgag gcattgcaca accactacac ccagaagtca   1320
ctgagcctga gcccagggaa g                                              1341
```

<210> SEQ ID NO 172
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
```

```
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 173
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 173

```
caagttcagc tgcaagaatc cggaccagga ttggtcaaac ccagcgaaac actctctctt     60

acatgcaccg tgagcggcga ctctatcacc tcagggtatt ggaattggat tcggaaaccc    120
```

```
ccaggcaaga agctcgagta catgggttac atcagttaca gcgggaaaac ctactataac     180

cccagtctga agagcagaat caccataagc cgtgatacct ctaagaacca gtactccctg     240

aagctgagtt ccgtaacagc agctgataca gctgtgtact attgtgcaag gagtaagtat     300

gactacgcaa tggactattg gggccagggt actcttgtga ctgtgagttc tgcctcaaca     360

aaaggaccaa gtgtgttccc actcgcccct agcagcaaga gtacatccgg gggcactgca     420

gcactcggct gcctcgtcaa ggattatttt ccagagccag taaccgtgag ctggaacagt     480

ggagcactca cttctggtgt ccatactttt cctgctgtcc tgcaaagctc tggcctgtac     540

tcactcagct ccgtcgtgac cgtgccatct tcatctctgg gcactcagac ctacatctgt     600

aatgtaaacc acaagcctag caatactaag gtcgataagc gggtggaacc caagagctgc     660

gacaagactc acacttgtcc cccatgccct gcccctgaac ttctgggcgg tcccagcgtc     720

tttttgttcc caccaaagcc taaagatact ctgatgataa gtagaacacc cgaggtgaca     780

tgtgttgttg tagacgtttc ccacgaggac ccagaggtta agttcaactg gtacgttgat     840

ggagtcgaag tacataatgc taagaccaag cctagagagg agcagtataa tagtacatac     900

cgtgtagtca gtgttctcac agtgctgcac caagactggc tcaacggcaa agaatacaaa     960

tgcaaagtgt ccaacaaagc actcccagcc cctatcgaga agactattag taaggcaaag    1020

gggcagcctc gtgaaccaca ggtgtacact ctgccaccca gtagagagga aatgacaaag    1080

aaccaagtct cattgacctg cctggtgaaa ggcttctacc ccagcgacat cgccgttgag    1140

tgggagagta acggtcagcc tgagaacaat tacaagacaa ccccccccagt gctggatagt    1200

gacgggtctt tctttctgta cagtaagctg actgtggaca agtcccgctg gcagcagggt    1260

aacgtcttca gctgttccgt gatgcacgag gcattgcaca accactacac ccagaagtca    1320

ctgagcctga gcccagggaa g                                              1341
```

```
<210> SEQ ID NO 174
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Lys Pro Pro Gly Lys Lys Leu Glu Tyr Met
        35                  40                  45

Gly Tyr Ile Ser Tyr Ser Gly Lys Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 175
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

```
caagttcagc tgcaagaatc cggaccagga ttggtcaaac cttcagagac actcagcctg     60

acttgcaccg tgagcggtgg cagcatatcc tccggttatt ggaactggat ccggaagcca    120

ccaggcaaga agctcgagta cattggctac atcagctata gcgggaaaac ctattacaac    180

cccagtctga agagccgagt gaccataagc agggatacaa gtaagaacca gttctccctg    240

aagctctcat ccgtgaccgc cgctgataca gctgtgtact attgtgcaag gtcaaagtat    300

gactacgcaa tggactattg gggccagggt actctggtga ctgtgagttc tgcctcaaca    360
```

```
aaaggaccaa gtgtgttccc actcgcccct agcagcaaga gtacatccgg gggcactgca    420

gcactcggct gcctcgtcaa ggattatttt ccagagccag taaccgtgag ctggaacagt    480

ggagcactca cttctggtgt ccatactttt cctgctgtcc tgcaaagctc tggcctgtac    540

tcactcagct ccgtcgtgac cgtgccatct tcatctctgg gcactcagac ctacatctgt    600

aatgtaaacc acaagcctag caatactaag gtcgataagc gggtggaacc caagagctgc    660

gacaagactc acacttgtcc cccatgccct gcccctgaac ttctgggcgg tcccagcgtc    720

tttttgttcc caccaaagcc taaagatact ctgatgataa gtagaacacc cgaggtgaca    780

tgtgttgttg tagacgtttc ccacgaggac ccagaggtta agttcaactg gtacgttgat    840

ggagtcgaag tacataatgc taagaccaag cctagagagg agcagtataa tagtacatac    900

cgtgtagtca gtgttctcac agtgctgcac caagactggc tcaacggcaa agaatacaaa    960

tgcaaagtgt ccaacaaagc actcccagcc cctatcgaga agactattag taaggcaaag   1020

gggcagcctc gtgaaccaca ggtgtacact ctgccaccca gtagagagga aatgacaaag   1080

aaccaagtct cattgacctg cctggtgaaa ggcttctacc ccagcgacat cgccgttgag   1140

tgggagagta acggtcagcc tgagaacaat tacaagacaa cccccccagt gctggatagt   1200

gacgggtctt tctttctgta cagtaagctg actgtggaca agtcccgctg gcagcagggt   1260

aacgtcttca gctgttccgt gatgcacgag gcattgcaca accactacac ccagaagtca   1320

ctgagcctga gcccagggaa g                                               1341
```

```
<210> SEQ ID NO 176
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Tyr Trp Asn Trp Ile Arg Lys Pro Pro Gly Lys Lys Leu Glu Tyr Ile
        35                  40                  45

Gly Tyr Ile Ser Tyr Ser Gly Lys Thr Tyr Tyr Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Lys Tyr Asp Tyr Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 177
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177

gatatcgtta tgacccagag cccacttagt ttgcctgtta ctcctggcga gcctgccagt      60

atttcttgcc gtgctagcga aatcgtggat aactttggta tatcattcat gaattggtat     120

ctccaaaaac ctggccaaag cccccagctc cttatctacg ccgctagcaa ccaggggtcc     180

ggggtacctg atagattttc aggcagcggc tctggaaccg acttcacact gaagatttcc     240

cgggtggagg ccgaggacgt gggcgtgtac tattgtcaac agtccaagga agtccctccc     300

actttcggcg gtgggacaaa ggttgagatt aagcgcacag ttgctgcccc cagcgtgttc     360

attttcccac ctagcgatga gcagctgaaa agcggtactg cctctgtcgt atgcttgctc     420

aacaactttt acccacgtga ggctaaggtg cagtggaaag tggataatgc acttcaatct     480

ggaaacagtc aagagtccgt gacagaacag gacagcaaag actcaactta ttcactctct     540

tccaccctga ctctgtccaa ggcagactat gaaaaacaca aggtatacgc ctgcgaggtt     600
```

```
acacaccagg gtttgtctag tcctgtcacc aagtccttca ataggggcga atgt         654


<210> SEQ ID NO 178
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ile Val Asp Asn Phe
            20                  25                  30

Gly Ile Ser Phe Met Asn Trp Tyr Leu Gln Lys Pro Gly Gln Ser Pro
        35                  40                  45

Gln Leu Leu Ile Tyr Ala Ala Ser Asn Gln Gly Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Lys
                85                  90                  95

Glu Val Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

ANTI-RON ANTIBODIES

CROSS-REFERENCE TO RELATED APPLICATIONS

This application claims the benefit of and priority to U.S. Provisional Application Ser. No. 61/466,679, filed Mar. 23, 2011, and U.S. Provisional Application Ser. No. 61/361,808, filed Jul. 6, 2010; the contents of each application are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jul. 18, 2011, is named AVO-010.txt and is 174,495 bytes in size.

FIELD OF THE INVENTION

The field of the invention is molecular biology, immunology and oncology. More particularly, the field is therapeutic antibodies.

BACKGROUND

Recepteur d' Origine Nantais (RON), also known as Macrophage Stimulating Protein Receptor (MSP R, or MST1-R), is a member of the MET family of receptor tyrosine kinases that binds the ligand known as Macrophage Stimulating Protein (MSP). RON is composed of a 40 kDa extracellular α chain and a 150 kDa transmembrane β chain. The β chain is responsible for the intrinsic kinase activity, and the extracellular portions of the two chains function together as the ligand binding domain (Wagh et al., 2008, Adv. Cancer Res. 100:1-33).

MSP binding to RON activates multiple downstream signaling pathways and mediates multiple cellular activities. RON pathway dysregulation is involved in inflammatory response, wound healing and liver regeneration. RON signaling can sustain tumor growth, survival, motility, invasion and angiogenesis in certain malignancies. The RON protein exists in several splice variants, some of which are tumorigenic in animal models of cancer. One such splice variant is delta 160 RON, which lacks exons 5 and 6 (Lu et al., 2007, Cancer Lett. 257:157-164).

When activated by ligand binding, RON activates the PI3K/AKT pathway and the MAPK pathway. RON also affects cells through interactions with other receptors, e.g., c-Met, integrins and EGFR. To date, no activating mutations in RON exons have been reported. Alternative splicing and overexpression appear to be the main mechanisms for constitutive activation of the receptor. Several small molecule inhibitors have been reported that inhibit multiple receptor tyrosine kinases, including RON, examples of which include EXCEL-2880, (Qian et al., 2009, Cancer Res. 69:8009-8016) and BMS-77607 (Schroeder et al., 2009 J. Med Chem. 52:1251-1254). A dual c-met/RON inhibitor has also been reported, Amgen compound I (Zhang et al., 2008, Cancer Res. 68:6680-6687). A recent publication describes a selective RON small molecule inhibitor (Raeppel et al., 2010 Bioorg Med Chem Lett 20:2745-9). Several antibodies that inhibit human RON activity have been reported (Huet et al., US 2009/0226442; Pereira et al., US 2009/0136510; Zhu et al., WO 2006/020258; Pereira et al., WO 2005/120557; and commercial antibody MAB691, R&D Systems, Minneapolis, Minn.).

Naturally occurring antibodies are multimeric proteins that contain four polypeptide chains (FIG. 1). Two of the polypeptide chains are called heavy chains (H chains), and two of the polypeptide chains are called light chains (L chains). The immunoglobulin heavy and light chains are connected by an interchain disulfide bond. The immunoglobulin heavy chains are connected by interchain disulfide bonds. A light chain consists of one variable region ($V_L$ in FIG. 1) and one constant region ($C_L$ in FIG. 1). The heavy chain consists of one variable region ($V_H$ in FIG. 1) and at least three constant regions ($CH_1$, $CH_2$ and $CH_3$ in FIG. 1). The variable regions determine the specificity of the antibody. Each variable region comprises three hypervariable regions also known as complementarity determining regions (CDRs) flanked by four relatively conserved framework regions (FRs). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies.

Although antibodies that bind RON are known in the art, there is still a need for improved RON antibodies that can be used as therapeutic agents.

SUMMARY

The invention is based, in part, upon the discovery of a family of antibodies that specifically bind human RON. The antibodies contain RON binding sites based on the CDRs of the antibodies. The antibodies can be used as therapeutic agents. When used as therapeutic agents, the antibodies are engineered, e.g., humanized, to reduce or eliminate an immune response when administered to a human patient.

The antibodies prevent or inhibit the activation of (i.e., neutralize) human RON. In some embodiments, the antibodies prevent RON from binding to its ligand, MSP, thereby neutralizing RON activity. In certain embodiments, the antibodies prevent RON activation without inhibiting RON binding to MSP. The antibodies can be used to inhibit the downstream signaling of the breast tumor cell line T47D. Furthermore, when administered to a mammal, the antibodies can inhibit or reduce tumor growth in the mammal.

These and other aspects and advantages of the invention will become apparent upon consideration of the following figures, detailed description, and claims. As used herein, "including" means without limitation, and examples cited are non-limiting.

DESCRIPTION OF THE DRAWINGS

The invention can be more completely understood with reference to the following drawings.

FIG. 2 is a sequence alignment showing the amino acid sequence of the complete immunoglobulin heavy chain variable region of antibodies 07F01, 12B11, 17F06, 18H09 and 29B06. The amino acid sequences for each antibody are aligned against one another, and $CDR_1$, $CDR_2$, and $CDR_3$, are identified in boxes. The unboxed sequences represent framework (FR). Alignment positioning (gaps) are based on Kabat numbering, rather than an alignment algorithm such as Clustal sequences.

FIG. 3 is a sequence alignment showing the $CDR_1$, $CDR_2$, and $CDR_3$ sequences for each of the immunoglobulin heavy chain variable region sequences in FIG. 2.

FIG. 4 is a sequence alignment showing the amino acid sequence of the complete immunoglobulin light chain variable region of antibodies 07F01, 12B11, 17F06, 18H09 and 29B06. The amino acid sequences for each antibody are aligned against one another, and $CDR_1$, $CDR_2$, and $CDR_3$, are identified in boxes. The unboxed sequences represent framework (FR) sequences. Alignment positioning (gaps) are based on Kabat numbering, rather than an alignment algorithm such as Clustal sequences.

FIG. 5 is a sequence alignment showing the $CDR_1$, $CDR_2$, and $CDR_3$ sequences for each of the immunoglobulin light chain variable region sequences in FIG. 4.

FIG. 12A is a schematic diagram showing the amino acid sequences of the complete immunoglobulin heavy chain variable region of 07F01 (SEQ ID NO: 2) and the complete heavy chain variable regions denoted as Chimeric 07F01 C102S (SEQ ID NO: 133), Sh07F01 Hv3-48 (SEQ ID NO: 135), and Sh07F01 Hv3-48 D28T T60A L63V E65G (SEQ ID NO: 137). The amino acid sequences for each heavy chain variable region are aligned against one another, and Complementary Determining Sequences (CDR) (Kabat definition), $CDR_1$, $CDR_2$, and $CDR_3$, are identified in boxes. The unboxed sequences represent framework (FR) sequences.

FIG. 12B is a schematic diagram showing the amino acid sequences of the complete immunoglobulin heavy chain variable region of 29B06 (SEQ ID NO: 42) and the complete heavy chain variable regions denoted as Sh29B06_Hv4-59 (SEQ ID NO: 143), Hu29B06 Hv4-59 (SEQ ID NO: 145), and Hu29B06 Hv4-59 D27G T30S M48I I67V Y78F (SEQ ID NO: 147). The amino acid sequences for each heavy chain variable region are aligned against one another, and $CDR_1$, $CDR_2$, and $CDR_3$ sequences (Kabat definition) are identified in boxes. The unboxed sequences represent framework (FR) sequences.

FIG. 13A is a schematic diagram showing the $CDR_1$, $CDR_2$, and $CDR_3$ sequences (Kabat definition) for each of the variable region sequences shown in FIG. 12A.

FIG. 13B is a schematic diagram showing the $CDR_1$, $CDR_2$, and $CDR_3$ sequences (Kabat definition) for each of the variable region sequences shown in FIG. 12B.

FIG. 14A is a schematic diagram showing the amino acid sequences of the complete light chain variable region of 07F01 (SEQ ID NO: 4) and the complete light chain variable regions denoted as HE L 07F01 Kv1-9 (SEQ ID NO: 139) and Sh07F01 Kv1-9 F1 (SEQ ID NO: 141). The amino acid sequences for each light chain variable region are aligned against one another, and $CDR_1$, $CDR_2$, and $CDR_3$ sequences (Kabat definition) are identified in boxes. The unboxed sequences represent framework (FR) sequences.

FIG. 14B is a schematic diagram showing the amino acid sequences of the complete light chain variable region of 29B06 (SEQ ID NO: 44) and the complete light chain variable region denoted as Sh29B06 Kv2-28 (SEQ ID NO: 149). The amino acid sequences for each light chain variable region are aligned against one another, and $CDR_1$, $CDR_2$, and $CDR_3$ sequences (Kabat definition) are identified in boxes. The unboxed sequences represent framework (FR) sequences.

FIG. 15A is a sequence alignment showing the $CDR_1$, $CDR_2$, and $CDR_3$ sequences (Kabat definition) for each of the variable region sequences shown in FIG. 14A.

FIG. 15B is a sequence alignment showing the $CDR_1$, $CDR_2$, and $CDR_3$ sequences (Kabat definition) for each of the variable region sequences shown in FIG. 14B.

DETAILED DESCRIPTION

Figure 1:
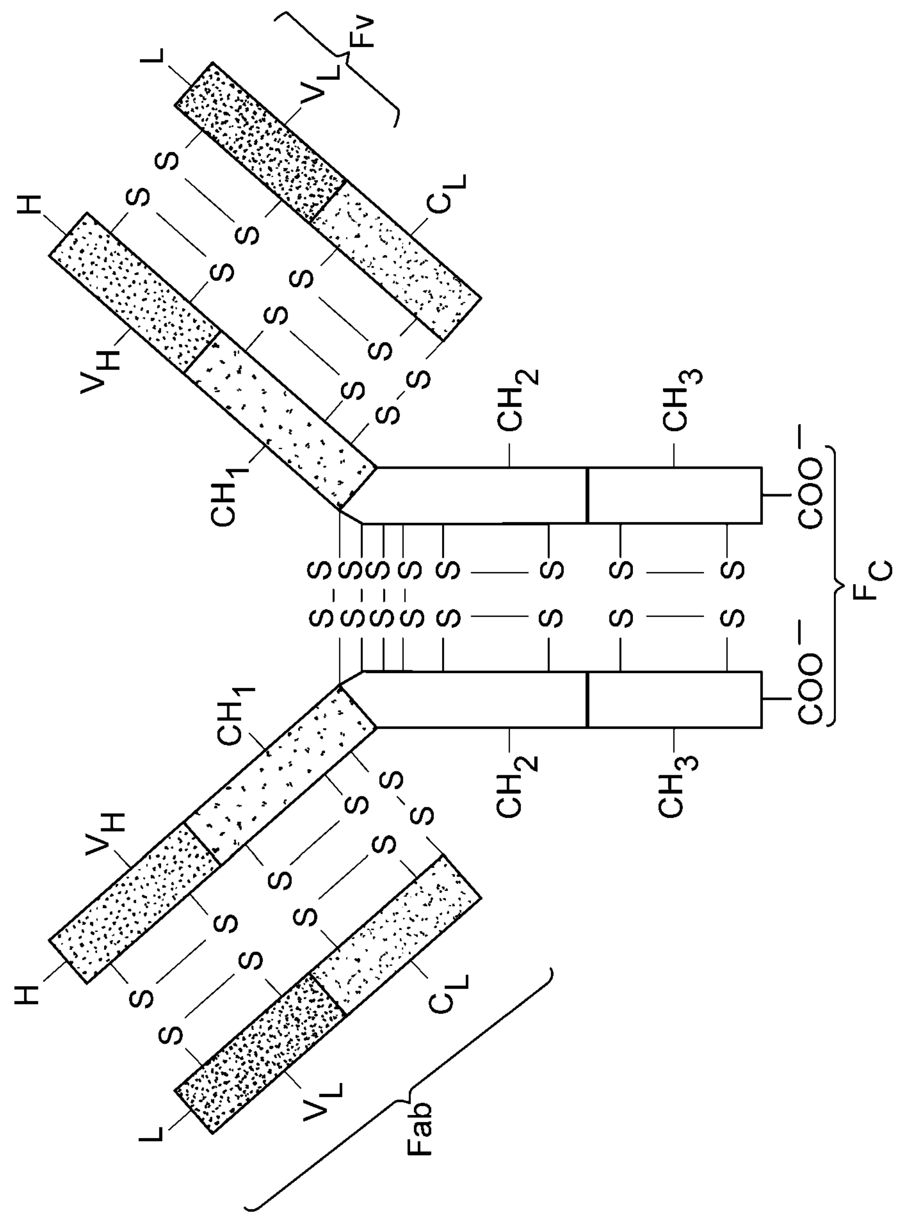
FIG. 1 (prior art) is a schematic representation of a typical naturally-occurring antibody.

The anti-RON antibodies disclosed herein are based on the antigen binding sites of certain monoclonal antibodies that have been selected on the basis of binding and neutralizing the activity of human RON. The antibodies contain immunoglobulin variable region CDR sequences that define a binding site for human RON.

In view of the neutralizing activity of these antibodies, they are useful for modulating the growth and/or proliferation of certain types of cancer cells. When used as a therapeutic agent, the antibodies can be engineered to minimize or eliminate an immune response when administered to a human patient. In some embodiments, the antibodies are fused or conjugated to other moieties, such as effector molecules (e.g., other proteins or small molecule therapeutics), a detectable label or a toxin moiety. Various features and aspects of the invention are discussed in more detail below.

As used herein, unless otherwise indicated, the term "antibody" means an intact antibody (e.g., an intact monoclonal antibody) or antigen-binding fragment of an antibody (e.g., an antigen-binding fragment of a monoclonal antibody), including an intact antibody or antigen-binding fragment that has been modified, engineered or chemically conjugated, or that is a human antibody. Examples of antibodies that have been modified or engineered are chimeric antibodies, humanized antibodies, and multispecific antibodies (e.g., bispecific antibodies). Examples of antigen-binding fragments include Fab, Fab', $F(ab')_2$, Fv, single chain antibodies (e.g., scFv), minibodies and diabodies. An antibody conjugated to a toxin moiety is an example of a chemically conjugated antibody.

I. Antibodies that Bind RON

The antibodies disclosed herein comprise: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human RON protein.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding human RON. A $CDR_{H1}$ comprises an amino acid sequence selected from the group consisting of SEQ ID NO: 5 (07F01), SEQ ID NO: 51 (07F01), SEQ ID NO: 124 (Sh07F01 Hv3-48 D28T T60A L63V E65G), SEQ ID NO: 15 (12B11), SEQ ID NO: 53 (12B11), SEQ ID NO: 25 (17F06), SEQ ID NO: 55 (17F06), SEQ ID NO: 35 (18H09), SEQ ID NO: 57 (18H09), SEQ ID NO: 45 (29B06), SEQ ID NO: 59 (29B06), and SEQ ID NO: 126 (Sh29B06 Hv4-59, Hu29B06 Hv4-59 D27G T30S M48I I67V Y78F); a $CDR_{H2}$ comprises an amino acid sequence selected from the group consisting of SEQ ID NO: 6 (07F01), SEQ ID NO: 16 (12B11), SEQ ID NO: 26 (17F06), SEQ ID NO: 36 (18H09), SEQ ID NO: 46 (29B06), and SEQ ID NO: 122 (Sh07F01 Hv3-48 D28T T60A L63V E65G); and a $CDR_{H3}$ comprises an amino acid sequence selected from the group consisting of SEQ ID NO:7 (07F01), SEQ ID NO: 17 (12B11), SEQ ID NO: 27 (17F06), SEQ ID NO: 37 (18H09), SEQ ID NO: 47 (29B06), and SEQ ID NO: 123 (Chimeric 07F01 C102S, Sh07F01 Hv3-48, Sh07F01 Hv3-48 D28T T60A L63V E65G). Throughout the specification a particular SEQ ID NO. is followed in parentheses by the antibody that was the origin of that sequence. For example, "SEQ ID NO: 5 (07F01)" means that SEQ ID NO: 5 comes from antibody 07F01.

In some embodiments, the antibody comprises an immunoglobulin heavy chain variable region comprising a $CDR_{H1}$ comprising the amino acid sequence of SEQ ID NO: 5 (07F01), SEQ ID NO: 51 (07F01), or SEQ ID NO: 124 (Sh07F01 Hv3-48 D28T T60A L63V E65G); a $CDR_{H2}$ comprising the amino acid sequence of SEQ ID NO: 6 (07F01) or SEQ ID NO: 122 (Sh07F01 Hv3-48 D28T T60A L63V E65G), and a $CDR_{H3}$ comprising the amino acid sequence of SEQ ID NO: 7 (07F01) or SEQ ID NO: 123 (Chimeric 07F01 C102S, Sh07F01 Hv3-48, Sh07F01 Hv3-48 D28T T60A L63V E65G).

In some embodiments, the heavy chain variable region comprises a $CDR_{H1}$ comprising the amino acid sequence of SEQ ID NO: 5 (07F01), a $CDR_{H2}$ comprising the amino acid sequence of SEQ ID NO: 122 (Sh07F01 Hv3-48 D28T T60A L63V E65G), and a $CDR_{H3}$ comprising the amino acid sequence of SEQ ID NO: 123 (Chimeric 07F01 C102S, Sh07F01 Hv3-48, Sh07F01 Hv3-48 D28T T60A L63V E65G).

In some embodiments, the antibody comprises an immunoglobulin heavy chain variable region comprising a $CDR_{H1}$ comprising the amino acid sequence of SEQ ID NO: 15 (12B11) or SEQ ID NO: 53 (12B11), a $CDR_{H2}$ comprising the amino acid sequence of SEQ ID NO: 16 (12B11), and a $CDR_{H3}$ comprising the amino acid sequence of SEQ ID NO: 17 (12B11).

In some embodiments, the heavy chain variable region comprises a $CDR_{H1}$ comprising the amino acid sequence of SEQ ID NO: 25 (17F06) or SEQ ID NO: 55 (17F06), a $CDR_{H2}$ comprising the amino acid sequence of SEQ ID NO: 26 (17F06), and a $CDR_{H3}$ comprising the amino acid sequence of SEQ ID NO: 27 (17F06).

In some embodiments, the heavy chain variable region comprises a $CDR_{H1}$ comprising the amino acid sequence of SEQ ID NO: 35 (18H09) or SEQ ID NO: 57 (18H09), a $CDR_{H2}$ comprising the amino acid sequence of SEQ ID NO: 36 (18H09), and a $CDR_{H3}$ comprising the amino acid sequence of SEQ ID NO: 37 (18H09).

In some embodiments, the heavy chain variable region comprises a $CDR_{H1}$ comprising the amino acid sequence of SEQ ID NO: 45 (29B06), SEQ ID NO: 59 (29B06), or SEQ ID NO: 126 (Sh29B06 Hv4-59, Hu29B06 Hv4-59 D27G T30S M48I I67V Y78F), a $CDR_{H2}$ comprising the amino acid sequence of SEQ ID NO: 46 (29B06), and a $CDR_{H3}$ comprising the amino acid sequence of SEQ ID NO: 47 (29B06).

In some embodiments, the heavy chain variable region comprises a $CDR_{H1}$ comprising the amino acid sequence of SEQ ID NO: 45 (29B06) or SEQ ID NO: 126 (Sh29B06 Hv4-59, Hu29B06 Hv4-59 D27G T30S M48I I67V Y78F), a $CDR_{H2}$ comprising the amino acid sequence of SEQ ID NO: 46 (29B06), and a $CDR_{H3}$ comprising the amino acid sequence of SEQ ID NO: 47 (29B06).

Preferably, the $CDR_{H1}$, $CDR_{H2}$, and $CDR_{H3}$ sequences are interposed between human or humanized immunoglobulin FRs. The antibody can be an intact antibody or an antigen-binding antibody fragment.

In some embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the IgG light chain variable region and the IgG heavy chain variable region together define a single binding site for binding human RON. A $CDR_{L1}$ comprises an amino acid sequence selected from the group consisting of SEQ ID NO: 8 (07F01), SEQ ID NO: 18 (12B11), SEQ ID NO: 28 (17F06), SEQ ID NO: 38 (18H09), SEQ ID NO: 48 (29B06), and SEQ ID NO: 130 (HE L 07F01 Kv1-9, Sh07F01 Kv1-9 F1); a $CDR_{L2}$ comprises an amino acid sequence selected from the group consisting of SEQ ID NO: 9 (07F01), SEQ ID NO: 19 (12B11), SEQ ID NO: 29 (17F06), SEQ ID NO: 39 (18H09), SEQ ID NO: 49 (29B06), and SEQ ID NO: 131 (HE L 07F01 Kv1-9, Sh07F01 Kv1-9 F1); and a $CDR_{L3}$ comprises an amino acid sequence selected from the group consisting of SEQ ID NO: 10 (07F01), SEQ ID NO: 20 (12B11), SEQ ID NO:30 (17F06), SEQ ID NO: 40 (18H09), and SEQ ID NO: 50 (29B06).

In some embodiments, the antibody comprises an immunoglobulin light chain variable region comprising a $CDR_{L1}$ comprising the amino acid sequence of SEQ ID NO: 8 (07F01) or SEQ ID NO: 130 (HE L 07F01 Kv1-9, Sh07F01 Kv1-9 F1), a $CDR_{L2}$ comprising the amino acid sequence of SEQ ID NO: 9 (07F01) or SEQ ID NO: 131 (HE L 07F01 Kv1-9, Sh07F01 Kv1-9 F1), and a $CDR_{L3}$ comprising the amino acid sequence of SEQ ID NO: 10 (07F01).

In some embodiments, the antibody comprises an immunoglobulin light chain variable region comprising a $CDR_{L1}$ comprising the amino acid sequence of SEQ ID NO: 130 (HE L 07F01 Kv1-9, Sh07F01 Kv1-9 F1); a $CDR_{L2}$ comprising the amino acid sequence of SEQ ID NO: 131 (HE L 07F01 Kv1-9, Sh07F01 Kv1-9 F1); and a $CDR_{L3}$ comprising the amino acid sequence of SEQ ID NO: 10 (07F01).

In some embodiments, the antibody comprises an immunoglobulin light chain variable region comprising a $CDR_{L1}$ comprising the amino acid sequence of SEQ ID NO: 18 (12B11); a $CDR_{L2}$ comprising the amino acid sequence of SEQ ID NO: 19 (12B11); and a $CDR_{L3}$ comprising the amino acid sequence of SEQ ID NO: 20 (12B11).

In some embodiments, the antibody comprises an immunoglobulin light chain variable region comprising a $CDR_{L1}$ comprising the amino acid sequence of SEQ ID NO: 28 (17F06); a $CDR_{L2}$ comprising the amino acid sequence of SEQ ID NO: 29 (17F06); and a $CDR_{L3}$ comprising the amino acid sequence of SEQ ID NO: 30 (17F06).

In some embodiments, the antibody comprises an immunoglobulin light chain variable region comprising a $CDR_{L1}$ comprising the amino acid sequence of SEQ ID NO: 38 (18H09); a $CDR_{L2}$ comprising the amino acid sequence of SEQ ID NO: 39 (18H09); and a $CDR_{L3}$ comprising the amino acid sequence of SEQ ID NO: 40 (18H09).

In some embodiments, the antibody comprises an immunoglobulin light chain variable region comprising a $CDR_{L1}$ comprising the amino acid sequence of SEQ ID NO: 48 (29B06); a $CDR_{L2}$ comprising the amino acid sequence of SEQ ID NO: 49 (29B06); and a $CDR_{L3}$ comprising the amino acid sequence of SEQ ID NO: 50 (29B06).

Preferably, the $CDR_{L1}$, $CDR_{L2}$, and $CDR_{L3}$ sequences are interposed between human or humanized immunoglobulin FRs. The antibody can be an intact antibody or an antigen-binding antibody fragment.

In some embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding human RON. The $CDR_{H1}$ is an amino acid sequence selected from the group consisting of SEQ ID NO: 5 (07F01), SEQ ID NO: 51 (07F01), SEQ ID NO: 124 (Sh07F01 Hv3-48 D28T T60A L63V E65G), SEQ ID NO: 15 (12B11), SEQ ID NO: 53 (12B11), SEQ ID NO: 25 (17F06), SEQ ID NO: 55 (17F06), SEQ ID NO: 35 (18H09), SEQ ID NO: 57 (18H09), SEQ ID NO: 45 (29B06), SEQ ID NO: 59 (29B06), and SEQ ID NO: 126 (Sh29B06 Hv4-59, Hu29B06 Hv4-59 D27G T30S M48I I67V Y78F); the $CDR_{H2}$ is an amino acid sequence selected from the group consisting SEQ ID NO: 6 (07F01), SEQ ID NO: 16 (12B11), SEQ ID NO: 26 (17F06), SEQ ID NO: 36 (18H09), SEQ ID NO: 46 (29B06), and SEQ ID NO: 122 (Sh07F01 Hv3-48 D28T T60A L63V E65G); and the $CDR_{H3}$ is an amino acid sequence selected from the group consisting of SEQ ID NO:7 (07F01), SEQ ID NO: 17 (12B11), SEQ ID NO: 27 (17F06), SEQ ID NO: 37 (18H09), SEQ ID NO: 47 (29B06), and SEQ ID NO: 123 (Chimeric 07F01 C102S, Sh07F01 Hv3-48, Sh07F01 Hv3-48 D28T T60A L63V E65G). The $CDR_{L1}$ is an amino acid sequence selected from the group consisting of SEQ ID NO: 8 (07F01), SEQ ID NO: 18 (12B11), SEQ ID NO: 28 (17F06), SEQ ID NO: 38 (18H09), SEQ ID NO: 48 (29B06), and SEQ ID NO: 130 (HE L 07F01 Kv1-9, Sh07F01 Kv1-9 F1); the $CDR_{L2}$ is an amino acid sequence selected from the group consisting of SEQ ID NO: 9 (07F01), SEQ ID NO: 19 (12B11), SEQ ID NO: 29 (17F06), SEQ ID NO: 39 (18H09), SEQ ID NO: 49 (29B06), and SEQ ID NO: 131 (HE L 07F01 Kv1-9, Sh07F01 Kv1-9 F1); and the $CDR_{L3}$ is an amino acid sequence selected from the group consisting of SEQ ID NO: 10 (07F01), SEQ ID NO: 20 (12B11), SEQ ID NO: 30 (17F06), SEQ ID NO: 40 (18H09), and SEQ ID NO: 50 (29B06).

The antibodies disclosed herein comprise an immunoglobulin heavy chain variable region and an immunoglobulin light chain variable region. In some embodiments, the antibody comprises an immunoglobulin heavy chain variable region selected from the group consisting of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), and SEQ ID NO: 147 (Hu29B06 Hv4-59 D27G T30S M48I I67V Y78F), and an immunoglobulin light chain variable region.

In other embodiments, the antibody comprises an immunoglobulin light chain variable region selected from the group consisting of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), and SEQ ID NO: 149 (Sh29B06 Kv2-28), and an immunoglobulin heavy chain variable region.

In some embodiments, the antibody comprises an immunoglobulin heavy chain variable region selected from the group consisting of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), and SEQ ID NO: 147 (Hu29B06 Hv4-59 D27G T30S M48I I67V Y78F), and an immunoglobulin light chain variable region selected from the group consisting of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), and SEQ ID NO: 149 (Sh29B06 Kv2-28).

In some embodiments, the antibody comprises an immunoglobulin heavy chain variable region comprising the amino acid sequence of SEQ ID NO: 2 (07F01), and an immunoglobulin light chain variable region comprising the amino acid sequence of SEQ ID NO: 4 (07F01).

In some embodiments, the antibody comprises an immunoglobulin heavy chain variable region comprising the amino acid sequence of SEQ ID NO: 12 (12B11), and an immunoglobulin light chain variable region comprising the amino acid sequence of SEQ ID NO: 14 (12B11).

In some embodiments, the antibody comprises an immunoglobulin heavy chain variable region comprising the amino acid sequence of SEQ ID NO: 22 (17F06), and an immunoglobulin light chain variable region comprising the amino acid sequence of SEQ ID NO: 24 (17F06).

In some embodiments, the antibody comprises an immunoglobulin heavy chain variable region comprising the amino acid sequence of SEQ ID NO: 32 (18H09), and an immunoglobulin light chain variable region comprising the amino acid sequence of SEQ ID NO: 34 (18H09).

In some embodiments, the antibody comprises an immunoglobulin heavy chain variable region comprising the amino acid sequence of SEQ ID NO: 42 (29B06), and an immunoglobulin light chain variable region comprising the amino acid sequence of SEQ ID NO: 44 (29B06).

In some embodiments, the antibody comprises an immunoglobulin heavy chain variable region comprising the amino acid sequence of SEQ ID NO: 137 (Sh07F01 Hv3-48 D28T T60A L63V E65G), and an immunoglobulin light chain variable region comprising the amino acid sequence of SEQ ID NO: 139 (HE L 07F01 Kv1-9).

In some embodiments, the antibody comprises an immunoglobulin heavy chain variable region comprising the amino acid sequence of SEQ ID NO: 147 (Hu29B06 Hv4-59 D27G T30S M48I I67V Y78F), and an immunoglobulin light chain variable region comprising the amino acid sequence of SEQ ID NO: 149 (Sh29B06 Kv2-28).

In certain embodiments, the antibodies disclosed herein comprise an immunoglobulin heavy chain and an immunoglobulin light chain. In some embodiments, the antibody comprises an immunoglobulin heavy chain selected from the group consisting of SEQ ID NO: 93 (07F01), SEQ ID NO: 97 (12B11), SEQ ID NO: 101 (17F06), SEQ ID NO: 105 (18H09), SEQ ID NO: 109 (29B06), SEQ ID NO: 156 (Chimeric 07F01 C102S IgG1), SEQ ID NO: 160 (Chimeric 29B06 IgG1), SEQ ID NO: 164 (Sh07F01 Hv3-48 IgG1), SEQ ID NO: 166 (Sh07F01 Hv3-48 D28T T60A L63V E65G IgG1), SEQ ID NO: 172 (Sh29B06 Hv4-59 IgG1), SEQ ID NO: 174 (Hu29B06 Hv4-59 IgG1), and SEQ ID NO: 176 (Hu29B06 Hv4-59 D27G T30S M48I I67V Y78F IgG1), and an immunoglobulin light chain.

In other embodiments, the antibody comprises an immunoglobulin light chain selected from the group consisting of SEQ ID NO: 95 (07F01), SEQ ID NO: 99 (12B11), SEQ ID NO: 103 (17F06), SEQ ID NO: 107 (18H09), SEQ ID NO: 111 (29B06), SEQ ID NO: 158 (Chimeric 07F01 Kappa), SEQ ID NO: 162 (Chimeric 29B06 Kappa), SEQ ID NO: 168 (HE L 07F01 Kv1-9 Kappa), SEQ ID NO: 170 (Sh07F01 Kv1-9 μl Kappa), and SEQ ID NO: 178 (Sh29B06 Kv2-28 Kappa), and an immunoglobulin heavy chain.

In some embodiments, the antibody comprises (i) an immunoglobulin heavy chain selected from the group consisting of SEQ ID NO: 93 (07F01), SEQ ID NO: 97 (12B11), SEQ ID NO: 101 (17F06), SEQ ID NO: 105 (18H09), SEQ ID NO: 109 (29B06), SEQ ID NO: 156 (Chimeric 07F01 C102S IgG1), SEQ ID NO: 160 (Chimeric 29B06 IgG1), SEQ ID NO: 164 (Sh07F01 Hv3-48 IgG1), SEQ ID NO: 166 (Sh07F01 Hv3-48 D28T T60A L63V E65G IgG1), SEQ ID NO: 172 (Sh29B06 Hv4-59 IgG1), SEQ ID NO: 174 (Hu29B06 Hv4-59 IgG1), and SEQ ID NO: 176 (Hu29B06 Hv4-59 D27G T30S M48I I67V Y78F IgG1), and (ii) an immunoglobulin light chain selected from the group consisting of SEQ ID NO: 95 (07F01), SEQ ID NO: 99 (12B11), SEQ ID NO: 103 (17F06), SEQ ID NO: 107 (18H09), SEQ ID NO: 111 (29B06), SEQ ID NO: 158 (Chimeric 07F01 Kappa), SEQ ID NO: 162 (Chimeric 29B06 Kappa), SEQ ID NO: 168 (HE L 07F01 Kv1-9 Kappa), SEQ ID NO: 170 (Sh07F01 Kv1-9 F1 Kappa), and SEQ ID NO: 178 (Sh29B06 Kv2-28 Kappa).

In some embodiments, the antibody comprises an immunoglobulin heavy chain comprising the amino acid sequence of SEQ ID NO: 93 (07F01), and an immunoglobulin light chain comprising the amino acid sequence of SEQ ID NO: 95 (07F01).

In some embodiments, the antibody comprises an immunoglobulin heavy chain comprising the amino acid sequence of SEQ ID NO: 97 (12B11), and an immunoglobulin light chain comprising the amino acid sequence of SEQ ID NO: 99 (12B11).

In some embodiments, the antibody comprises an immunoglobulin heavy chain comprising the amino acid sequence of SEQ ID NO: 101 (17F06), and an immunoglobulin light chain comprising the amino acid sequence of SEQ ID NO: 103 (17F06).

In some embodiments, the antibody comprises an immunoglobulin heavy chain comprising the amino acid sequence of SEQ ID NO: 105 (18H09), and an immunoglobulin light chain comprising the amino acid sequence of SEQ ID NO: 107 (18H09).

In some embodiments, the antibody comprises an immunoglobulin heavy chain comprising the amino acid sequence of SEQ ID NO: 109 (29B06), and an immunoglobulin light chain comprising the amino acid sequence of SEQ ID NO: 111 (29B06).

In some embodiments, the antibody comprises an immunoglobulin heavy chain comprising the amino acid sequence of SEQ ID NO: 166 (Sh07F01 Hv3-48 D28T T60A L63V E65G IgG1), and an immunoglobulin light chain comprising the amino acid sequence of SEQ ID NO: 168 (HE L 07F01 Kv1-9 Kappa).

In some embodiments, the antibody comprises an immunoglobulin heavy chain comprising the amino acid sequence of SEQ ID NO: 176 (Hu29B06 Hv4-59 D27G T30S M48I I67V Y78F IgG1), and an immunoglobulin light chain comprising the amino acid sequence of SEQ ID NO: 178 (Sh29B06 Kv2-28 Kappa).

In certain embodiments, an isolated antibody that binds human RON comprises an immunoglobulin heavy chain variable region comprising an amino acid sequence that is at least 70%, 75%, 80%, 85%, 90%, 95%, 98%, or 99% identical to the entire variable region or the framework region sequence of SEQ ID NO: 2 (07F01), SEQ ID NO: 12 (12B11), SEQ ID NO: 22 (17F06), SEQ ID NO: 32 (18H09), SEQ ID NO: 42 (29B06), SEQ ID NO: 133 (Chimeric 07F01 C102S), SEQ ID NO: 135 (Sh07F01 Hv3-48), SEQ ID NO: 137 (Sh07F01 Hv3-48 D28T T60A L63V E65G), SEQ ID NO: 143 (Sh29B06 Hv4-59), SEQ ID NO: 145 (Hu29B06 Hv4-59), or SEQ ID NO: 147 (Hu29B06 Hv4-59 D27G T30S M48I I67V Y78F).

In certain embodiments, an isolated antibody that binds human RON comprises an immunoglobulin light chain variable region comprising an amino acid sequence that is at least 70%, 75%, 80%, 85%, 90%, 95%, 98%, or 99% identical to the entire variable region or the framework region sequence of SEQ ID NO: 4 (07F01), SEQ ID NO: 14 (12B11), SEQ ID NO: 24 (17F06), SEQ ID NO: 34 (18H09), SEQ ID NO: 44 (29B06), SEQ ID NO: 139 (HE L 07F01 Kv1-9), SEQ ID NO: 141 (Sh07F01 Kv1-9 F1), or SEQ ID NO: 149 (Sh29B06 Kv2-28).

Homology or identity may be determined in various ways that are within the skill in the art, for instance, using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) PROC. NATL. ACAD. SCI. USA 87, 2264-2268; Altschul, (1993) J. MOL. EVOL. 36, 290-300; Altschul et al., (1997) NUCLEIC ACIDS RES. 25, 3389-3402, incorporated by reference) are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases see Altschul et al., (1994)

Nature Genetics 6, 119-129 which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, propoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In each of the foregoing embodiments, it is contemplated herein that immunoglobulin heavy chain variable region sequences and/or light chain variable region sequences that together bind human RON may contain amino acid alterations (e.g., at least 1, 2, 3, 4, 5, or 10 amino acid substitutions, deletions, or additions) in the framework regions of the heavy and/or light chain variable regions.

In certain embodiments, the antibody binds human RON with a $K_D$ of 1 nM, 900 pM, 750 pM, 650 pM, 600 pM, 500 pM, 400 pM, 300 pM, 250 pM, 200 pM, 150 pM, 100 pM, 50 pM or lower. Unless otherwise specified, $K_D$ values are determined by surface plasmon resonance methods under the conditions described in Examples 5 and 14.

Antibody Sh29B06-78 binds human RON with a $K_D$ of 500 pM, 250 pM, 200 pM, 150 pM, 100 pM or lower as measured by surface plasmon resonance methods under the conditions described in Examples 5 and 14. In an exemplary embodiment, antibody Sh29B06-78 binds human RON with a $K_D$ of 150 pM or lower as measured by surface plasmon resonance methods at 37° C. under the conditions described in Examples 5 and 14.

Antibody SH07F01-62 binds human RON with a $K_D$ of 500 pM, 400 pM, 350 pM, 300 pM, 250 pM, 200 pM, 150 pM, 100 pM or lower as measured by surface plasmon resonance methods under the conditions described in Examples 5 and 14. In an exemplary embodiment, antibody SH07F01-62 binds human RON with a $K_D$ of 250 pM to 350 pM or lower as measured by surface plasmon resonance methods at 37° C. under the conditions described in Examples 5 and 14.

In certain embodiments, the antibodies inhibit human MSP binding to human RON. For example, the antibodies can have an $IC_{50}$ (concentration at 50% of maximum inhibition) of about 5 nM, 2 nM, 1 nM or lower, when assayed using the protocol described in Examples 8 and 15.

Although the embodiments illustrated in the Examples comprise pairs of variable regions, pairs of full length antibody chains, or pairs of CDR1, CDR2 and CDR3 regions, one from a heavy chain and one from a light chain, a skilled artisan will recognize that alternative embodiments may comprise single heavy chain variable regions or single light chain variable regions, single full length antibody chains, or CDR1, CDR2 and CDR3 regions from one antibody chain, either heavy or light. The single variable region, full length antibody chain or CDR1, CDR2 and CDR3 region of one chain can be used to screen for corresponding domains in another chain, the two chains capable of forming an antibody that binds antigen. The screening may be accomplished by phage display screening methods using, e.g., a hierarchical dual combinatorial approach disclosed in PCT Publ. No. WO92/01047. In this approach, an individual colony containing either a heavy or light chain clone is used to infect a complete library of clones encoding the other chain (light or heavy), and the resulting two-chain specific antigen-binding domain is selected in accordance with phage display techniques as described.

II. Production of Antibodies

Methods for producing antibodies, such as those disclosed herein, are known in the art. For example, DNA molecules encoding light chain variable regions and/or heavy chain variable regions can be chemically synthesized using the sequence information provided herein. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, the sequences provided herein can be cloned out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of murine antibodies in hybridoma cells.

Nucleic acids encoding desired antibodies can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukayotic host cells, e.g., CHO cells, it is first inserted into an expression vector containing a suitable eukaryotic promoter, a secretion signal, IgG enhancers, and various introns. This expression vector optionally contains sequences encoding all or part of a constant region, enabling an entire, or a part of, a heavy or light chain to be expressed. The gene construct can be introduced into eukaryotic host cells using conventional techniques. The host cells express $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments, a host cell is transfected with a single vector expressing a polypeptide expressing an entire, or part of, a heavy chain (e.g., a heavy chain variable region) or a light chain (e.g., a light chain variable region). In other embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In still other embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced by growing a host cell transfected with an expression vector encoding such variable region, under conditions that permit expression of the polypeptide. Following expression, the polypeptide can be harvested and purified using techniques well known in the art, e.g., affinity tags such as glutathione-S-transferase (GST) and histidine tags.

A monoclonal antibody that binds human RON, or an antigen-binding fragment of the antibody, can be produced by growing a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified using techniques well known in the art, e.g., Protein A, Protein G, affinity tags such as glutathione-S-transferase (GST) and histidine tags. It is within ordinary skill in the art to express the heavy chain and the light chain from a single expression vector or from two separate expression vectors.

III. Antibody Modifications

Methods for reducing or eliminating the antigenicity of antibodies and antibody fragments are known in the art. When the antibodies are to be administered to a human, the antibodies preferably are "humanized" to reduce or eliminate antigenicity in humans. Preferably, the humanized antibodies have the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. Nos. 6,893,625 (Robinson); 5,500,362 (Robinson); and 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-RON antibody are grafted into human FRs or consensus human FRs. To create consensus human FRs, FRs from several human heavy chain or light chain amino acid sequences are aligned to identify a consensus amino acid sequence. CDR grafting is described in U.S. Pat. Nos. 7,022,500 (Queen); 6,982,321 (Winter); 6,180,370 (Queen); 6,054,297 (Carter); 5,693,762 (Queen); 5,859,205 (Adair); 5,693,761 (Queen); 5,565,332 (Hoogenboom); 5,585,089 (Queen); 5,530,101 (Queen); Jones et al. (1986) Nature 321: 522-525; Riechmann et al. (1988) Nature 332: 323-327; Verhoeyen et al. (1988) Science 239: 1534-1536; and Winter (1998) Febs Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol. 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains are said to be produced. See, e.g., U.S. Pat. Nos. 6,706,477 (Zauderer); 6,800,442 (Zauderer); and 6,872,518 (Zauderer).

Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. Nos. 5,766,886 (Studnicka); 5,770,196 (Studnicka); 5,821,123 (Studnicka); and 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997. Human mAbs can also be prepared and optimized from phage display libraries by techniques referenced in, e.g., Knappik et al., J. Mol. Biol. 296: 57-86, 2000; and Krebs et al., J. Immunol. Meth. 254:67-84 2001).

If the antibody is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

IV. Use of Antibodies

The antibodies disclosed herein can be used to treat various forms of cancer, e.g., non-small cell lung cancer, breast, ovarian, prostate, cervical, colorectal, lung, pancreatic, gastric, and head and neck cancers. The cancer cells are exposed to a therapeutically effective amount of the antibody so as to inhibit or reduce proliferation of the cancer cell. In some embodiments, the antibodies inhibit cancer cell proliferation by at least 40%, 50%, 60%, 70%, 80%, 90%, 95%, 98%, 99%, or 100%.

In some embodiments, the antibody (e.g., 07F01, 29B06, 17F06, 18H09, 12B11, sh29B06, sh07F01) inhibits or reduces proliferation of a tumor cell by inhibiting binding of human RON to its ligand, MSP. In some embodiments, the antibody (e.g., 07F01, 29B06, 17F06, 18H09, 12B11, sh29B06, sh07F01) inhibits or reduces proliferation of a tumor cell without inhibiting RON binding to MSP. The antibody (e.g., 07F01, 29B06, 17F06, 18H09, 12B11, sh29B06, sh07F01) can also be used in therapy. The antibody (e.g., 07F01, 29B06, 17F06, 18H09, 12B11, sh29B06, sh07F01) can be used to inhibit tumor growth in a mammal (e.g., a human patient). In some embodiments, use of the antibody to inhibit tumor growth in a mammal comprises administering to the mammal a therapeutically effective amount of the antibody.

In certain embodiments, antibody sh29B06-78 is used in therapy. For example, antibody sh29B06-78 can be used for inhibiting or reducing proliferation of a tumor cell. Antibody sh29B06-78 can also be used for inhibiting or reducing tumor growth in a mammal.

In other embodiments, antibody sh07F01-62 is used in therapy. For example, antibody sh07F01-62 can be used for inhibiting or reducing proliferation of a tumor cell. Antibody sh07F01-62 can also be used for inhibiting or reducing tumor growth in a mammal.

Cancers associated with overexpression or inappropriate activation of RON include non-small cell lung cancer, breast cancer, ovarian cancer, prostate cancer, lung cancer, colorectal cancer, pancreatic cancer, bladder cancer, and some forms of brain cancer, melanomas, and gastrointestinal cancers.

As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. In some embodiments, dosing is once every two weeks. A preferred route of administration is parenteral, e.g., intravenous infusion. Formulation of monoclonal antibody-based drugs is within ordinary skill in the art. In some embodiments, the antibody is lyophilized and reconstituted in buffered saline at the time of administration.

For therapeutic use, an antibody preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing antibodies, such as those disclosed herein, can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for monoclonal antibodies is IV infusion. Useful formulations can be prepared by methods well known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and are not intended to limit the scope or content of the invention in any way.

Example 1

Production of Human RON Extracellular Domain (ECD)

This Example describes the production of the antigen, hRON ECD protein. The use of the full length ECD as the immunogen, allowed for the selection of two classes of hybridomas: (a) those producing antibodies that interact with the ligand binding domain, thereby inhibiting contact of the ligand to the receptor; and (b) those producing antibodies that bind outside the ligand binding domain, thereby inhibiting the receptor functions through mechanisms other than inhibition of ligand binding.

DNA encoding the extracellular domain of human RON (hRON ECD) (ref seq. NM_002447) was amplified by PCR and subcloned using the XmaI/EcoRI restriction sites in-frame into the pEE14.4 vector (Lonza, Basel, Switzerland) containing THXmFC (Thrombin/His tag/Factor Xa-AJ mouse IgG-Fc), to produce a fusion protein. The resulting clone was linearized using the PvuI enzyme (NEBiolabs, Cat. No. R0150), then electroporated into CHO K1SVcells (Lonza). The electroporated cells were diluted in 200 ml CD CHO media (Gibco Cat. No. 10743-011). The next day, CD CHO media containing methionine sulfoximine (MSX) for a final concentration of 50 μM was added to the cells. After four weeks, positive clones were selected by sandwich ELISA in which the immobilized antibody was commercial monoclonal anti-hRON antibody MAB691 (R&D Systems), and the detection antibody was commercial polyclonal anti-hRON antibody AF691 (R&D Systems). Positive clones were re-transfected using LIPOFECTAMINE™ 2000 in a standard protocol. Cells were aliquoted into four separate shaker flasks and selected using 50 uM, 100 uM, 200 uM, and 400 uM MSX. After two weeks of selection, the individual flasks were checked for hRON-ECD protein expression by ELISA. The highest selection pressure, 400 μM MSX, yielded good protein expression and was chosen for scale-up and purification. Cells were grown for 2 weeks at 37° C. in BELLOCELL® bottles (Bellco Glass, Vineland, N.J.) at a concentration of 2-2.5×$10^6$ cells/ml in CD CHO media, with a final concentration of 80 μM MSX for protein production. The resulting cells were spun down in 500 ml conical tubes for 15 minutes. The supernatant was filtered using vacuum filtration using a 0.45 micron filter and then a 0.22 micron filter. The protein was then batch bound to PROSEP®-A beads (Millipore) at 4° C. overnight with rotation after adjusting the pH to 7.5. The beads were washed with 1×PBS and loaded onto disposable protein A affinity columns (Bio-Rad ECONO-PAC® columns; Bio-Rad cat. No. 732-1010). The beads were washed with 10 column volumes (CV) of glycine binding buffer (3M glycine ph 9.0, 1M NaCl). The protein was then eluted off the column using 5-10 CV of 200 mM glycine pH 2.5 acid elution buffer. The samples were then neutralized using 1.3 mL of 1.0 M Tris pH 8.0 neutralization buffer concentrated using VIVASPIN® concentrators (Sartorius Stedim Biotech).

Example 2

Anti-RON Antibodies

This Example describes the production of anti-hRON monoclonal antibodies. Immunizations, fusions, and primary screens were conducted at Maine Biotechnology Services Inc. (Portland, Me.), following the Repetitive Immunization Multiple Sites (RIMMS) protocol. Five AJ mice and five Balb/c mice were immunized with recombinant human RON extracellular domain (hRON-ECD). Two Balb/c mice with sera displaying the highest anti-RON activity by Enzyme Linked Immunosorbent Assay (ELISA) were chosen for subsequent fusion. Spleens and lymph nodes from the appropriate mice were harvested. B-cells were harvested and fused with a myeloma line. Fusion products were serially diluted onto forty 96-well plates to near clonality.

Approximately 4,000 supernatants from the cell fusions were screened by ELISA for binding to recombinant hRON-ECD. A total of 158 supernatants containing antibodies against RON were further characterized by in vitro biochemical and cell-based assays, as described below. A panel of hybridomas was selected, subcloned and expanded. Hybridoma cell lines were transferred to BioXCell (West Lebanon, N.H.) for antibody expression and purification by affinity chromatography on Protein G resin, under standard conditions.

Example 3

Screening Assays

A biochemical assay was carried out to identify antibodies that inhibit ligand binding. A cell-based assay was carried out to identify antibodies that inhibit MSP induced phosphoERK downstream signaling of the receptor. Antibodies that inhibited RON mediated cellular signaling were selected for further characterization regardless of whether they blocked ligand binding in the neutralization assay.

The biochemical neutralization assay measures inhibition of MSP binding to hRON by antibodies in hybridoma supernatants, using electrochemiluminescence (ECL). MA2400 96-well high binding plates (Meso Scale Discovery) were coated with 25 μl of 0.42 μg/mL hRON SEMA+PSI (an N-terminal portion of the ECD of hRON; R&D Systems) in PBS for one hour at room temperature with agitation. The plates were washed four times with PBS+0.1% TWEEN-20® (PBST), and blocked with 150 μl of charcoal-stripped fetal bovine serum (FBS) (Gibco). The hybridoma supernatant were added and incubated for 45 minutes at room temperature. After incubation, 5 μl of MSP (3 μg/mL) in charcoal stripped FBS was added to each well, and incubated for 45 minutes. The plate was washed four times with PBST, and 25 μl of 1 μg/mL biotinylated anti-MSP antibody (R&D Systems) was added to the plates for one hour at room temperature with agitation. The plates were washed four times with PBST, and incubated with 25 μl of 1 μg/mL ST-streptavidin (Meso Scale Discovery) for one hour at room temperature with agitation. The plates were washed four times with PBST, and 150 μl read buffer (Meso Scale Discovery) was added to each well before the plates were analyzed on a SECTOR® IMAGER 2400 (Meso Scale Discovery) instrument. Antibodies 07F01, 18H09 and 29B06 each blocked MSP binding to hRON SEMA+PSI in this neutralization assay.

In the cell-based assay, antibodies in the hybridoma supernatant were tested for inhibition of MSP-induced phosphorylation of ERK, which is a RON downstream signaling molecule. T47D cells were cultured in 96-well plates in RPMI 1640+10% FBS+ insulin. Medium was removed, and cells were incubated in serum-free medium for 24 hours. Hybridoma supernatants containing RON antibodies were added to the cells at a dilution of 1:4 in-serum-free medium, and incubated for one hour at 37° C. MSP (5 nM) was added to the wells and incubated for 15 minutes. Medium was removed, and cells were fixed in 4% paraformaldehyde (PFA) in PBS. Total ERK and phospho-ERK were measured according to the vendor's instructions (R&D Systems, DY1018). Antibodies 07F01, 12B11, 17F06, 18H09 and 29B06 each inhibited MSP induced ERK phosphorylation in T47D cells.

As discussed herein (see Examples 8 and 9), antibodies 07F01, 12B11, 17F06, 18H09 and 29B06 each inhibited MSP induced ERK phosphorylation in T47D cells, while only antibodies 07F01, 18H09 and 29B06 each blocked MSP binding to hRON SEMA+PSI in the neutralization assay. This suggests that antibodies 12B11 and 17F06 do not neutralize binding of MSP to the hRON SEMA+PSI domain, neutralize binding of MSP to RON in the context of the full RON extracellular domain, or function by a mechanism other than blocking MSP binding to RON.

Example 4

Antibody Sequence Analysis

The light chain isotype and heavy chain isotype of each monoclonal antibody in Example 2 was determined using the ISOSTRIP™ Mouse Monoclonal Antibody Isotyping Kit according the kit vendor's instructions (Roche Applied Science, Indianapolis, Ind.). All antibodies were found to be kappa or lambda light chain and IgG1 or IgG2a heavy chain.

The heavy and light chain variable regions of the mouse monoclonal antibodies were sequenced using 5' RACE (Rapid Amplification of cDNA Ends). Total RNA was extracted from each monoclonal hybridoma cell line using the RNEASY® Miniprep kit according to the kit vendor's instructions (Qiagen, Valencia, Calif.). Full-length first strand cDNA containing 5' ends was generated using either the GENERACER™ Kit (Invitrogen, Carlsbad, Calif.) or SMARTER™ RACE cDNA Amplification Kit (Clontech, Mountain View, Calif.) according to the kit vendor's instructions using random primers for 5' RACE.

The variable regions of the light (kappa or lambda) and heavy (IgG1 or IgG2b) chains were amplified by PCR, using KOD Hot Start Polymerase (EMD Chemicals, Gibbstown, N.J.), Expand High Fidelity PCR System (Roche Applied Science), or Advantage 2 Polymerase Mix (Clontech) according to the kit vendor's instructions. For amplification of 5' cDNA ends in conjunction with the GeneRacer™ Kit, the GeneRacer™ 5' Primer, 5' cgactggagcacgaggacactga 3' (SEQ ID NO: 112) (Invitrogen) was used as a 5' primer. For amplification of 5' cDNA ends in conjunction with the SMARTer™ RACE cDNA Amplification Kit, the Universal Primer Mix A primer (Clontech), a mix of: 5' CTAATACGACTCACTATAGGGCAAGCAGTGGTATCAACGCAGAGT 3' (SEQ ID NO: 113) and 5' CTAATACGACTCACTATAGGGC 3' (SEQ ID NO: 114), was used as a 5' primer. Heavy chain variable regions were amplified using the above 5' primers and a 3' IgG1 constant region specific primer, 5' TATGCAAGGCTTACAACCACA 3' (SEQ ID NO: 115), or a 3' IgG2a constant region specific primer, 5' AGGACAGGGCTTGATTGTGGG 3' (SEQ ID NO: 116). Kappa chain variable regions were amplified with the above 5' primers and a 3' kappa constant region specific primer, 5' CTCATTCCTGTTGAAGCTCTTGACAAT 3' (SEQ ID NO: 117). Lambda chain variable regions were amplified with the above 5' primers and a mix of 3' lambda constant region specific primers, 5' GCACGGGACAAACTCTTCTC 3' (SEQ ID NO: 118) and 5' CACAGTGTCCCCTTCATGTG 3' (SEQ ID NO: 119).

Individual PCR products were isolated by agarose gel electrophoresis and purified using the QIAQUICK™ Gel Purification kit according to the kit vendor's instructions (Qiagen). The PCR products were subsequently cloned into the PCR® 4Blunt TOPO® plasmid or PCR® 2.1-TOPO® plasmid using the ZERO BLUNT® TOPO® PCR Cloning Kit or the TOPO® TA Cloning Kit, respectively, according to the kit vendor's instructions (Invitrogen) and transformed into DH5-α bacteria (Invitrogen) through standard molecular biology techniques. Plasmid DNA isolated from transformed bacterial clones was sequenced using M13 Forward (5' GTAAAACGACGGCCAGT 3') (SEQ ID NO: 120) and M13 Reverse primers (5' CAGGAAACAGCTATGACC 3') (SEQ ID NO: 121) by Beckman Genomics (Danvers, Mass.), using standard dideoxy DNA sequencing methods to identify the sequence of the variable region sequences. The sequences were analyzed using VECTOR NTI® software (Invitrogen) and the IMGT/V-Quest web server (imgt.cines.fr) to identify and confirm variable region sequences.

The nucleic acid sequences encoding and the protein sequences defining variable regions of the murine monoclonal antibodies are shown below (amino terminal signal peptide sequences are not shown). CDR sequences (Kabat definition) are indicated by bold font and underlining in the amino acid sequences.

Nucleic Acid Sequence Encoding the Heavy Chain Variable Region of the 07F01 Antibody (SEQ ID NO: 1)

```
  1 gaggtgaagc ttctcgagtc tggaggtggc ctggtgcagc cgggtggatc cctgaaactc

 61 tcctgtgcag cctcaggatt cgattttagt agacactgga tgagttgggt ccggctggct

121 ccagggaaag ggctagaatg gatcgcagaa attaatccag atagcagaac gataaactat

181 acgccatctc taaaggagaa attcatcatc tccagagaca acgccaaaaa ttcgctgttt

241 ctgcaaatga acagagtgag atctgaggac acagcccttt attactgtgc aagacgggta

301 agaattcatt actacggcgc tatggactgc tggggtcaag gaacctcagt caccgtctcc

361 tca
```

Protein Sequence Defining the Heavy Chain Variable Region of the 07F01 Antibody (SEQ ID NO: 2)

1 evkllesggg lvqpggslkl scaasgfdfs <u>rhwms</u>wvrla pgkglewia<u>e</u> <u>inpdsrtiny</u>

61 <u>tpslke</u>kfii srdnaknslf lqmnrvrsed talyycar<u>rv</u> <u>rihyygamdc</u> wgqgtsvtvs 121 s -continued Nucleic Acid Sequence Encoding the Kappa Chain Variable Region of the 07F01 Antibody (SEQ ID NO: 3)

1gacattgtgt tgacccagtc tcaaaaaatc gtgtccacat cagtaggagc cagggtcagc

61gtcacctgca aggccagtca gaatgtgggt tctagtttag tctggtatca acagaaacca

121ggtcaatctc ctaaaacact gatttactcg gcatccttcc ggtacagtgg agtccctgat

181cgcttcacag gcagtggatc tgggacagat ttcactctca ccatcagcaa tgtgcagtct

241gaagacttgg cagattattt ctgtcaacaa tataataact atccgctcac gttcggtgct

301gggaccaagc tggagctgaa a

Protein Sequence Defining the Kappa Chain Variable Region of the 07F01 Antibody (SEQ ID NO: 4)

1divltqsqki vstsvgarvs vtckasqnvg sslvwyqqkp gqspktliys asfrysgvpd 61rftgsgsgtd ftltisnvqs edladyfcqq ynnypltfga gtklelk Nucleic Acid Sequence Encoding the Heavy Chain Variable Region of the 12B11 Antibody (SEQ ID NO: 11)

1gaggtgcagt tagtggagtc tgggggaggc ttagtgaagc ctggagggtc cctgaaactc

61tcctgtgcag cctctggatt cactttcagt acctatgcca tgtcttggat tcgccagact

121ccggagaaga ggctggagtg ggtcgcagga atcactaatg gtggtagttt cacctactat

181ccagacactg tgaagggacg attcaccatc tccagagaca atgccaggaa catcctatac

241ctgcaaatga gcggtctgag gtctgaggac acggccatgt attattgtgc aagacagggt

301tactatggtg ttaactttga ctactggggc caaggcacca ctctcacagt ctcctca

Protein Sequence Defining the Heavy Chain Variable Region of the 12B11 Antibody (SEQ ID NO: 12)

1evqlvesggg lvkpggslkl scaasgftfs tyamswirqt pekrlewvag itnggsftyy

61pdtvkgrfti srdnarnily lqmsglrsed tamyycargg yygvnfdywg qgttltvss

Nucleic Acid Sequence Encoding the Kappa Chain Variable Region of the 12B11 Antibody (SEQ ID NO: 13)

1gatgctgtga tgacccaaac tccactctcc ctgcctgtca gtcttggaga tcaagcctcc

61atctcttgca ggtctagtca gagccttgaa aacagtaacg gaaacactta tttgaactgg

121tacctccaga aaccaggcca gtctccacag ctcctgatct acagggtttc caaccgattt

181tctggggtcc cagacaggtt cagtggtagt ggatcaggga cagatttcac actgaaaatc

241atcagagtgg aggctgagga tttgggactt tatttctgcc tccaagttac acatgtcccg

301cacacgttcg gaggggggac caaactggaa ttaaaa

Protein Sequence Defining the Kappa Chain Variable Region of the 12B11 Antibody (SEQ ID NO: 14)

1davmtqtpls lpvslgdqas iscrssqsle nsngntylnw ylqkpgqspq lliyrvsnrf

61sgvpdrfsgs gsgtdftlki irveaedlgl yfclqvthvp htfgggtkle lk

Nucleic Acid Sequence Encoding the Heavy Chain Variable Region of the 17F06 Antibody (SEQ ID NO: 21)

1gaagtgaagc tggtggagtc ggggggaggc ttagtgaagc ctggagcgtc tctgaaactc

61tcctgtgcag cctctggatt cattttcagt tcctatggca tgtcttgggt tcgccagact

121tcagacaaga ggctggagtg ggtcgcttcc attagtagtg gtggtggtac cacctactat

181ctagacactg taaagggccg attcaccatc tccagagaga atgccaagga caccctgtac

241ctgcaaatga gtggtctgaa gtctgaagac acggccttgt attactgtac aagaggccaa

301tggttactaa agtttgctta ctggggccaa gggactctgg tcactgtctc tgca

-continued

Protein Sequence Defining the Heavy Chain Variable Region of the 17F06 Antibody (SEQ ID NO: 22)

1 evklvesggg lvkpgaslkl scaasgfifs sygmswvrqt sdkrlewvas issgggttyy

61 ldtvkgrfti srenakdtly lqmsglksed talyyctrgq wllkfaywgq gtlvtvsa

Nucleic Acid Sequence Encoding the Lambda Chain Variable Region of the 17F06 Antibody (SEQ ID NO: 23)

1 caacttgtgc tcactcagtc atcttcagcc tctttctccc tgggagcctc agcaaaactc 61 acgtgcacct tgagtagtca gcacactacg tacaccattg aatggtatca gcaactgcca 121 ctcaagcctc ctaagtatgt gatggagctt aagaaagatg gaagccacag cacaggtgtt 181 gggattcctg atcgcttctc tggatccagc tctggtgctg atcgctacct taccatttcc 241 aacatccagc ctgaagatga agcaatatac atctgtggtg tgggtgagac aattgaggac 301 caatttgtgt atgttttcgg cggtggcacc aaggtcactg tccta Protein Sequence Defining the Lambda Chain Variable Region of the 17F06 Antibody (SEQ ID NO: 24)

1 qlvltqsssa sfslgasakl tctlssqhtt ytiewyqqlp lkppkyvmel kkdgshstgv

61 gipdrfsgss sgadryltis niqpedeaiy icgvgetied qfvyvfgggt kvtvl

Nucleic Acid Sequence Encoding the Heavy Chain Variable Region of the 18H09 Antibody (SEQ ID NO: 31)

1 gaggtgcagc ttcaggagtc aggacctagc ctcgtgaaac cttctcagac tctgtccctc 61 acctgttatg tcactggcga ctccatcacc agtgattact ggaattggat ccggaaattc 121 ccaggaaata aacttgagta catgggatat atcagctaca gtggtagcac ttactacaat 181 ccatctctca aaagtcgaat ctccatcact cgagacacat ccaagaacca gttctacctt 241 cggttgaatt ctgtgactac tgaggacaca gccacatatt actgtgcaag aacccatata 301 cttacgattg cttactgggg ccaagggact ctggtcactg tctctgca Protein Sequence Defining the Heavy Chain Variable Region of the 18H09 Antibody (SEQ ID NO: 32)

1 evqlqesgps lvkpsqtlsl tcyvtgdsit sdywnwirkf pgnkleymgy isysgstyyn

61 pslksrisit rdtsknqfyl rlnsvttedt atyycarthi ltiaywgqgt lvtvsa

Nucleic Acid Sequence Encoding the Lambda Chain Variable Region of the 18H09 Antibody (SEQ ID NO: 33)

1 caggctgttg tgactcagga atctgcactc accacatcac ctggtgaaac agtcacactc 61 acttgtcgct caagtgccgg ggctgttaca actagtaact ttgccaactg ggtccaagaa 121 aaaccagatc atttattcac tggtctaata ggtgatacca acatccgagc tccaggtgtt 181 cctgccagat tctcaggctc cctgattgga gacaaggctg ccctcaccat cacaggggca 241 cagactgagg atgaggcaat atatttctgt gctctttggt acagcaacca ttactgggtg 301 ttcggtggag gaaccaaact gactgtccta Protein Sequence Defining the Lambda Chain Variable Region of the 18H09 Antibody (SEQ ID NO: 34)

1 qavvtqesal ttspgetvtl tcrssagavt tsnfanwvqe kpdhlftgli gdtnirapgv 61 parfsgslig dkaaltitga qtedeaiyfc alwysnhywv fgggtkltvl Nucleic Acid Sequence Encoding the Heavy Chain Variable Region of the 29B06 Antibody (SEQ ID NO: 41)

1 gaggtgcagc ttcaggagtc aggacctagc ctcgtgaaac cttctcagac tctgtccctc 61 acctgttctg tcactggcga ctccatcacc agtggttact ggaactggat ccggaaattc 121 ccagggaata aacttgagta catggggtac ataagctaca gtggtaaaac ttactacaat -continued

```
181ccatctctca aaagtcgaat ctccatcact cgagacacat ccaagaacca ttactacctg

241cagttgattt ctgtgactgc tgaggacaca gccacatatt actgtgcaag gtctaagtac

301gactatgcta tggactactg gggtcaagga acctcagtca ccgtctcctc a
```

Protein Sequence Defining the Heavy Chain Variable Region of the 29B06 Antibody (SEQ ID NO: 42)

```
  1evqlqesgps lvkpsqtlsl tcsvtgdsit sgywnwirkf pgnkleymgy isysgktyyn

 61pslksrisit rdtsknhyyl qlisvtaedt atyycarsky dyamdywgqg tsvtvss
```

Nucleic Acid Sequence Encoding the Kappa Chain Variable Region of the 29B06 Antibody (SEQ ID NO: 43)

```
  1gacattgtgc tgacccaatc tccagcttct ttggctgtgt ctctaggaca gagggccacc

 61atctcctgca gagccagcga aattgttgat aattttggca ttagttttat gaactggttc

121caacagaaac caggacagcc acccaaactc ctcatctatg ctgcatccaa ccaaggatcc

181ggggtccctg ccaggtttag tggcagtggg tctgggacag acttcagcct caacatccat

241cctgtggagg aggatgatac tgcaatgtat ttctgtcagc aaagtaagga ggttcctccg

301acgttcggtg gaggcaccaa gctggaaatc aaa
```

Protein Sequence Defining the Kappa Chain Variable Region of the 29B06 Antibody (SEQ ID NO: 44)

```
  1divltqspas lavslgqrat iscraseivd nfgisfmnwf qqkpgqppkl liyaasnqgs

 61gvparfsgsg sgtdfslnih pveeddtamy fcqqskevpp tfgggtklei k
```

The amino acid sequences defining the immunoglobulin heavy chain variable regions for the antibodies produced in Example 2 are aligned in FIG. 2. Amino terminal signal peptide sequences (for expression/secretion) are not shown. $CDR_1$, $CDR_2$, and $CDR_3$ (Kabat definition) are identified by boxes. FIG. 3 shows an alignment of the separate $CDR_1$, $CDR_2$, and $CDR_3$ sequences for each antibody.

The amino acid sequences defining the immunoglobulin light chain variable regions of the antibodies in Example 2 are aligned in FIG. 4. Amino terminal signal peptide sequences (for expression/secretion) are not shown. $CDR_1$, $CDR_2$ and $CDR_3$ are identified by boxes. FIG. 5 shows an alignment of the separate $CDR_1$, $CDR_2$, and $CDR_3$ sequences for each antibody.

Table 1 shows the SEQ ID NO. of each sequence discussed in this Example.

TABLE 1

| SEQ. ID NO. | Nucleic Acid or Protein |
|---|---|
| 1 | 07F01 Heavy Chain Variable Region-nucleic acid |
| 2 | 07F01 Heavy Chain Variable Region-protein |
| 3 | 07F01 Light (kappa) Chain Variable Region-nucleic acid |
| 4 | 07F01 Light (kappa) Chain Variable Region-protein |
| 5 | 07F01 Heavy Chain $CDR_1$ |
| 6 | 07F01 Heavy Chain $CDR_2$ |
| 7 | 07F01 Heavy Chain $CDR_3$ |
| 8 | 07F01 Light (kappa) Chain $CDR_1$ |
| 9 | 07F01 Light (kappa) Chain $CDR_2$ |
| 10 | 07F01 Light (kappa) Chain $CDR_3$ |
| 11 | 12B11 Heavy Chain Variable Region-nucleic acid |
| 12 | 12B11 Heavy Chain Variable Region-protein |
| 13 | 12B11 Light (kappa) Chain Variable Region-nucleic acid |
| 14 | 12B11 Light (kappa) Chain Variable Region-protein |
| 15 | 12B11 Heavy Chain $CDR_1$ |
| 16 | 12B11 Heavy Chain $CDR_2$ |
| 17 | 12B11 Heavy Chain $CDR_3$ |
| 18 | 12B11 Light (kappa) Chain $CDR_1$ |
| 19 | 12B11 Light (kappa) Chain $CDR_2$ |
| 20 | 12B11 Light (kappa) Chain $CDR_3$ |
| 21 | 17F06 Heavy Chain Variable Region-nucleic acid |
| 22 | 17F06 Heavy Chain Variable Region-protein |
| 23 | 17F06 Light (lambda) Chain Variable Region-nucleic acid |
| 24 | 17F06 Light (lambda) Chain Variable Region-protein |
| 25 | 17F06 Heavy Chain $CDR_1$ |
| 26 | 17F06 Heavy Chain $CDR_2$ |
| 27 | 17F06 Heavy Chain $CDR_3$ |
| 28 | 17F06 Light (lambda) Chain $CDR_1$ |
| 29 | 17F06 Light (lambda) Chain $CDR_2$ |
| 30 | 17F06 Light (lambda) Chain $CDR_3$ |
| 31 | 18H09 Heavy Chain Variable Region-nucleic acid |
| 32 | 18H09 Heavy Chain Variable Region-protein |
| 33 | 18H09 Light (lambda) Chain Variable Region-nucleic acid |
| 34 | 18H09 Light (lambda) Chain Variable Region-protein |
| 35 | 18H09 Heavy Chain $CDR_1$ |
| 36 | 18H09 Heavy Chain $CDR_2$ |
| 37 | 18H09 Heavy Chain $CDR_3$ |
| 38 | 18H09 Light (lambda) Chain $CDR_1$ |
| 39 | 18H09 Light (lambda) Chain $CDR_2$ |
| 40 | 18H09 Light (lambda) Chain $CDR_3$ |
| 41 | 29B06 Heavy Chain Variable Region-nucleic acid |
| 42 | 29B06 Heavy Chain Variable Region-protein |
| 43 | 29B06 Light (kappa) Chain Variable Region-nucleic acid |
| 44 | 29B06 Light (kappa) Chain Variable Region-protein |
| 45 | 29B06 Heavy Chain $CDR_1$ |
| 46 | 29B06 Heavy Chain $CDR_2$ |
| 47 | 29B06 Heavy Chain $CDR_3$ |
| 48 | 29B06 Light (kappa) Chain $CDR_1$ |
| 49 | 29B06 Light (kappa) Chain $CDR_2$ |
| 50 | 29B06 Light (kappa) Chain $CDR_3$ |

Mouse monoclonal antibody heavy chain CDR sequences (Kabat, Chothia, and IMGT definitions) are shown in Table 2.

TABLE 2

| | CDR1 | CDR2 | CDR3 |
|---|---|---|---|
| | | Kabat | |
| 07F01 | RHWMS (SEQ ID NO: 5) | EINPDSRTINYTPSLKE (SEQ ID NO: 6) | RVRIHYYGAMDC (SEQ ID NO: 7) |
| 12B11 | TYAMS (SEQ ID NO: 15) | GITNGGSFTYYPDTVKG (SEQ ID NO: 16) | QGYYGVNFDY (SEQ ID NO: 17) |
| 17F06 | SYGMS (SEQ ID NO: 25) | SISSGGGTTYYLDTVKG (SEQ ID NO: 26) | GQWLLKFAY (SEQ ID NO: 27) |
| 18H09 | SDYWN (SEQ ID NO: 35) | YISYSGSTYYNPSLK (SEQ ID NO: 36) | THILTIAY (SEQ ID NO: 37) |
| 29B06 | SGYWN (SEQ ID NO: 45) | YISYSGKTYYNPSLKS (SEQ ID NO: 46) | SKYDYAMDY (SEQ ID NO: 47) |
| | | Chothia | |
| 07F01 | GFDFSRH (SEQ ID NO: 51) | NPDSRT (SEQ ID NO: 52) | RVRIHYYGAMDC (SEQ ID NO: 7) |
| 12B11 | GFTFSTY (SEQ ID NO: 53) | TNGGSF (SEQ ID NO: 54) | QGYYGVNFDY (SEQ ID NO: 17) |
| 17F06 | GFIFSSY (SEQ ID NO: 55) | SSGGGT (SEQ ID NO: 56) | GQWLLKFAY (SEQ ID NO: 27) |
| 18H09 | GDSITSD (SEQ ID NO: 57) | SYSGS (SEQ ID NO: 58) | THILTIAY (SEQ ID NO: 37) |
| 29B06 | GDSITSG (SEQ ID NO: 59) | SYSGK (SEQ ID NO: 60) | SKYDYAMDY (SEQ ID NO: 47) |
| | | IMGT | |
| 07F01 | GFDFSRHW (SEQ ID NO: 61) | INPDSRTI (SEQ ID NO: 62) | ARRVRIHYYGAMDC (SEQ ID NO: 63) |
| 12B11 | GFTFSTYA (SEQ ID NO: 64) | ITNGGSFT (SEQ ID NO: 65) | ARQGYYGVNFDY (SEQ ID NO: 66) |
| 17F06 | GFIFSSYG (SEQ ID NO: 67) | ISSGGGTT (SEQ ID NO: 68) | TRGQWLLKFAY (SEQ ID NO: 69) |
| 18H09 | GDSITSDY (SEQ ID NO: 70) | ISYSGST (SEQ ID NO: 71) | ARTHILTIAY (SEQ ID NO: 72) |

TABLE 2-continued

| | CDR1 | CDR2 | CDR3 |
|---|---|---|---|
| 29B06 | GDSITSGY (SEQ ID NO: 73) | ISYSGKT (SEQ ID NO: 74) | ARSKYDYAMDY (SEQ ID NO: 75) |

Mouse monoclonal antibody Kappa light chain CDR sequences (Kabat, Chothia, and IMGT definitions) are shown in Table 3.

TABLE 3

| | CDR1 | CDR2 | CDR3 |
|---|---|---|---|
| | | Kabat/Chothia | |
| 07F01 | KASQNVGSSLV (SEQ ID NO: 8) | SASFRYS (SEQ ID NO: 9) | QQYNNYPLT (SEQ ID NO: 10) |
| 12B11 | RSSQSLENSNGNTYLN (SEQ ID NO: 18) | RVSNRFS (SEQ ID NO: 19) | LQVTHVPHT (SEQ ID NO: 20) |
| 17F06 | TLSSQHTTYTIE (SEQ ID NO: 28) | LKKDGSHSTGV (SEQ ID NO: 29) | GVGETIEDQFVYV (SEQ ID NO: 30) |
| 18H09 | RSSAGAVTTSNFAN (SEQ ID NO: 38) | DTNIRAP (SEQ ID NO: 39) | ALWYSNHYWV (SEQ ID NO: 40) |
| 29B06 | RASEIVDNFGISFMN (SEQ ID NO: 48) | AASNQGS (SEQ ID NO: 49) | QQSKEVPPT (SEQ ID NO: 50) |
| | | IMGT | |
| 07F01 | QNVGSS (SEQ ID NO: 76) | SAS | QQYNNYPLT (SEQ ID NO: 10) |
| 12B11 | QSLENSNGNTY (SEQ ID NO: 77) | RVS | LQVTHVPHT (SEQ ID NO: 20) |
| 17F06 | SQHTTYT (SEQ ID NO: 78) | LKKDGSH (SEQ ID NO: 79) | GVGETIEDQFVYV (SEQ ID NO: 30) |
| 18H09 | AGAVTTSNF (SEQ ID NO: 80) | DTN | ALWYSNHYWV (SEQ ID NO: 40) |
| 29B06 | EIVDNFGISF (SEQ ID NO: 81) | AAS | QQSKEVPPT (SEQ ID NO: 50) |

To create the complete heavy or kappa chain antibody sequences, each variable sequence above is combined with its respective constant region. For example, a complete heavy chain comprises a heavy variable sequence followed by the murine IgG1 or IgG2a heavy chain constant sequence, a complete kappa chain comprises a kappa variable sequence followed by the murine kappa light chain constant sequence, and a complete lambda chain comprises a lambda variable sequence followed by the murine lambda IGLC1 or IGLC2 light chain constant sequence.

Nucleic Acid Sequence Encoding the Murine IgG1 Heavy Chain Constant Region (SEQ ID NO: 82)

```
  1 gccaaaacga cacccccatc tgtctatcca ctggcccctg gatctgctgc ccaaactaac

 61 tccatggtga ccctgggatg cctggtcaag ggctatttcc ctgagccagt gacagtgacc

121 tggaactctg gatccctgtc cagcggtgtg cacaccttcc cagctgtcct gcagtctgac
```

-continued

```
181 ctctacactc tgagcagctc agtgactgtc cctccagca cctggcccag cgagaccgtc

241 acctgcaacg ttgcccaccc ggccagcagc accaaggtgg acaagaaaat tgtgcccagg

301 gattgtggtt gtaagccttg catatgtaca gtcccagaag tatcatctgt cttcatcttc

361 cccccaaagc ccaaggatgt gctcaccatt actctgactc ctaaggtcac gtgtgttgtg

421 gtagacatca gcaaggatga tcccgaggtc cagttcagct ggtttgtaga tgatgtggag

481 gtgcacacag ctcagacgca accccgggag gagcagttca acagcacttt ccgctcagtc

541 agtgaacttc ccatcatgca ccaggactgg ctcaatggca aggagttcaa atgcagggtc

601 aacagtgcag ctttccctgc ccccatcgag aaaaccatct ccaaaaccaa aggcagaccg

661 aaggctccac aggtgtacac cattccacct cccaaggagc agatggccaa ggataaagtc

721 agtctgacct gcatgataac agacttcttc cctgaagaca ttactgtgga gtggcagtgg

781 aatgggcagc cagcggagaa ctacaagaac actcagccca tcatggacac agatggctct

841 tacttcgtct acagcaagct caatgtgcag aagagcaact gggaggcagg aaatactttc

901 acctgctctg tgttacatga gggcctgcac aaccaccata ctgagaagag cctctcccac

961 tctcctggta aa
```

Protein Sequence Defining the Murine IgG1 Heavy Chain Constant Region (SEQ ID NO: 83)

```
  1 akttppsvyp lapgsaaqtn smvtlgclvk gyfpepvtvt wnsgslssgv htfpavlqsd

 61 lytlsssvtv psstwpsetv tcnvahpass tkvdkkivpr dcgckpcict vpevssvfif

121 ppkpkdvlti tltpkvtcvv vdiskddpev qfswfvddve vhtaqtqpre eqfnstfrsv

181 selpimhqdw lngkefkcrv nsaafpapie ktisktkgrp kapqvytipp pkeqmakdkv

241 sltcmitdff peditvewqw ngqpaenykn tqpimdtdgs yfvysklnvq ksnweagntf

301 tcsvlheglh nhhtekslsh spgk
```

Nucleic Acid Sequence Encoding the Murine IgG2a Heavy Chain Constant Region (SEQ ID NO: 84)

```
  1 gccaaaacaa cagccccatc ggtctatcca ctggcccctg tgtgtggaga tacaactggc

 61 tcctcggtga ctctaggatg cctggtcaag ggttatttcc ctgagccagt gaccttgacc

121 tggaactctg gatccctgtc cagtggtgtg cacaccttcc cagctgtcct gcagtctgac

181 ctctacaccc tcagcagctc agtgactgta acctcgagca cctggcccag ccagtccatc

241 acctgcaatg tggcccaccc ggcaagcagc accaaggtgg acaagaaaat tgagcccaga

301 gggcccacaa tcaagccctg tcctccatgc aaatgcccag cacctaacct cttgggtgga

361 ccatccgtct tcatcttccc tccaaagatc aaggatgtac tcatgatctc cctgagcccc

421 atagtcacat gtgtggtggt ggatgtgagc gaggatgacc cagatgtcca gatcagctgg

481 tttgtgaaca acgtggaagt acacacagct cagacacaaa cccatagaga ggattacaac

541 agtactctcc gggtggtcag tgccctcccc atccagcacc aggactggat gagtggcaag

601 gagttcaaat gcaaggtcaa caacaaagac ctcccagcgc ccatcgagag aaccatctca

661 aaacccaaag ggtcagtaag agctccacag gtatatgtct tgcctccacc agaagaagag

721 atgactaaga aacaggtcac tctgacctgc atggtcacag acttcatgcc tgaagacatt

781 tacgtggagt ggaccaacaa cgggaaaaca gagctaaact acaagaacac tgaaccagtc

841 ctggactctg atggttctta cttcatgtac agcaagctga gagtggaaaa gaagaactgg

901 gtggaaagaa atagctactc ctgttcagtg gtccacgagg gtctgcacaa tcaccacacg

961 actaagagct tctcccggac tccgggtaaa
```

Protein Sequence Defining the Murine IgG2a Heavy Chain Constant Region

-continued (SEQ ID NO: 85)

```
  1 akttapsvyp lapvcgdttg ssvtlgclvk gyfpepvtlt wnsgslssgv htfpavlqsd

 61 lytlsssvtv tsstwpsqsi tcnvahpass tkvdkkiepr gptikpcppc kcpapnllgg

121 psvfifppki kdvlmislsp ivtcvvvdvs eddpdvqisw fvnnvevhta qtqthredyn

181 stlrvvsalp iqhqdwmsgk efkckvnnkd lpapiertis kpkgsvrapq vyvlpppeee

241 mtkkqvtltc mvtdfmpedi yvewtnngkt elnykntepv ldsdgsyfmy sklrvekknw

301 vernsyscsv vheglhnhht tksfsrtpgk
```

Nucleic Acid Sequence Encoding the Murine Kappa Light Chain Constant Region (SEQ ID NO: 86)

```
  1 cgggctgatg ctgcaccaac tgtatccatc ttcccaccat ccagtgagca gttaacatct

 61 ggaggtgcct cagtcgtgtg cttcttgaac aacttctacc ccaaagacat caatgtcaag

121 tggaagattg atggcagtga acgacaaaat ggcgtcctga acagttggac tgatcaggac

181 agcaaagaca gcacctacag catgagcagc accctcacgt tgaccaagga cgagtatgaa

241 cgacataaca gctatacctg tgaggccact cacaagacat caacttcacc cattgtcaag

301 agcttcaaca ggaatgagtg t
```

Protein Sequence Defining the Murine Kappa Light Chain Constant Region (SEQ ID NO: 87)

```
  1 radaaptvsi fppsseqlts ggasvvcfln nfypkdinvk wkidgserqn gvlnswtdqd

 61 skdstysmss tltltkdeye rhnsytceat hktstspivk sfnrnec
```

Nucleic Acid Sequence Encoding the Murine Lambda (IGLC1) Light Chain Constant Region (SEQ ID NO: 88)

```
  1 ggccagccca agtcttcgcc atcagtcacc ctgtttccac cttcctctga agagctcgag

 61 actaacaagg ccacactggt gtgtacgatc actgatttct acccaggtgt ggtgacagtg

121 gactggaagg tagatggtac ccctgtcact cagggtatgg agacaaccca gccttccaaa

181 cagagcaaca acaagtacat ggctagcagc tacctgaccc tgacagcaag agcatgggaa

241 aggcatagca gttacagctg ccaggtcact catgaaggtc acactgtgga gaagagtttg

301 tcccgtgctg actgttcc
```

Protein Sequence Defining the Murine Lambda (IGLC1) Light Chain Constant Region (SEQ ID NO: 89)

```
  1 gqpksspsvt lfppsseele tnkatlvcti tdfypgvvtv dwkvdgtpvt qgmettqpsk

 61 qsnnkymass yltltarawe rhssyscqvt heghtveksl sradcs
```

Nucleic Acid Sequence Encoding the Murine Lambda (IGLC2) Light Chain Constant Region (SEQ ID NO: 90)

```
  1 ggtcagccca agtccactcc cactctcacc gtgtttccac cttcctctga ggagctcaag

 61 gaaaacaaag ccacactggt gtgtctgatt tccaactttt ccccgagtgg tgtgacagtg

121 gcctggaagg caaatggtac acctatcacc cagggtgtgg acacttcaaa tcccaccaaa

181 gagggcaaca agttcatggc cagcagcttc ctacatttga catcggacca gtggagatct

241 cacaacagtt ttacctgtca agttacacat gaaggggaca ctgtggagaa gagtctgtct

301 cctgcagaat gtctc
```

Protein Sequence Defining the Murine Lambda (IGLC2) Light Chain Constant Region (SEQ ID NO: 91)

```
  1 gqpkstptlt vfppsseelk enkatlvcli snfspsgvtv awkangtpit qgvdtsnptk

 61 egnkfmassf lhltsdqwrs hnsftcqvth egdtveksls paecl
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length IgG heavy chain and light chain sequences. It is also contemplated that the variable region sequences can be ligated to other constant region sequences to produce active full length IgG heavy and light chains.

```
Nucleic Acid Sequence Encoding the Full Length Heavy Chain Sequence
(Heavy Chain Variable Region and IgG1 Constant Region) of 07F01
                                                      (SEQ ID NO: 92)
   1 gaggtgaagc ttctcgagtc tggaggtggc ctggtgcagc cgggtggatc cctgaaactc

  61 tcctgtgcag cctcaggatt cgattttagt agacactgga tgagttgggt ccggctggct

 121 ccagggaaag ggctagaatg gatcgcagaa attaatccag atagcagaac gataaactat

 181 acgccatctc taaaggagaa attcatcatc tccagagaca acgccaaaaa ttcgctgttt

 241 ctgcaaatga acagagtgag atctgaggac acagcccttt attactgtgc aagacgggta

 301 agaattcatt actacggcgc tatggactgc tggggtcaag gaacctcagt caccgtctcc

 361 tcagccaaaa cgacaccccc atctgtctat ccactggccc ctggatctgc tgcccaaact

 421 aactccatgg tgaccctggg atgcctggtc aagggctatt tccctgagcc agtgacagtg

 481 acctggaact ctggatccct gtccagcggt gtgcacacct tcccagctgt cctgcagtct

 541 gacctctaca ctctgagcag ctcagtgact gtcccctcca gcacctggcc cagcgagacc

 601 gtcacctgca acgttgccca cccggccagc agcaccaagg tggacaagaa aattgtgccc

 661 agggattgtg gttgtaagcc ttgcatatgt acagtcccag aagtatcatc tgtcttcatc

 721 ttccccccaa agcccaagga tgtgctcacc attactctga ctcctaaggt cacgtgtgtt

 781 gtggtagaca tcagcaagga tgatcccgag gtccagttca gctggtttgt agatgatgtg

 841 gaggtgcaca cagctcagac gcaaccccgg gaggagcagt tcaacagcac tttccgctca

 901 gtcagtgaac ttcccatcat gcaccaggac tggctcaatg gcaaggagtt caaatgcagg

 961 gtcaacagtg cagctttccc tgcccccatc gagaaaacca tctccaaaac caaaggcaga

1021 ccgaaggctc cacaggtgta caccattcca cctcccaagg agcagatggc caaggataaa

1081 gtcagtctga cctgcatgat aacagacttc ttccctgaag acattactgt ggagtggcag

1141 tggaatgggc agccagcgga gaactacaag aacactcagc ccatcatgga cacagatggc

1201 tcttacttcg tctacagcaa gctcaatgtg cagaagagca actgggaggc aggaaatact

1261 ttcacctgct ctgtgttaca tgagggcctg cacaaccacc atactgagaa gagcctctcc

1321 cactctcctg gtaaa
```

```
Protein Sequence Defining the Full Length Heavy Chain Sequence
(Heavy Chain Variable Region and IgG1 Constant Region) of 07F01
                                                      (SEQ ID NO: 93)
   1 evkllesggg lvqpggslkl scaasgfdfs rhwmswvrla pgkglewiae inpdsrtiny

  61 tpslkekfii srdnaknslf lqmnrvrsed talyycarrv rihyygamdc wgqgtsvtvs

 121 sakttppsvy plapgsaaqt nsmvtlgclv kgyfpepvtv twnsgslssg vhtfpavlqs

 181 dlytlsssvt vpsstwpset vtcnvahpas stkvdkkivp rdcgckpcic tvpevssvfi

 241 fppkpkdvlt itltpkvtcv vvdiskddpe vqfswfvddv evhtaqtqpr eeqfnstfrs

 301 vselpimhqd wlngkefkcr vnsaafpapi ektisktkgr pkapqvytip ppkeqmakdk

 361 vsltcmitdf fpeditvewq wngqpaenyk ntqpimdtdg syfvysklnv qksnweagnt

 421 ftcsvlhegl hnhhteksls hspgk
```

```
Nucleic Acid Sequence Encoding the Full Length Light Chain Sequence
(Kappa Chain Variable Region and Constant Region) of 07F01
```

-continued (SEQ ID NO: 94)

```
   1 gacattgtgt tgacccagtc tcaaaaaatc gtgtccacat cagtaggagc cagggtcagc
  61 gtcacctgca aggccagtca gaatgtgggt tctagtttag tctggtatca acagaaacca
 121 ggtcaatctc ctaaaacact gatttactcg gcatccttcc ggtacagtgg agtccctgat
 181 cgcttcacag gcagtggatc tgggacagat ttcactctca ccatcagcaa tgtgcagtct
 241 gaagacttgg cagattattt ctgtcaacaa tataataact atccgctcac gttcggtgct
 301 gggaccaagc tggagctgaa acgggctgat gctgcaccaa ctgtatccat cttcccacca
 361 tccagtgagc agttaacatc tggaggtgcc tcagtcgtgt gcttcttgaa caacttctac
 421 cccaaagaca tcaatgtcaa gtggaagatt gatggcagtg aacgacaaaa tggcgtcctg
 481 aacagttgga ctgatcagga cagcaaagac agcacctaca gcatgagcag caccctcacg
 541 ttgaccaagg acgagtatga acgacataac agctatacct gtgaggccac tcacaagaca
 601 tcaacttcac ccattgtcaa gagcttcaac aggaatgagt gt
```

Protein Sequence Defining the Full Length Light Chain Sequence (Kappa Chain Variable Region and Constant Region) of 07F01

(SEQ ID NO: 95)

```
   1 divltqsqki vstsvgarvs vtckasqnvg sslvwyqqkp gqspktliys asfrysgvpd
  61 rftgsgsgtd ftltisnvqs edladyfcqq ynnypltfga gtklelkrad aaptvsifpp
 121 sseqltsgga svvcflnnfy pkdinvkwki dgserqngvl nswtdqdskd stysmsstlt
 181 ltkdeyerhn sytceathkt stspivksfn rnec
```

Nucleic Acid Sequence Encoding the Full Length Heavy Chain Sequence (Heavy Chain Variable Region and IgG1 Constant Region) of 12B11

(SEQ ID NO: 96)

```
   1 gaggtgcagt tagtggagtc tgggggaggc ttagtgaagc ctggagggtc cctgaaactc
  61 tcctgtgcag cctctggatt cactttcagt acctatgcca tgtcttggat tcgccagact
 121 ccggagaaga ggctggagtg ggtcgcagga atcactaatg gtggtagttt cacctactat
 181 ccagacactg tgaagggacg attcaccatc tccagagaca atgccaggaa catcctatac
 241 ctgcaaatga gcggtctgag gtctgaggac acggccatgt attattgtgc aagacagggt
 301 tactatggtg ttaactttga ctactggggc caaggcacca ctctcacagt ctcctcagcc
 361 aaaacgacac ccccatctgt ctatccactg gcccctggat ctgctgccca aactaactcc
 421 atggtgaccc tgggatgcct ggtcaagggc tatttccctg agccagtgac agtgacctgg
 481 aactctggat ccctgtccag cggtgtgcac accttcccag ctgtcctgca gtctgacctc
 541 tacactctga gcagctcagt gactgtcccc tccagcacct ggcccagcga gaccgtcacc
 601 tgcaacgttg cccacccggc cagcagcacc aaggtggaca agaaaattgt gcccagggat
 661 tgtggttgta agccttgcat atgtacagtc ccagaagtat catctgtctt catcttcccc
 721 ccaaagccca aggatgtgct caccattact ctgactccta aggtcacgtg tgttgtggta
 781 gacatcagca aggatgatcc cgaggtccag ttcagctggt ttgtagatga tgtggaggtg
 841 cacacagctc agacgcaacc ccgggaggag cagttcaaca gcactttccg ctcagtcagt
 901 gaacttccca tcatgcacca ggactggctc aatggcaagg agttcaaatg cagggtcaac
 961 agtgcagctt tccctgcccc catcgagaaa accatctcca aaaccaaagg cagaccgaag
1021 gctccacagg tgtacaccat tccacctccc aaggagcaga tggccaagga taaagtcagt
1081 ctgacctgca tgataacaga cttcttccct gaagacatta ctgtggagtg gcagtggaat
1141 gggcagccag cggagaacta caagaacact cagcccatca tggacacaga tggctcttac
1201 ttcgtctaca gcaagctcaa tgtgcagaag agcaactggg aggcaggaaa tactttcacc
1261 tgctctgtgt tacatgaggg cctgcacaac caccatactg agaagagcct ctcccactct
```

-continued

```
1321 cctggtaaa
```

Protein Sequence Defining the Full Length Heavy Chain Sequence (Heavy Chain Variable Region and IgG1 Constant Region) of 12B11

(SEQ ID NO: 97)

```
   1 evqlvesggg lvkpggslkl scaasgftfs tyamswirqt pekrlewvag itnggsftyy
  61 pdtvkgrfti srdnarnily lqmsglrsed tamyycarqg yygvnfdywg qgttltvssa
 121 kttppsvypl apgsaaqtns mvtlgclvkg yfpepvtvtw nsgslssgvh tfpavlqsdl
 181 ytlsssvtvp sstwpsetvt cnvahpasst kvdkkivprd cgckpcictv pevssvfifp
 241 pkpkdvltit ltpkvtcvvv diskddpevq fswfvddvev htaqtqpree qfnstfrsvs
 301 elpimhqdwl ngkefkcrvn saafpapiek tisktkgrpk apqvytippp keqmakdkvs
 361 ltcmitdffp editvewqwn gqpaenyknt qpimdtdgsy fvysklnvqk snweagntft
 421 csvlheglhn hhtekslshs pgk
```

Nucleic Acid Sequence Encoding the Full Length Light Chain Sequence (Kappa Chain Variable Region and Constant Region) of 12B11

(SEQ ID NO: 98)

```
   1 gatgctgtga tgacccaaac tccactctcc ctgcctgtca gtcttggaga tcaagcctcc
  61 atctcttgca ggtctagtca gagccttgaa aacagtaacg gaaacactta tttgaactgg
 121 tacctccaga aaccaggcca gtctccacag ctcctgatct acagggtttc caaccgattt
 181 tctggggtcc cagacaggtt cagtggtagt ggatcaggga cagatttcac actgaaaatc
 241 atcagagtgg aggctgagga tttgggactt tatttctgcc tccaagttac acatgtcccg
 301 cacacgttcg gaggggggac caaactggaa ttaaaacggg ctgatgctgc accaactgta
 361 tccatcttcc caccatccag tgagcagtta acatctggag gtgcctcagt cgtgtgcttc
 421 ttgaacaact tctaccccaa agacatcaat gtcaagtgga agattgatgg cagtgaacga
 481 caaaatggcg tcctgaacag ttggactgat caggacagca aagacagcac ctacagcatg
 541 agcagcaccc tcacgttgac caaggacgag tatgaacgac ataacagcta tacctgtgag
 601 gccactcaca agacatcaac ttcacccatt gtcaagagct tcaacaggaa tgagtgt
```

Protein Sequence Defining the Full Length Light Chain Sequence (Kappa Chain Variable Region and Constant Region) of 12B11

(SEQ ID NO: 99)

```
   1 davmtqtpls lpvslgdqas iscrsssqsle nsngntylnw ylqkpgqspq lliyrvsnrf
  61 sgvpdrfsgs gsgtdftlki irveaedlgl yfclqvthvp htfgggtkle lkradaaptv
 121 sifppsseql tsggasvvcf lnnfypkdin vkwkidgser qngvlnswtd qdskdstysm
 181 sstltltkde yerhnsytce athktstspi vksfnrnec
```

Nucleic Acid Sequence Encoding the Full Length Heavy Chain Sequence (Heavy Chain Variable Region and IgG2A Constant Region) of 17F06

(SEQ ID NO: 100)

```
   1 gaagtgaagc tggtggagtc ggggggaggc ttagtgaagc ctggagcgtc tctgaaactc
  61 tcctgtgcag cctctggatt cattttcagt tcctatggca tgtcttgggt tcgccagact
 121 tcagacaaga ggctggagtg ggtcgcttcc attagtagtg gtggtggtac cacctactat
 181 ctagacactg taaagggccg attcaccatc tccagagaga atgccaagga caccctgtac
 241 ctgcaaatga gtggtctgaa gtctgaagac acggccttgt attactgtac aagaggccaa
 301 tggttactaa agtttgctta ctggggccaa gggactctgg tcactgtctc tgcagccaaa
 361 acaacagccc catcggtcta tccactggcc cctgtgtgtg gagatacaac tggctcctcg
 421 gtgactctag gatgcctggt caagggttat ttccctgagc cagtgacctt gacctggaac
 481 tctggatccc tgtccagtgg tgtgcacacc ttcccagctg tcctgcagtc tgacctctac
 541 accctcagca gctcagtgac tgtaacctcg agcacctggc ccagccagtc catcacctgc
 601 aatgtggccc acccggcaag cagcaccaag gtggacaaga aaattgagcc cagagggccc
```

-continued

```
661 acaatcaagc cctgtcctcc atgcaaatgc ccagcaccta acctcttggg tggaccatcc

721 gtcttcatct tccctccaaa gatcaaggat gtactcatga tctccctgag ccccatagtc

781 acatgtgtgg tggtggatgt gagcgaggat gacccagatg tccagatcag ctggtttgtg

841 aacaacgtgg aagtacacac agctcagaca caaacccata gagaggatta caacagtact

901 ctccgggtgg tcagtgccct ccccatccag caccaggact ggatgagtgg caaggagttc

961 aaatgcaagg tcaacaacaa agacctccca gcgcccatcg agagaaccat ctcaaaaccc

1021 aaagggtcag taagagctcc acaggtatat gtcttgcctc caccagaaga agagatgact

1081 aagaaacagg tcactctgac ctgcatggtc acagacttca tgcctgaaga catttacgtg

1141 gagtggacca acaacgggaa aacagagcta aactacaaga acactgaacc agtcctggac

1201 tctgatggtt cttacttcat gtacagcaag ctgagagtgg aaaagaagaa ctgggtggaa

1261 agaaatagct actcctgttc agtggtccac gagggtctgc acaatcacca cacgactaag

1321 agcttctccc ggactccggg taaa
```

Protein Sequence Defining the Full Length Heavy Chain Sequence (Heavy Chain Variable Region and IgG2A Constant Region) of 17F06

(SEQ ID NO: 101)

```
  1 evklvesggg lvkpgaslkl scaasgfifs sygmswvrqt sdkrlewvas issgggttyy

 61 ldtvkgrfti srenakdtly lqmsglksed talyyctrgq wllkfaywgq gtlvtvsaak

121 ttapsvypla pvcgdttgss vtlgclvkgy fpepvtltwn sgslssgvht fpavlqsdly

181 tlsssvtvts stwpsqsitc nvahpasstk vdkkieprgp tikpcppckc papnllggps

241 vfifppkikd vlmislspiv tcvvvdvsed dpdvqiswfv nnvevhtaqt qthredynst

301 lrvvsalpiq hqdwmsgkef kckvnnkdlp apiertiskp kgsvrapqvy vlpppeeemt

361 kkqvtltcmv tdfmpediyv ewtnngktel nykntepvld sdgsyfmysk lrvekknwve

421 rnsyscsvvh eglhnhhttk sfsrtpgk
```

Nucleic Acid Sequence Encoding the Full Length Light Chain Sequence (Lambda Chain Variable Region and Constant Region (IGLC2)) of 17F06

(SEQ ID NO: 102)

```
  1 caacttgtgc tcactcagtc atcttcagcc tctttctccc tgggagcctc agcaaaactc

 61 acgtgcacct tgagtagtca gcacactacg tacaccattg aatggtatca gcaactgcca

121 ctcaagcctc ctaagtatgt gatggagctt aagaaagatg gaagccacag cacaggtgtt

181 gggattcctg atcgcttctc tggatccagc tctggtgctg atcgctacct taccatttcc

241 aacatccagc ctgaagatga agcaatatac atctgtggtg tgggtgagac aattgaggac

301 caatttgtgt atgttttcgg cggtggcacc aaggtcactg tcctaggtca gcccaagtcc

361 actcccactc tcaccgtgtt tccaccttcc tctgaggagc tcaaggaaaa caaagccaca

421 ctggtgtgtc tgatttccaa cttttccccg agtggtgtga cagtggcctg gaaggcaaat

481 ggtacaccta tcacccaggg tgtggacact tcaaatccca ccaaagaggg caacaagttc

541 atggccagca gcttcctaca tttgacatcg gaccagtgga gatctcacaa cagttttacc

601 tgtcaagtta cacatgaagg ggacactgtg gagaagagtc tgtctcctgc agaatgtctc
```

Protein Sequence Defining the Full Length Light Chain Sequence (Lambda Chain Variable Region and Constant Region (IGLC2)) of 17F06

(SEQ ID NO: 103)

```
  1 qlvltqsssa sfslgasakl tctlssqhtt ytiewyqqlp lkppkyvmel kkdgshstgv

 61 gipdrfsgss sgadryltis niqpedeaiy icgvgetied qfvyvfgggt kvtvlgqpks

121 tptltvfpps seelkenkat lvclisnfsp sgvtvawkan gtpitqgvdt snptkegnkf

181 massflhlts dqwrshnsft cqvthegdtv ekslspaecl
```

Nucleic Acid Sequence Encoding the Full Length Heavy Chain Sequence

-continued (Heavy Chain Variable Region and IgG1 Constant Region) of 18H09

(SEQ ID NO: 104)

```
   1 gaggtgcagc ttcaggagtc aggacctagc ctcgtgaaac cttctcagac tctgtccctc
  61 acctgttatg tcactggcga ctccatcacc agtgattact ggaattggat ccggaaattc
 121 ccaggaaata aacttgagta catgggatat atcagctaca gtggtagcac ttactacaat
 181 ccatctctca aaagtcgaat ctccatcact cgagacacat ccaagaacca gttctacctt
 241 cggttgaatt ctgtgactac tgaggacaca gccacatatt actgtgcaag aacccatata
 301 cttacgattg cttactgggg ccaagggact ctggtcactg tctctgcagc caaaacgaca
 361 cccccatctg tctatccact ggcccctgga tctgctgccc aaactaactc catggtgacc
 421 ctgggatgcc tggtcaaggg ctatttccct gagccagtga cagtgacctg gaactctgga
 481 tccctgtcca gcggtgtgca caccttccca gctgtcctgc agtctgacct ctacactctg
 541 agcagctcag tgactgtccc ctccagcacc tggcccagcg agaccgtcac ctgcaacgtt
 601 gcccacccgg ccagcagcac caaggtggac aagaaaattg tgcccaggga ttgtggttgt
 661 aagccttgca tatgtacagt cccagaagta tcatctgtct tcatcttccc cccaaagccc
 721 aaggatgtgc tcaccattac tctgactcct aaggtcacgt gtgttgtggt agacatcagc
 781 aaggatgatc ccgaggtcca gttcagctgg tttgtagatg atgtggaggt gcacacagct
 841 cagacgcaac cccgggagga gcagttcaac agcactttcc gctcagtcag tgaacttccc
 901 atcatgcacc aggactggct caatggcaag gagttcaaat gcagggtcaa cagtgcagct
 961 ttccctgccc ccatcgagaa aaccatctcc aaaaccaaag gcagaccgaa ggctccacag
1021 gtgtacacca ttccacctcc caaggagcag atggccaagg ataaagtcag tctgacctgc
1081 atgataacag acttcttccc tgaagacatt actgtggagt ggcagtggaa tgggcagcca
1141 gcggagaact acaagaacac tcagcccatc atggacacag atggctctta cttcgtctac
1201 agcaagctca atgtgcagaa gagcaactgg gaggcaggaa atactttcac ctgctctgtg
1261 ttacatgagg gcctgcacaa ccaccatact gagaagagcc tctcccactc tcctggtaaa
```

Protein Sequence Defining the Full Length Heavy Chain Sequence
(Heavy Chain Variable Region and IgG1 Constant Region) of 18H09

(SEQ ID NO: 105)

```
   1 evqlqesgps lvkpsqtlsl tcyvtgdsit sdywnwirkf pgnkleymgy isysgstyyn
  61 pslksrisit rdtsknqfyl rlnsvttedt atyycarthi ltiaywgqgt lvtvsaaktt
 121 ppsvyplapg saaqtnsmvt lgclvkgyfp epvtvtwnsg slssgvhtfp avlqsdlytl
 181 sssvtvpsst wpsetvtcnv ahpasstkvd kkivprdcgc kpcictvpev ssvfifppkp
 241 kdvltitltp kvtcvvvdis kddpevqfsw fvddvevhta qtqpreeqfn stfrsvselp
 301 imhqdwlngk efkcrvnsaa fpapiektis ktkgrpkapq vytipppkeq makdkvsltc
 361 mitdffpedi tvewqwngqp aenykntqpi mdtdgsyfvy sklnvqksnw eagntftcsv
 421 lheglhnhht ekslshspgk
```

Nucleic Acid Sequence Encoding the Full Length Light Chain Sequence
(Lambda Chain Variable Region and Constant Region (IGLC1)) of 18H09

(SEQ ID NO: 106)

```
   1 caggctgttg tgactcagga atctgcactc accacatcac ctggtgaaac agtcacactc
  61 acttgtcgct caagtgccgg ggctgttaca actagtaact ttgccaactg ggtccaagaa
 121 aaaccagatc atttattcac tggtctaata ggtgatacca acatccgagc tccaggtgtt
 181 cctgccagat tctcaggctc cctgattgga gacaaggctg ccctcaccat cacaggggca
 241 cagactgagg atgaggcaat atatttctgt gctctttggt acagcaacca ttactgggtg
 301 ttcggtggag gaaccaaact gactgtccta ggccagccca agtcttcgcc atcagtcacc
 361 ctgtttccac cttcctctga agagctcgag actaacaagg ccacactggt gtgtacgatc
```

-continued

```
421 actgatttct acccaggtgt ggtgacagtg gactggaagg tagatggtac ccctgtcact
481 cagggtatgg agacaaccca gccttccaaa cagagcaaca acaagtacat ggctagcagc
541 tacctgaccc tgacagcaag agcatgggaa aggcatagca gttacagctg ccaggtcact
601 catgaaggtc acactgtgga gaagagtttg tcccgtgctg actgttcc
```

Protein Sequence Defining the Full Length Light Chain Sequence (Lambda Chain Variable Region and Constant Region (IGLC1)) of 18H09

(SEQ ID NO: 107)

```
  1 qavvtqesal ttspgetvtl tcrssagavt tsnfanwvqe kpdhlftgli gdtnirapgv
 61 parfsgslig dkaaltitga qtedeaiyfc alwysnhywv fgggtkltvl gqpksspsvt
121 lfppsseele tnkatlvcti tdfypgvvtv dwkvdgtpvt qgmettqpsk qsnnkymass
181 yltltarawe rhssyscqvt heghtveksl sradcs
```

Nucleic Acid Sequence Encoding the Full Length Heavy Chain Sequence (Heavy Chain Variable Region and IgG1 Constant Region) of 29B06

(SEQ ID NO: 108)

```
   1 gaggtgcagc ttcaggagtc aggacctagc ctcgtgaaac cttctcagac tctgtccctc
  61 acctgttctg tcactggcga ctccatcacc agtggttact ggaactggat ccggaaattc
 121 ccagggaata aacttgagta catggggtac ataagctaca gtggtaaaac ttactacaat
 181 ccatctctca aaagtcgaat ctccatcact cgagacacat ccaagaacca ttactacctg
 241 cagttgattt ctgtgactgc tgaggacaca gccacatatt actgtgcaag gtctaagtac
 301 gactatgcta tggactactg gggtcaagga acctcagtca ccgtctcctc agccaaaacg
 361 acacccccat ctgtctatcc actggcccct ggatctgctg cccaaactaa ctccatggtg
 421 accctgggat gcctggtcaa gggctatttc cctgagccag tgacagtgac ctggaactct
 481 ggatccctgt ccagcggtgt gcacaccttc ccagctgtcc tgcagtctga cctctacact
 541 ctgagcagct cagtgactgt cccctccagc acctggccca gcgagaccgt cacctgcaac
 601 gttgcccacc cggccagcag caccaaggtg gacaagaaaa ttgtgcccag ggattgtggt
 661 tgtaagcctt gcatatgtac agtcccagaa gtatcatctg tcttcatctt ccccccaaag
 721 cccaaggatg tgctcaccat tactctgact cctaaggtca cgtgtgttgt ggtagacatc
 781 agcaaggatg atcccgaggt ccagttcagc tggtttgtag atgatgtgga ggtgcacaca
 841 gctcagacgc aaccccggga ggagcagttc aacagcactt tccgctcagt cagtgaactt
 901 cccatcatgc accaggactg gctcaatggc aaggagttca aatgcagggt caacagtgca
 961 gctttccctg cccccatcga gaaaaccatc tccaaaacca aaggcagacc gaaggctcca
1021 caggtgtaca ccattccacc tcccaaggag cagatggcca aggataaagt cagtctgacc
1081 tgcatgataa cagacttctt ccctgaagac attactgtgg agtggcagtg gaatgggcag
1141 ccagcggaga actacaagaa cactcagccc atcatggaca cagatggctc ttacttcgtc
1201 tacagcaagc tcaatgtgca gaagagcaac tgggaggcag gaaatacttt cacctgctct
1261 gtgttacatg agggcctgca caaccaccat actgagaaga gcctctccca ctctcctggt
1321 aaa
```

Protein Sequence Defining the Full Length Heavy Chain Sequence (Heavy Chain Variable Region and IgG1 Constant Region) of 29B06

(SEQ ID NO: 109)

```
  1 evqlqesgps lvkpsqtlsl tcsvtgdsit sgywnwirkf pgnkleymgy isysgktyyn
 61 pslksrisit rdtsknhyyl qlisvtaedt atyycarsky dyamdywgqg tsvtvssakt
121 tppsvyplap gsaaqtnsmv tlgclvkgyf pepvtvtwns gslssgvhtf pavlqsdlyt
181 lsssvtvpss twpsetvtcn vahpasstkv dkkivprdcg ckpcictvpe vssvfifppk
241 pkdvltitlt pkvtcvvvdi skddpevqfs wfvddvevht aqtqpreeqf nstfrsvsel
```

-continued

```
301 pimhqdwlng kefkcrvnsa afpapiekti sktkgrpkap qvytipppke qmakdkvslt

361 cmitdffped itvewqwngq paenykntqp imdtdgsyfv ysklnvqksn weagntftcs

421 vlheglhnhh tekslshspg k
```

Nucleic Acid Sequence Encoding the Full Length Light Chain Sequence (Kappa Chain Variable Region and Constant Region) of 29B06

(SEQ ID NO: 110)

```
  1 gacattgtgc tgacccaatc tccagcttct ttggctgtgt ctctaggaca gagggccacc

 61 atctcctgca gagccagcga aattgttgat aattttggca ttagttttat gaactggttc

121 caacagaaac caggacagcc acccaaactc ctcatctatg ctgcatccaa ccaaggatcc

181 ggggtccctg ccaggtttag tggcagtggg tctgggacag acttcagcct caacatccat

241 cctgtggagg aggatgatac tgcaatgtat ttctgtcagc aaagtaagga ggttcctccg

301 acgttcggtg gaggcaccaa gctggaaatc aaacgggctg atgctgcacc aactgtatcc

361 atcttcccac catccagtga gcagttaaca tctggaggtg cctcagtcgt gtgcttcttg

421 aacaacttct accccaaaga catcaatgtc aagtggaaga ttgatggcag tgaacgacaa

481 aatggcgtcc tgaacagttg gactgatcag gacagcaaag acagcaccta cagcatgagc

541 agcaccctca cgttgaccaa ggacgagtat gaacgacata acagctatac ctgtgaggcc

601 actcacaaga catcaacttc acccattgtc aagagcttca acaggaatga gtgt
```

Protein Sequence Defining the Full Length Light Chain Sequence (Kappa Chain Variable Region and Constant Region) of 29B06

(SEQ ID NO: 111)

```
  1 divltqspas lavslgqrat iscraseivd nfgisfmnwf qqkpgqppkl liyaasnqgs

 61 gvparfsgsg sgtdfslnih pveeddtamy fcqqskevpp tfgggtklei kradaaptvs

121 ifppsseqlt sggasvvcfl nnfypkdinv kwkidgserq ngvlnswtdq dskdstysms

181 stltltkdey erhnsytcea thktstspiv ksfnrnec
```

Table 4 shows the correspondence between the full-length sequences of the antibodies discussed in this Example with those presented in the Sequence Listing.

TABLE 4

| SEQ ID NO. | Nucleic Acid or Protein |
|---|---|
| 92 | 07F01 Heavy Variable + IgG1 Constant-nucleic acid |
| 93 | 07F01 Heavy Variable + IgG1 Constant-protein |
| 94 | 07F01 Kappa Variable + Constant-nucleic acid |
| 95 | 07F01 Kappa Variable + Constant-protein |
| 96 | 12B11 Heavy Variable + IgG1 Constant-nucleic acid |
| 97 | 12B11 Heavy Variable + IgG1 Constant-protein |
| 98 | 12B11 Kappa Variable + Constant-nucleic acid |
| 99 | 12B11 Kappa Variable + Constant-protein |
| 100 | 17F06 Heavy Variable + IgG2A Constant-nucleic acid |
| 101 | 17F06 Heavy Variable + IgG2A Constant-protein |
| 102 | 17F06 Lambda Variable + Constant (IGLC2)-nucleic acid |
| 103 | 17F06 Lambda Variable + Constant (IGLC2)-protein |
| 104 | 18H09 Heavy Variable + IgG1 Constant-nucleic acid |
| 105 | 18H09 Heavy Variable + IgG1 Constant-protein |
| 106 | 18H09 Lambda Variable + Constant (IGLC1)-nucleic acid |
| 107 | 18H09 Lambda Variable + Constant (IGLC1)-protein |
| 108 | 29B06 Heavy Variable + IgG1 Constant-nucleic acid |
| 109 | 29B06 Heavy Variable + IgG1 Constant-protein |
| 110 | 29B06 Kappa Variable + Constant-nucleic acid |
| 111 | 29B06 Kappa Variable + Constant-protein |

Example 5

Binding Affinities

The binding affinities and kinetics of binding of antibodies 07F01, 29B06, 17F06, 18H09, and 12B11 to recombinant human RON-ECD/mFc fusion protein (rhRON ECD/mFc) and recombinant human RON SEMA and PSI domains (rhRON SEMA+PSI) (R&D Systems, Inc., Minneapolis, Minn.) were measured by surface plasmon resonance, using a BIACORE® T100 instrument (GE Healthcare, Piscataway, N.J.).

Rabbit anti-mouse IgGs (GE Healthcare) were immobilized on carboxymethylated dextran CM4 sensor chips (GE Healthcare) by amine coupling, according to a standard protocol. Analyses were performed at 25° C. and 37° C., using PBS containing 0.05% surfactant P20 as running buffer. The antibodies were captured in individual flow cells at a flow rate of 10 μl/min. Injection time was varied for each antibody to yield an Rmax between 30 and 60 RU. 250 μg/mL mouse Fc were injected at 30 μl/min for 120 seconds to block non-specific binding of antibodies to Fc portion of the protein when needed. Buffer, rhRon ECD/mFc or rhRON SEMA+PSI diluted in running buffer was injected sequentially over a reference surface (no antibody captured) and the active surface (antibody to be tested) for 300 seconds at 60 μl/minute. The dissociation phase was monitored for up to 3600 seconds. The surface was then regenerated with two 60-second injections of 10 mM Glycine-HCl, pH 1.7, at a flow rate of 60 μl/min. The rhRON ECD/mFc or rhRON SEMA+PSI concentration range tested was 0.625 nM to 20 nM.

Kinetic parameters were determined using the kinetic function of the BIAevaluation software (GE Healthcare) with double reference subtraction. Kinetic parameters for each antibody, $k_a$ (association rate constant), $k_d$ (dissociation rate constant) and $K_D$ (equilibrium dissociation constant) were determined. Kinetic values of the monoclonal antibodies on rhRON ECD/mFc at 25° C. and 37° C. are summarized in Table 5.

TABLE 5

Antibody Binding to rhRON ECD/mFc

| Antibody | | Measurements at 25° C. | | | | Measurements at 37° C. | | | |
|---|---|---|---|---|---|---|---|---|---|
| | | ka (1/Ms) | kd (1/s) | $K_D$ (M) | n | ka (1/Ms) | kd (1/s) | $K_D$ (M) | n |
| 07F01 | AVG | 4.0E+05 | 9.3E−05 | 2.3E−10 | 4 | 2.1E+06 | 3.5E−04 | 2.1E−10 | 3 |
| | STDEV | 7.1E+04 | 5.5E−06 | 3.4E−11 | | 2.4E+06 | 2.8E−04 | 7.1E−11 | |
| 29B06 | AVG | 2.0E+05 | 1.3E−04 | 6.5E−10 | 3 | 2.3E+06 | 7.0E−04 | 2.8E−10 | 3 |
| | STDEV | 3.5E+04 | 1.0E−05 | 1.2E−10 | | 1.3E+06 | 4.8E−04 | 7.8E−11 | |
| 17F06 | AVG | 1.7E+05 | 4.6E−08* | 2.9E−13* | 3 | 1.4E+05 | 2.4E−05 | 2.1E−10 | 3 |
| | STDEV | 4.8E+04 | 3.3E−08 | 1.7E−13 | | 3.1E+04 | 2.2E−05 | 2.4E−10 | |
| 18H09 | AVG | 3.3E+05 | 5.7E−05 | 2.2E−10 | 3 | 1.8E+06 | 7.0E−04 | 4.0E−10 | 1 |
| | STDEV | 1.5E+05 | 2.3E−05 | 1.6E−10 | | | | | |
| 12B11 | AVG | 1.2E+05 | 5.9E−05 | 5.0E−10 | 3 | 2.0E+05 | 2.0E−04 | 1.1E−09 | 3 |
| | STDEV | 2.8E+04 | 1.7E−05 | 4.6E−11 | | 1.1E+05 | 3.8E−05 | 4.6E−10 | |

*Outside instrument limit of detection

The data in Table 5 demonstrate that antibodies 07F01, 29B06, 17F06, 18H09, and 12B11 bind rhRON ECD/mFc with a $K_D$ of about 1 nM or less, 750 pM or less, 650 pM or less, 600 pM or less, 500 pM or less, 400 pM or less, 300 pM or less, 250 pM or less, 200 pM or less, 150 pM or less, 100 pM or less, or 50 pM or less.

Kinetic values of the monoclonal antibodies on rhRON SEMA+PSI at 25° C. and 37° C. are summarized in Table 6.

TABLE 6

Antibody Binding to rhRON SEMA + PSI

| Antibody | | Measurements at 25° C. | | | | Measurements at 37° C. | | | |
|---|---|---|---|---|---|---|---|---|---|
| | | ka (1/Ms) | kd (1/s) | $K_D$ (M) | n | ka (1/Ms) | kd (1/s) | $K_D$ (M) | n |
| 07F01 | AVG | 5.2E+06 | 3.6E−04 | 8.8E−11 | 3 | 2.0E+06 | 8.0E−04 | 4.0E−10 | 3 |
| | STDEV | 7.0E+06 | 4.3E−04 | 3.3E−11 | | 2.1E+05 | 7.5E−05 | 8.3E−12 | |
| 29B06 | AVG | 4.2E+05 | 7.0E−05 | 1.8E−10 | 3 | 5.2E+05 | 6.9E−04 | 1.3E−09 | 3 |
| | STDEV | 1.2E+05 | 8.7E−06 | 6.1E−11 | | 4.7E+04 | 4.9E−05 | 9.9E−11 | |
| 17F06 | AVG | 1.9E+05 | 1.4E−06 | 9.0E−12 | 4 | 2.6E+05 | 2.1E−05 | 1.3E−10 | 3 |
| | STDEV | 3.6E+04 | 1.7E−06 | 1.1E−11 | | 1.2E+05 | 2.9E−05 | 1.9E−10 | |
| 18H09 | AVG | 4.4E+05 | 3.8E−06 | 8.6E−12 | 3 | 5.8E+05 | 1.2E−04 | 2.2E−10 | 2 |
| | STDEV | 2.7E+04 | 6.3E−06 | 1.4E−11 | | 7.6E+04 | 5.3E−05 | 1.2E−10 | |
| 12B11 | AVG | No binding | | | 2 | No binding | | | |

The data in Table 6 demonstrate that antibodies 07F01, 29B06, 17F06 and 18H09 bind rhRON SEMA+PSI with a $K_D$ of about 1 nM or less, 750 pM or less, 650 pM or less, 600 pM or less, 500 pM or less, 400 pM or less, 300 pM or less, 250 pM or less, 200 pM or less, 150 pM or less, 100 pM or less, 75 pM or less, 50 pM or less, or 10 pM or less. Antibody 12B11 did not bind to rhRON SEMA+PSI.

Binding to cell surface human wild-type RON and the delta 160 RON variant by antibodies 29B06 and 07F01 was measured at 4° C., using Fluorescence Activated Cell Sorting (FACS). PC3 cells expressing the human wild-type RON, and HT29 cells expressing the delta 160 variant, were harvested using cell dissociation buffer (Invitrogen), washed twice with FACS buffer (PBS with 0.5% BSA), and treated for 10 minutes with Cyto Q Antibody diluent and FC receptor block (Innovex Biosciences, Richmond, Calif.). Purified antibodies were diluted in FACS buffer over a concentration range from 0.02 nM to 40 nM. Cells were incubated with 100 µl of antibody for one hour, washed with FACS buffer three times, and incubated for 45 minutes with goat anti-mouse PE-conjugated antibody (Jackson ImmunoResearch Laboratories, West Grove, Pa.). Cells were washed three times with FACS buffer, resuspended in 300 µl of FACS buffer, and analyzed using a Beckman Coulter Cytomics FC 500 FACS instrument. Results are summarized in Table 7.

TABLE 7

| | 29B06 | 07F01 |
|---|---|---|
| Human RON - $K_D$ (nM) | 0.133 | 0.032 |
| Human RON - $K_D$ range (nM) | 0.089-0.177 | 0.025-0.039 |
| Delta 160 RON - $K_D$ (nM) | 0.146 | 0.024 |
| Delta 160 RON - $K_D$ range (nM) | 0.100-0.192 | 0.020-0.029 |

The results in Table 7 demonstrate that antibodies 29B06 and 07F01 bind both wild-type RON and the delta 160 RON variant on the cell surface with similar affinity.

Example 6

Cell Surface Binding

Binding to cell surface wild-type RON and delta 160 RON at 4° C. was determined for antibodies 07F01, 12B11, 17F06, 18H09, and 29B06, using FACS. Cells expressing wild-type RON (PC3), and cells expressing delta 160 RON (HT-29), were harvested using cell dissociation buffer (Invitrogen), washed twice with FACS buffer (0.5% BSA PBS) and treated with CytoQ Antibody diluent and FC receptor block (Innovex). Purified antibodies were diluted at a concentration of 10 μg/ml, in FACS buffer. Cells were incubated with 100 μl of antibody mix for one hour, washed with FACS buffer three times, and incubated for 45 minutes with goat anti-mouse PE conjugated antibody (Jackson Immunoresearch Laboratories). Cells were washed three times with FACS buffer, resuspended in 300 μl of FACS buffer and analyzed using a Beckman Coulter Cytomics FC 500 FACS instrument. Percent binding as compared to murine IgG control is shown in Table 8.

TABLE 8

| Antibody | PC3 % cell surface binding | HT-29 % cell surface binding |
|---|---|---|
| 07F01 | 99.29 | 99.08 |
| 17F06 | 99.08 | 99.00 |
| 29B06 | 99.06 | 99.04 |
| 18H09 | 99.03 | 98.33 |
| 12B11 | 94.52 | 88.64 |
| mIgG | 5.50 | 5.62 |

The results in Table 8 demonstrate that antibodies 07F01, 29B06, 17F06, 18H09, and 12B11 bind both wild-type RON and the delta 160 RON variant expressed on the surface of cells.

Example 7

Receptor Internalization

Antibody-stimulated receptor internalization was measured using FACS. PC3 cells were used to measure antibody-stimulated internalization of the wild-type RON receptor. HT-29 cells were used for the delta 160 RON receptor variant. Antibodies were first conjugated with R-Phycocerthrin (Prozyme cat. No. PJ31K). All cells were washed with PBS and treated with CytoQ Antibody diluent and FC receptor block (Innovex). Cells were incubated with the antibodies (10 μg/ml) for 2 hours at 37° C. or at 4° C. The cells were transferred to 4° C., washed with an acidic solution (0.5 M NaCl, 0.18 M Acetic Acid, 0.5% Na azide) to strip off the antibody remaining on the cell surface, and fixed using BD CYTOFIX/CYTOPERM™ kit (BD Biosciences, cat. No. 555028) to measure antibodies retained intracellularly due to internalization. At 37° C., cells can undergo antibody-mediated receptor internalization, and the process is inhibited at low temperature of 4° C., thus serving as a baseline (no internalization). The cells were analyzed using a Beckman Coulter Cytomics FC 500 FACS instrument. A lowered anti-RON median fluorescent intensity (MFI) and a left shift of the histograms at 4° C. compared to that obtained at 37° C. indicate antibody-induced receptor internalization. Receptor internalization was quantified by subtracting MFI at 4° C. from that at 37° C. Results are summarized in Table 9.

TABLE 9

| Antibody | MFI @ 37° C. − MFI @ 4° C. in PC-3 cells | MFI @ 37° C. − MFI @ 4° C. in HT-29 cells |
|---|---|---|
| mIgG control | −0.15 | −0.07 |
| 29B06 | 0.49 | 0.00 |
| 07F01 | 0.21 | 0.22 |
| 12B11 | 0.48 | 0.81 |

These results demonstrate that antibodies, 29B06, 07F01 and 12B11 induce receptor internalization in PC-3 cells expressing wild-type RON. Only 07F01 and 12B11 induce receptor internalization in HT-29 cells expressing delta 160 RON variant.

Example 8

Inhibition of MSP-RON Binding

Antibodies 07F01, 12B11, 17F06, 18H09, and 29B06 were tested for inhibition of MSP binding to hRON SEMA+PSI, as measured by electrochemiluminescence (ECL) assay as described in Example 3. The antibodies (concentration range: 0.006-10 μg/mL) were incubated for 45 minutes at room temperature.

Figure 6:
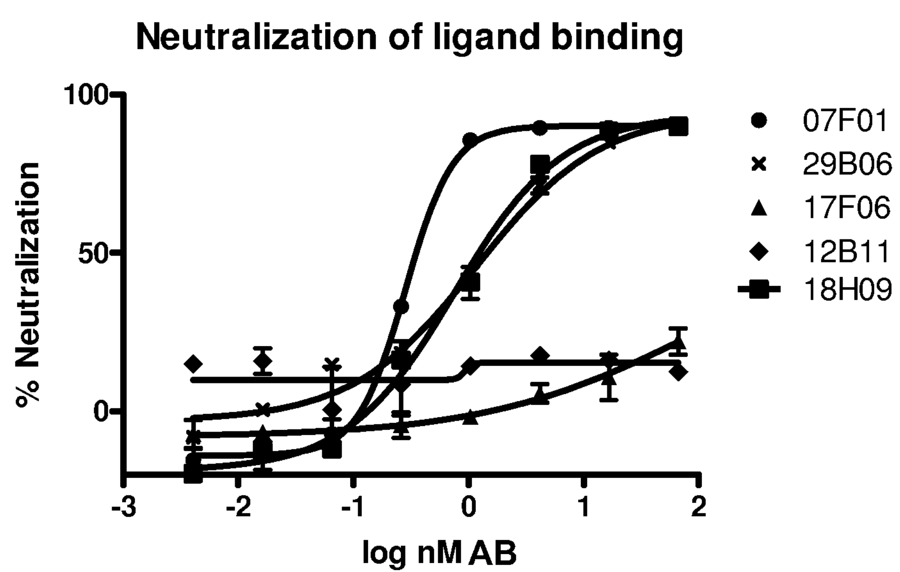
FIG. 6 is a graph showing dose-response curves for inhibition of the MSP-RON binding interaction by antibodies 17F06 (▲), 07F01 (●), 12B11 (♦), 18H09 (■), and 29B06 (x), as measured by electrochemiluminescence assay.

The MSP-hRON binding interaction was inhibited by antibodies 07F01, 18H06, and 29B06, but not by antibodies 17F06 and 12B11 (FIG. 6). The $IC_{50}$ and maximum percent inhibition values for the antibodies (IgG1) are shown in Table 10.

TABLE 10

| | $IC_{50}$ (nM) | | Maximum Neutralization (%) | | |
|---|---|---|---|---|---|
| Antibody | Average | Std Dev | Average | Std Dev | n |
| 07F01 | 0.26 | 0.05 | 88.3 | 2.1 | 3 |
| 18H09 | 0.91 | 0.15 | 86.9 | 6.7 | 3 |
| 29B06 | 1.11 | 0.06 | 87.6 | 4.7 | 3 |
| 12B11 | N/A | N/A | 44.8 | 20 | 3 |
| 17F06 | N/A | N/A | 7.9 | 11.2 | 2 |

The results in Table 10 demonstrate that antibodies 07F01, 18H09 and 29B06 block MSP binding to hRON SEMA+PSI, while antibodies 12B11 and 17F06 do not.

Example 9

Inhibition of Downstream Signaling by Anti-RON Antibodies

Antibodies 07F01, 12B11, 17F06, 18H09, and 29B06 were tested for inhibition of MSP-dependent phosphorylation of ERK, a RON downstream signaling molecule using the cell-based assay described in Example 3. The antibodies (concentration range: 0.006-10 μg/mL) in RPMI were added to the cells and incubated for one hour at 37° C.

Figure 7:
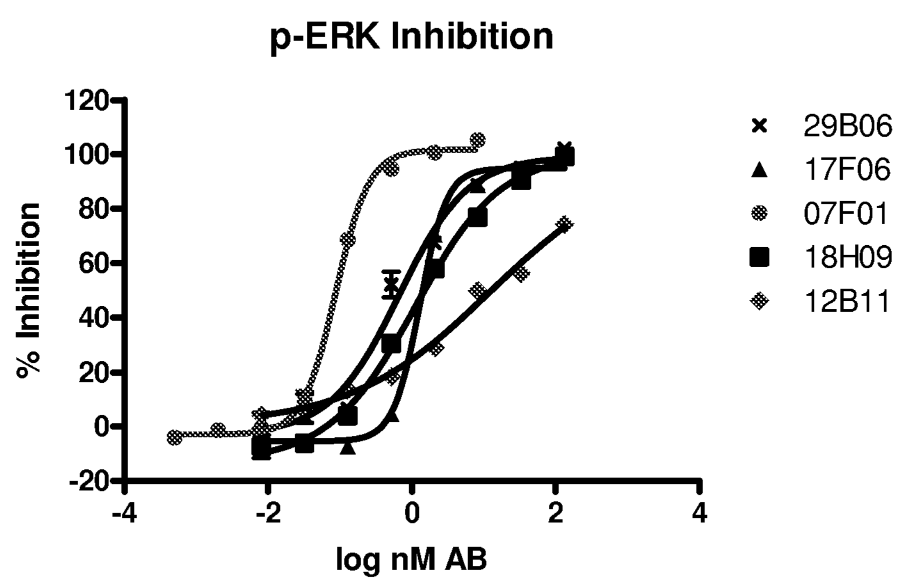
FIG. 7 is a graph showing dose-response curves for inhibition of MSP-dependent phosphorylation of ERK by antibodies 17F06 (▲), 07F01 (●), 12B11 (♦), 18H09 (■), and 29B06 (x) by ELISA assay.

Dose-dependent inhibition of ERK phosphorylation by antibodies 07F01, 12B11, 17F06, 18H09, and 29B06 is shown in Table 11 and FIG. 7.

TABLE 11

| Antibody | Mean IC50 (nM) | Std Dev | N |
|---|---|---|---|
| 07F01 | 0.07 | 0.02 | 3 |
| 18H09 | 0.71 | 0.36 | 3 |
| 29B06 | 0.44 | 0.27 | 3 |
| 12B11 | 5.91 | 5.92 | 3 |
| 17F06 | 0.96 | 0.4 | 3 |

The results in Table 11 and FIG. 7 demonstrate that antibodies 07F01, 18H09, 29B06, 12B11 and 17F06 inhibit MSP-induced ERK phosphorylation in T47D breast cancer cell line, even though 12B11 and 17F06 do not effectively block MSP binding to RON (see Examples 3 and 8).

Example 10

Inhibition of MSP-Dependent Cell Migration

Figure 8:
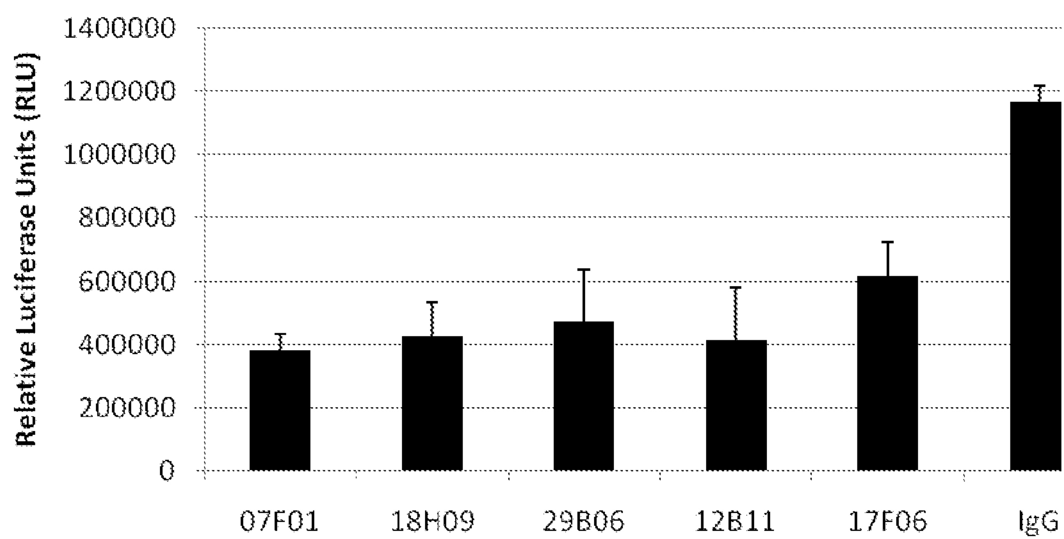
FIG. 8 is a histogram summarizing results from an experiment measuring inhibition of MSP induced HPAF-II cell migration by antibodies 07F01, 18H09, 29B06, 12B11, 17F06 and an IgG negative control (murine IgG) by transwell assay.

Antibodies 07F01, 18H09, 29B06, 12B11 and 17F06 were tested for inhibition of MSP-dependent cell migration. HPAF-II pancreatic cancer cells (ATCC) were incubated overnight under low serum conditions (1% FBS, MEM). Cells were trypsinized, counted, and placed at a concentration of 50,000/well in 45 μl of 1% FBS/MEM in the upper chamber of a BD 96-well FLUOROBLOK™ plate (Becton Dickinson). Antibodies were added at a concentration of 2 μg/ml, and cells were incubated for 2 hours. The bottom chamber contained 1% FBS MEM (200 μl) and 1 nM MSP, and cells were incubated for 24 hours. The number of migrated cells was determined by the addition of Calcien Dye at 4 μg/ml final concentration to the bottom chamber, followed by a one-hour incubation. Fluorescence intensity was measured using a WALLAC 1420 VICTOR™ instrument (Perkin Elmer). Baseline fluorescent measurements were done in the absence of MSP. Percent inhibition was determined by comparing antibody-treated and antibody-untreated samples to the baseline using the following formula: 100−(anti-RON antibody treated-baseline)/(control huIgG treated-baseline) *100. Results on inhibition of MSP-induced HPAFII cell migration by antibodies 07F01, 18H09, 29B06, 12B11, and 17F06 are summarized in Table 12 and FIG. 8.

TABLE 12

| Antibody (2 μg/ml) | Percent Inhibition |
|---|---|
| 07F01 | 95.63 |
| 29B06 | 96.79 |
| 17F06 | 70.74 |
| 18H09 | 106.96 |
| 12B11 | 98.93 |

The results in Table 12 demonstrate that antibodies 07F01, 18H09, 29B06, 12B11 and 17F06 inhibit MSP-dependent cell migration in HPAF-II pancreatic cancer cell lines, even though 12B11 and 17F06 do not effectively block MSP binding to RON.

Example 11

Inhibition of Growth of Wild-Type RON-Dependent Tumor Model

Figure 9:
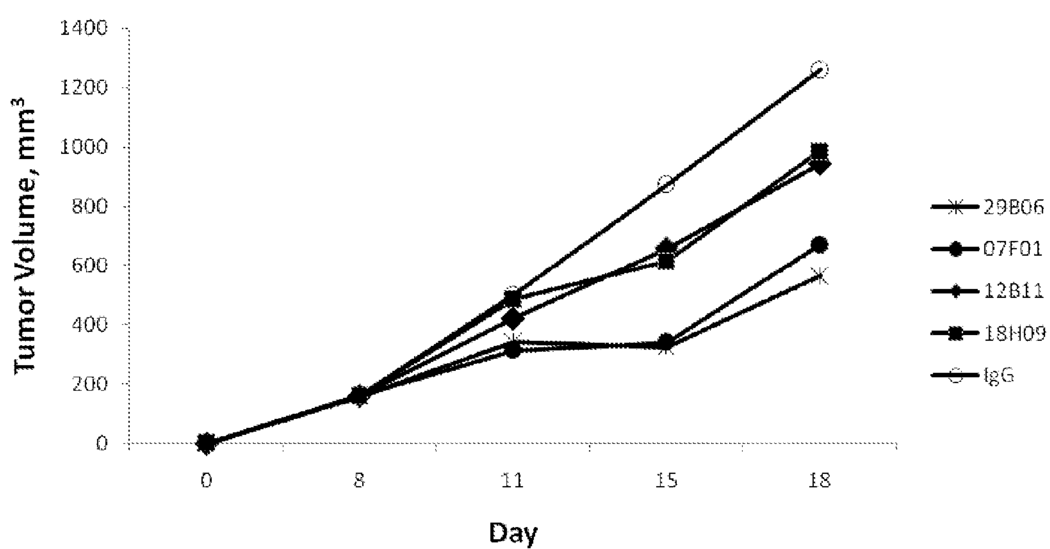
FIG. 9 is a graph summarizing data on inhibition of growth of a wild-type (wt) RON-dependent in vivo tumor model by antibodies 07F01 (●), 12B11 (♦), 18H09 (■), 29B06 (*), and a murine IgG control (○). The antibodies and IgG control were dosed at 20 mg/kg twice per week intraperitoneally.

Inhibition of tumor growth was tested in a directed complementation model of wild-type RON-driven tumor growth. "Directed complementation" tumors were obtained as described in Robinson et al., U.S. Pat. No. 7,556,796. A cDNA encoding wild-type human RON was introduced into BH3 tumor cells by retroviral transfer. Transfected tumor cells were then implanted subcutaneously into recipient mice. Growth of the BH3 tumors was dependent on expression of an inducible HER2 gene, which was not induced. Therefore, tumors would grow only if the RON gene functionally complemented the uninduced HER2 gene. Growth of the directed complementation tumors was observed. Primary tumors were propagated in vivo to generate sufficient tumor material for drug efficacy studies. Quality control for the directed complemented tumors included RT-PCR for RON expression and immunohistochemistry (IHC) for protein expression. The tumors were stored as frozen archival aliquots of approximately $1.5\times10^5$ cells/vial. These tumors were thawed, washed once, resuspended in HBS+matrigel and injected subcutaneously. Tumor measurements were taken twice weekly using vernier calipers. Tumor volume was calculated using the formula: width×width×length/2. When tumors reached approximately 150 mm$^3$, the mice were randomized into five groups of ten mice each. Each group (ten mice each) received one of the following antibody treatments: 07F01, 29B06, 12B11, or 18H09, or murine IgG control, all at 20 mg/kg. Treatment was administered by intra-peritoneal injection, twice weekly, for two weeks. Antibodies 29B06 and 07F01 resulted in tumor growth inhibition ("TGI") greater than 50% ($p<0.001$), while antibodies 18H09 and 12B11 exhibited TGI of 25% and 29%, respectively (FIG. 9). All treatments were well-tolerated with no significant loss in body weight.

Pharmacodynamic changes in RON receptor levels after 29B06 and 07F01 treatment were evaluated. Tumors were treated with 20 mg/kg of the following antibodies: mIgG (control), 29B06 or 07F01 and tumors were harvested at 24 or 48 hours. After harvest, the tumors were lysed in standard RIPA buffer (Boston Bioproducts, cat. No. BP-115) containing protease inhibitors (Roche, catalog No. 04693159001) and phosphatase inhibitors I and II (Sigma, cat. Nos. P2350 and P5726). Lysates were cleared and protein concentration was measured. A Western blot for total RON was done using a polyclonal anti-RON antibody (Santa Cruz, cat. No. sc-322). The Western blot analysis showed that antibody 29B06 induced receptor degradation in vivo in RON-DC xenograft at 24 hours, and to a greater extent at 48 hours.

Example 12

Inhibition of Growth of Delta 160 RON-Driven Tumor Model

Figure 10:
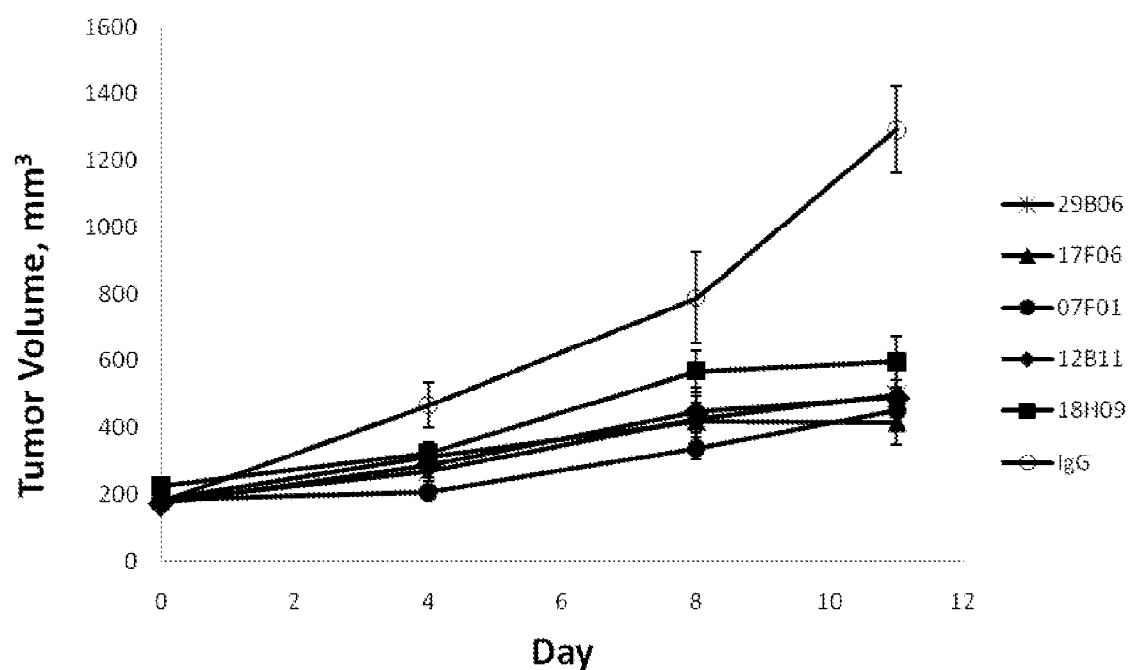
FIG. 10 is a graph summarizing data on inhibition of growth of a delta 160 RON-dependent in vivo tumor model by antibodies 17F06 (▲), 07F01 (●), 12B11 (♦), 18H09 (■), 29B06 (*), and a murine IgG control (○). The antibodies and IgG control were dosed at 20 mg/kg twice per week intraperitoneally.

Inhibition of tumor growth by the antibodies was tested in a directed complementation model of delta 160 RON-driven tumor growth. The model was obtained as described in Example 11, except that the transfected cDNA encoded human delta 160 (oncogenic) form of RON. Growth of the directed complementation tumors was observed. Primary tumors were propagated in vivo to generate sufficient tumor material for drug efficacy studies. Quality control for the directed complimented tumors included RT-PCR for RON expression and IHC for protein expression. The tumors were stored as frozen archival aliquots of approximately $1.5\times10^5$ cells/vial. These tumors were thawed, washed once, resuspended in HBS plus matrigel, and injected subcutaneously. Tumor measurements were taken twice weekly. When tumors reached approximately 150 mm$^3$, the mice were randomized into five groups of ten mice each. Each group (ten mice per group) received one of the following treatments: murine IgG control, 07F01, 29B06, 12B11, 17F06, and 18H09, all at 20 mg/kg. Treatment was administered by intra-peritoneal injection, twice weekly, for two weeks. Each treatment group showed similar tumor growth inhibition of greater than 60% ($p<0.001$) except for 18H09 (TGI 54%) as shown in FIG. 10. All treatments were well-tolerated, with no significant loss in body weight.

Example 13

Inhibition of Growth of NCI-H358 Lung Xenograft Tumor Model

Figure 11:
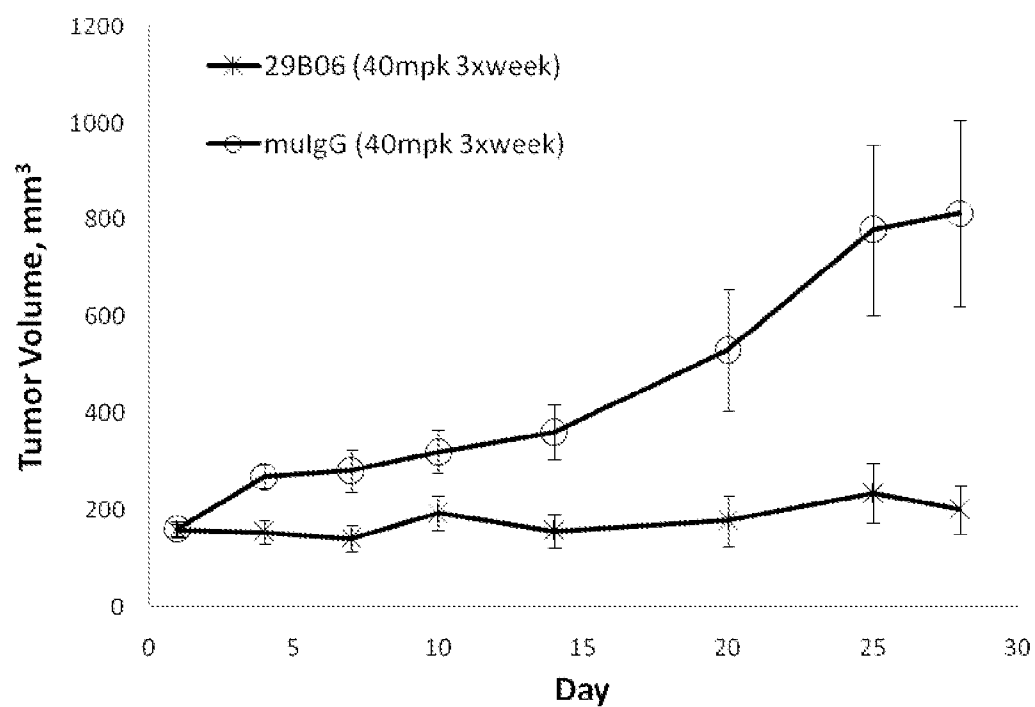
FIG. 11 is a graph summarizing data on inhibition of growth of an NCI-H358 xenograft tumor model by antibody 29B06 (*) and a murine IgG control (○). The antibody and IgG control were dosed at 40 mg/kg (abbreviated as "mpk") three per week intraperitoneally.

Inhibition of tumor growth by the 29B06 antibody was tested in an NCI-H358 lung xenograft model. The NCI-H358 cells were grown in culture at 37° C. in an atmosphere containing 5% $CO_2$, using RMPI medium (Invitrogen) containing 10% FBS. Cells were inoculated subcutaneously into the flank of 8-week old female CB.17 SCID mice with $5\times10^6$ cells per mouse in 50% matrigel. Tumor measurements were taken twice weekly. When tumors reached approximately 150 $mm^3$, the mice were randomized into two groups of ten mice each. Each group received one of the following treatments: murine IgG control or 29B06 at 40 mg/kg. Treatment was administered by intra-peritoneal injection three times per week, for three weeks. Antibody 29B06 treatment resulted in tumor growth inhibition of 70% ($p<0.001$) (FIG. 11). Treatment was well-tolerated, with no significant loss in body weight.

Example 14

Humanization of Anti-RON Antibodies

A. Construction of Humanized and Chimeric Anti-RON Antibodies

This Example describes the humanization of two murine antibodies, designated 07F01 and 29B06, and the characterization of the resulting humanized antibodies. The humanized anti-RON antibodies were designed using the SUPERHUMANIZATION™ method (Cephalon, Inc. (Arana Therapeutics Ltd.) and Hwang, W. Y. et al. (2005) METHODS 36:35-42), the CDR grafting method with back mutations (some human framework residues were changed to murine residues) (See e.g., U.S. Pat. Nos. 5,530,101; 5,693,761; 5,693,762; 5,585,089; 6,180,370; 7,022,500), or the HUMAN ENGINEERING™ method (Studnicka et al., Protein Eng. 1994 June; 7(6):805-14; also see, e.g., PCT Publication No. WO 93/11794 and U.S. Pat. Nos. 5,766,886; 5,770,196; 5,821,123; and 5,869,619). With the exception of heavy chain CDR1, the Kabat CDR definitions were used for CDR grafting onto human frameworks (SUPERHUMANIZATION™ and CDR grafting with back mutations). In some cases, a combination of Kabat and Chothia definitions were used for grafting heavy CDR1. In some cases, CDR residues (Kabat or Chothia definitions) were changed to human residues to increase humanness. Models of the murine antibodies were created using the SWISS-MODEL web server (swissmodel.expasy.org). Predicted residue contacts were determined using the Contact Map Analysis web server (ligin.weizmann.ac.il/cma/), and residue surface accessibility was determined using the Accessible Molecular Surface web server (swift.cmbi.ru.nl/servers/html/accessres.html). Residues were selected for back mutation based on predicted surface accessibility, contact with CDR residues, and involvement in the interface between heavy and light chains. Additionally, a cysteine residue present in the heavy chain CDR3 of 07F01 was changed to serine to prevent potential aggregation, and in some examples, a predicted N-linked glycosylation consensus site (N-X-S/T) in 07F01 heavy CDR2 (e.g., N58, Y59, T60) was mutated (e.g., T60A) to prevent any possible glycosylation. The designed amino acid sequences were converted to codon-optimized DNA sequences and synthesized by DNA2.0, Inc. to include (in the following order): 5' HindIII restriction site, Kozak consensus sequence, amino terminal signal sequence, humanized variable region, human IgG1 or Kappa constant region, stop codon, and a 3' EcoRI restriction site.

The anti-RON antibody chains humanized according to the SUPERHUMANIZATION™ method, as described herein, are designated with the prefix "Sh" before the antibody chain name. The anti-RON antibody chains humanized by the CDR grafting method with back mutations, as described herein, are designated with the prefix "Hu" before the antibody chain name. The anti-RON antibody chains humanized by the HUMAN ENGINEERING™ method, as described herein, are designated with the prefix "HE" before the antibody chain name.

The anti-RON antibody heavy chain 07F01 was humanized according to the SUPERHUMANIZATION™ method. Human germline sequence IGHV3-48*01 (also referred to herein as Hv3-48) was selected as the human heavy chain framework. In some embodiments, the human Hv3-48 heavy chain framework sequence was mutated at amino acid position 28 (e.g., D28T). Amino acid numbering is based on the Kabat numbering system.

The anti-RON antibody light chain 07F01 was humanized according to the HUMAN ENGINEERING™ method. Human germline sequence IGKV1-9*01 was selected as the human light chain framework.

The anti-RON antibody heavy chain 29B06 was humanized by the CDR grafting method with back mutations. Human germline sequence IGHV4-59*01 (also referred to herein as Hv4-59) was selected as the human framework. The human framework was back-mutated at amino acid positions 27, 30, 39, 44, 47, 48, 67, 71, and 78 to the murine sequence when the Kabat CDR definitions were used. The back-mutated human Hv4-59 framework sequence was further mutated to comprise at least one amino acid substitution at positions 27, 30, 48, 67, and 78. Amino acid substitutions in the back-mutated Hv4-59 framework sequence (e.g., amino acid substitution from a murine residue to a human residue, e.g., a human residue found in IGHV4-59) may be selected from the group consisting of D27G, T30S, M48I, I67V and Y78F. Amino acid numbering is based on the Kabat numbering system.

The anti-RON antibody light chain 29B06 was humanized according to the SUPERHUMANIZATION™ method. Human germline sequence IGKV2-28*01 was selected as the human light chain framework.

Chimeric (murine variable region and human constant region) 07F01 and 29B06 heavy (human IgG1) and light (human Kappa) chains were also constructed. The cysteine residue present in the heavy chain CDR3 of 07F01 was changed to serine to prevent potential aggregation. To generate chimeric antibodies, the murine variable regions were fused to the human constant region using overlap extension PCR, including (in the following order): 5' HindIII restriction site, Kozak consensus sequence, amino terminal signal sequence, mouse variable region, human IgG1 or Kappa constant region, stop codon, and 3' EcoRI restriction site.

The humanized and chimeric heavy chains were subcloned into pEE6.4 (Lonza, Basel, Switzerland) via HindIII and EcoRI sites using IN-FUSION™ PCR cloning (Clontech, Mountain View, Calif.). The humanized and chimeric Kappa light chains were subcloned into pEE14.4 (Lonza) via HindIII and EcoRI sites using IN-FUSION™ PCR cloning.

Humanized antibody chains or chimeric antibody chains were transiently transfected into 293T cells to produce antibody. Antibody was either purified or used in cell culture media supernatant for subsequent in vitro analysis. Binding of the chimeric and humanized antibodies to human RON was measured as described below. The results are summarized in Table 20.

Additionally, some humanized antibody heavy and light chain combinations were stably expressed in CHOK1SV cells using the GS SYSTEM™ (Lonza) in order to produce large quantities of purified humanized antibody. A single expression vector was constructed by combining pEE6.4 and pEE14.4 based vectors. First, pEE6.4 containing full length humanized heavy chain cDNA was digested with NotI and SalI to isolate the hCMV-MIE promoter+full length humanized heavy chain cDNA+SV40 poly A fragment. This fragment was inserted into the pEE14.4 vector already containing full length humanized light chain cDNA via NotI/SalI sites, thus creating an expression vector that simultaneously expresses heavy and light chains. The combined heavy and light chain vector was linearized and transfected into CHOK1SV cells. Stable clones were selected in the presence of methionine sulfoximine.

Each of the possible combinations of the humanized 07F01 immunoglobulin heavy chain and immunoglobulin light chain variable regions are set forth below in Table 13.

TABLE 13

| Light Chain Variable Region | Heavy Chain Variable Region |
|---|---|
| HE L 07F01 Kv1-9 Light Variable (SEQ ID NO: 139) | Sh07F01 Hv3-48 Heavy Variable (SEQ ID NO: 135) |
| HE L 07F01 Kv1-9 Light Variable (SEQ ID NO: 139) | Sh07F01 Hv3-48 D28T T60A L63V E65G Heavy Variable (SEQ ID NO: 137) |
| Sh07F01 Kv1-9 F1 Light Variable (SEQ ID NO: 141) | Sh07F01 Hv3-48 Heavy Variable (SEQ ID NO: 135) |
| Sh07F01 Kv1-9 F1 Light Variable (SEQ ID NO: 141) | Sh07F01 Hv3-48 D28T T60A L63V E65G Heavy Variable (SEQ ID NO: 137) |

Each of the possible combinations of the humanized 29B06 immunoglobulin heavy chain and immunoglobulin light chain variable regions are set forth below in Table 14.

TABLE 14

| Light Chain Variable Region | Heavy Chain Variable Region |
|---|---|
| Sh29B06 Kv2-28 Kappa Variable (SEQ ID NO: 149) | Sh29B06 Hv4-59 Heavy Variable (SEQ ID NO: 143) |
| Sh29B06_Kv2-28 Kappa Variable (SEQ ID NO: 149) | Hu29B06 Hv4-59 Heavy Variable (SEQ ID NO: 145) |
| Sh29B06 Kv2-28 Kappa Variable (SEQ ID NO: 149) | Hu29B06 Hv4-59 D27G T30S M48I I67V Y78F Heavy Variable (SEQ ID NO: 147) |

The nucleic acid sequences encoding and the protein sequences defining variable regions of the humanized 07F01 and 29B06 antibodies are summarized below (amino terminal signal peptide sequences are not shown). Sequences of the modified chimeric 07F01 heavy variable region in which the cysteine in CDR3 is changed to serine are also summarized below. CDR sequences (Kabat definition) are shown in bold and are underlined in the amino acid sequences.

Nucleic Acid Sequence Encoding the Chimeric 07F01 C102S Heavy Chain Variable Region (SEQ ID NO: 132)

```
  1 gaggtgaagc ttctcgagtc tggaggtggc ctggtgcagc cgggtggatc cctgaaactc
 61 tcctgtgcag cctcaggatt cgattttagt agacactgga tgagttgggt ccggctggct
121 ccagggaaag ggctagaatg gatcgcagaa attaatccag atagcagaac gataaactat
181 acgccatctc taaaggagaa attcatcatc tccagagaca acgccaaaaa ttcgctgttt
241 ctgcaaatga acagagtgag atctgaggac acagcccttt attactgtgc aagacgggta
301 agaattcatt actacggcgc tatggacagc tggggtcaag gaacctcagt caccgtctcc
361 tca
```

Protein Sequence Defining the Chimeric 07F01 C102S Heavy Chain Variable Region (SEQ ID NO: 133)

1 evkllesggg lvqpggslkl scaasgfdfs rhwmswvrla pgkglewiae inpdsrtiny

61 tpslkekfii srdnaknslf lqmnrvrsed talyycarrv rihyygamds wgqgtsvtvs 121 s Nucleic Acid Sequence Encoding the Sh07F01 Hv3-48 Heavy Chain Variable Region (SEQ ID NO: 134)

```
  1 gaggttcagc tggtagaatc cggaggaggg ttggtccaac ctggtggatc actcagactt
 61 tcatgcgccg ccagcggctt tgacttctca cgacattgga tgagctgggt ccggcaggct
121 ccaggcaagg gcctcgagtg ggttagcgag atcaatccag acagcagaac cattaactat
181 acacccagtc tgaaggagcg gttcaccata agccgtgata atgccaagaa ctccctgtac
```

-continued

241ttgcagatga actccttgcg cgctgaagat acagctgtgt actattgtgc aaggcgcgtg

301cgaatccact attacggggc aatggattct tggggccagg gtactaccgt gactgtgagt

361tct

Protein Sequence Defining the Sh07F01 Hv3-48 Heavy Chain Variable Region (SEQ ID NO: 135)

1evqlvesggg lvqpggslrl scaasgfdfs rhwmswvrqa pgkglewvse inpdsrtiny

61tpslkerfti srdnaknsly lqmnslraed tavyycarrv rihyygamds wgqgttvtvs

121s

Nucleic Acid Sequence Encoding the Sh07F01 Hv3-48 D28T T60A L63V E65G Heavy Chain Variable Region (SEQ ID NO: 136)

1gaggttcagc tggtagaatc cggaggaggg ttggtccaac ctggtggatc actcagactt

61tcatgcgccg ccagcggctt taccttctca cgacattgga tgagctgggt ccggcaggct

121ccaggcaagg gcctcgagtg ggttagcgag atcaatccag acagcagaac cattaactat

181gcccccagtg tgaagggccg gttcaccata agccgtgata atgccaagaa ctccctgtac

241ttgcagatga actccttgcg cgctgaagat acagctgtgt actattgtgc aaggcgcgtg

301cgaatccact attacggggc aatggattct tggggccagg gtactaccgt gactgtgagt

361tct

Protein Sequence Defining the Sh07F01 Hv3-48 D28T T60A L63V E65G Heavy Chain Variable Region (SEQ ID NO: 137)

1evqlvesggg lvqpggslrl scaasgftfs rhwmswvrqa pgkglewvse inpdsrtiny

61apsvkgrfti srdnaknsly lqmnslraed tavyycarrv rihyygamds wgqgttvtvs

121s

Nucleic Acid Sequence Encoding the HE_L 07F01_Kv1-9 Kappa Chain Variable Region (SEQ ID NO: 138)

1gatatccagt tgactcagtc tcagtccttt gtgagtacat cagtgggcga cagggtcacc

61gtgacctgcc gagcatcaca gaacgttgga agctctcttg tctggtatca gcaaaagcct

121gggaagagcc ccaaaaccct catctattct gcttcctttc tgtactccgg cgtaccaagt

181agattctctg gtagcggatc cgggacagag ttcactctca caattagcag tgtgcagcct

241gaggatttcg ccgactactt ctgtcagcaa tacaataact atcccctgac ttttggtggc

301ggcaccaaag tggaaatcaa g

Protein Sequence Defining the HE L 07F01 Kv1-9 Kappa Chain Variable Region (SEQ ID NO: 139)

1diqltqsqsf vstsvgdrvt vtcrasqnvg sslvwyqqkp gkspktliys asflysgvps 61rfsgsgsgte ftltissvqp edfadyfcqq ynnypltfgg gtkveik Nucleic Acid Sequence Encoding the sh07F01 Kv1-9 F1 Kappa Chain Variable Region (SEQ ID NO: 140)

1gacattcagc tgactcagtc gccgtcgttt ttgtcggcgt ccgtgggtga cagagtgact

61atcacatgtc gcgcttcgca aaacgtcgga tcatcgcttg tgtggtatca gcagaaaccc

121ggtaaagccc ctaagaccct catctattca gcgtcatttc tgtatagcgg ggtcccctca

181cggttcagcg gatccggctc cgggaccgag ttcacactca ctatttcgag cttgcagccg

241gaagattttg caacgtacta ctgccagcaa tacaataact acccactcac gttcggaggg

301ggaacgaagg tagagatcaa g

Protein Sequence Defining the sh07F01 Kv1-9 F1 Kappa Chain Variable Region

-continued (SEQ ID NO: 141)

1diqltqspsf lsasvgdrvt itcrasqnvg sslvwyqqkp gkapktliys asflysgvps 61rfsgsgsgte ftltisslqp edfatyycqq ynnypltfgg gtkveik Nucleic Acid Sequence Encoding the Sh29B06_Hv4-59 Heavy Chain Variable Region (SEQ ID NO: 142)

1caagttcagc tgcaagaatc cggaccagga ttggtcaaac cttcagagac actcagcctg

61acttgcaccg tgagcggtgg cagcatatcc tccggttatt ggaactggat ccggcagcca

121ccaggcaagg gcctcgagtg gattggctac atcagctata gcgggaaaac ctattacaac

181cccagtctga agagccgagt gaccataagc gtcgatacaa gtaagaacca gttctccctg

241aagctctcat ccgtgaccgc cgctgataca gctgtgtact attgtgcaag gtcaaagtat

301gactacgcaa tggactattg gggccagggt actctggtga ctgtgagttc t

Protein Sequence Defining the Sh29B06 Hv4-59 Heavy Chain Variable Region (SEQ ID NO: 143)

1qvqlqesgpg lvkpsetlsl tctvsggsis sgywnwirqp pgkglewigy isysgktyyn

61pslksrvtis vdtsknqfsl klssvtaadt avyycarsky dyamdywgqg tlvtvss

Nucleic Acid Sequence Encoding the Hu29B06_Hv4-59 Heavy Chain Variable Region (SEQ ID NO: 144)

1caagttcagc tgcaagaatc cggaccagga ttggtcaaac ccagcgaaac actctctctt

61acatgcaccg tgagcggcga ctctatcacc tcagggtatt ggaattggat tcggaaaccc

121ccaggcaaga agctcgagta catgggttac atcagttaca gcgggaaaac ctactataac

181cccagtctga agagcagaat caccataagc cgtgatacct ctaagaacca gtactccctg

241aagctgagtt ccgtaacagc agctgataca gctgtgtact attgtgcaag gagtaagtat

301gactacgcaa tggactattg gggccagggt actcttgtga ctgtgagttc t

Protein Sequence Defining the Hu29B06_Hv4-59 Heavy Chain Variable Region (SEQ ID NO: 145)

1qvqlqesgpg lvkpsetlsl tctvsgdsit sgywnwirkp pgkkleymgy isysgktyyn

61pslksritis rdtsknqysl klssvtaadt avyycarsky dyamdywgqg tlvtvss

Nucleic Acid Sequence Encoding the Hu29B06 D27G T30S M48I I67V Y78F Heavy Chain Variable Region (SEQ ID NO: 146)

1caagttcagc tgcaagaatc cggaccagga ttggtcaaac cttcagagac actcagcctg

61acttgcaccg tgagcggtgg cagcatatcc tccggttatt ggaactggat ccggaagcca

121ccaggcaaga agctcgagta cattggctac atcagctata gcgggaaaac ctattacaac

181cccagtctga agagccgagt gaccataagc agggatacaa gtaagaacca gttctccctg

241aagctctcat ccgtgaccgc cgctgataca gctgtgtact attgtgcaag gtcaaagtat

301gactacgcaa tggactattg gggccagggt actctggtga ctgtgagttc t

Protein Sequence Defining the Hu29B06 D27G T30S M48I I67V Y78F Heavy Chain Variable Region (SEQ ID NO: 147)

1qvqlqesgpg lvkpsetlsl tctvsggsis sgywnwirkp pgkkleyigy isysgktyyn

61pslksrvtis rdtsknqfsl klssvtaadt avyycarsky dyamdywgqg tlvtvss

Nucleic Acid Sequence Encoding the Sh29B06 Kv2-28 Kappa Chain Variable Region (SEQ ID NO: 148)

1gatatcgtta tgacccagag cccacttagt ttgcctgtta ctcctggcga gcctgccagt

61atttcttgcc gtgctagcga aatcgtggat aactttggta tatcattcat gaattggtat

121ctccaaaaac ctggccaaag cccccagctc cttatctacg ccgctagcaa ccaggggtcc

181ggggtacctg atagattttc aggcagcggc tctggaaccg acttcacact gaagatttcc

-continued

```
241cgggtggagg ccgaggacgt gggcgtgtac tattgtcaac agtccaagga agtccctccc

301actttcggcg gtgggacaaa ggttgagatt aag
```

Protein Sequence Defining the Sh29B06 Kv2-28 Kappa Chain Variable Region (SEQ ID NO: 149)

1divmtqspls lpvtpgepas iscrraseivd nfgisfmnwy lqkpgqspql liyaasnqgs

61gvpdrfsgsg sgtdftlkis rveaedvgvy ycqqskevpp tfgggtkvei k

The amino acid sequences defining the immunoglobulin heavy chain variable regions for the antibodies produced in Example 14 are aligned in FIGS. 12A and 12B. Amino terminal signal peptide sequences (for proper expression/secretion) are not shown. $CDR_1$, $CDR_2$, and $CDR_3$ (Kabat definition) are identified by boxes. FIGS. 13A and 13B show an alignment of the separate $CDR_1$, $CDR_2$, and $CDR_3$ sequences for each of the variable region sequences shown in FIGS. 12A and 12B, respectively.

The amino acid sequences defining the immunoglobulin light chain variable regions for the antibodies in Example 14 are aligned in FIGS. 14A and 14B. Amino terminal signal peptide sequences (for proper expression/secretion) are not shown. $CDR_1$, $CDR_2$ and $CDR_3$ are identified by boxes. FIGS. 15A and 15B show an alignment of the separate $CDR_1$, $CDR_2$, and $CDR_3$ sequences for each of the variable region sequences shown in FIGS. 14A and 14B, respectively.

Table 15 is a concordance chart showing the SEQ ID NO. of each sequence discussed in this Example.

TABLE 15

| SEQ. ID NO. | Nucleic Acid or Protein |
|---|---|
| 132 | Chimeric 07F01 C102S Heavy Chain Variable Region-nucleic acid |
| 133 | Chimeric 07F01 C102S Heavy Chain Variable Region-protein |
| 5 | Chimeric 07F01 C102S Heavy Chain $CDR_1$ |
| 6 | Chimeric 07F01 C102S Heavy Chain $CDR_2$ |
| 123 | Chimeric 07F01 C102S Heavy Chain $CDR_3$ |
| 134 | Sh07F01 Hv3-48 Heavy Chain Variable Region-nucleic acid |
| 135 | Sh07F01 Hv3-48 Heavy Chain Variable Region-protein |
| 5 | Sh07F01 Hv3-48 Heavy Chain $CDR_1$ |
| 6 | Sh07F01 Hv3-48 Heavy Chain $CDR_2$ |
| 123 | Sh07F01 Hv3-48 Heavy Chain $CDR_3$ |
| 136 | Sh07F01 Hv3-48 D28T T60A L63V E65G Heavy Chain Variable Region-nucleic acid |
| 137 | Sh07F01 Hv3-48 D28T T60A L63V E65G Heavy Chain Variable Region-protein |
| 5 | Sh07F01 Hv3-48 D28T T60A L63V E65G Heavy Chain $CDR_1$ |
| 122 | Sh07F01 Hv3-48 D28T T60A L63V E65G Heavy Chain $CDR_2$ |
| 123 | Sh07F01 Hv3-48 D28T T60A L63V E65G Heavy Chain $CDR_3$ |

TABLE 15-continued

| SEQ. ID NO. | Nucleic Acid or Protein |
|---|---|
| 138 | HE L 07F01 Kv1-9 Light (kappa) Chain Variable Region-nucleic acid |
| 139 | HE L 07F01 Kv1-9 Light (kappa) Chain Variable Region-protein |
| 130 | HE L 07F01 Kv1-9 Light (kappa) Chain $CDR_1$ |
| 131 | HE L 07F01 Kv1-9 Light (kappa) Chain $CDR_2$ |
| 10 | HE L 07F01 Kv1-9 Light (kappa) Chain $CDR_3$ |
| 140 | Sh07F01 Kv1-9 F1 Light (kappa) Chain Variable Region-nucleic acid |
| 141 | Sh07F01 Kv1-9 F1 Light (kappa) Chain Variable Region-protein |
| 130 | Sh07F01 Kv1-9 F1 Light (kappa) Chain $CDR_1$ |
| 131 | Sh07F01 Kv1-9 F1 Light (kappa) Chain $CDR_2$ |
| 10 | Sh07F01 Kv1-9 F1 Light (kappa) Chain $CDR_3$ |
| 142 | Sh29B06 Hv4-59 Heavy Chain Variable Region-nucleic acid |
| 143 | Sh29B06 Hv4-59 Heavy Chain Variable Region-protein |
| 45 | Sh29B06 Hv4-59 Heavy Chain $CDR_1$ |
| 46 | Sh29B06 Hv4-59 Heavy Chain $CDR_2$ |
| 47 | Sh29B06 Hv4-59 Heavy Chain $CDR_3$ |
| 144 | Hu29B06 Hv4-59 Heavy Chain Variable Region-nucleic acid |
| 145 | Hu29B06 Hv4-59 Heavy Chain Variable Region-protein |
| 45 | Hu29B06 Hv4-59 Heavy Chain $CDR_1$ |
| 46 | Hu29B06 Hv4-59 Heavy Chain $CDR_2$ |
| 47 | Hu29B06 Hv4-59 Heavy Chain $CDR_3$ |
| 146 | Hu29B06 Hv4-59 D27G T30S M48I I67V Y78F Heavy Chain Variable Region-nucleic acid |
| 147 | Hu29B06 Hv4-59 D27G T30S M48I I67V Y78F Heavy Chain Variable Region-protein |
| 45 | Hu29B06 Hv4-59 D27G T30S M48I I67V Y78F Heavy Chain $CDR_1$ |
| 46 | Hu29B06 Hv4-59 D27G T30S M48I I67V Y78F Heavy Chain $CDR_2$ |
| 47 | Hu29B06 Hv4-59 D27G T30S M48I I67V Y78F Heavy Chain $CDR_3$ |
| 148 | Sh29B06 Kv2-28 Light (kappa) Chain Variable Region-nucleic acid |
| 149 | Sh29B06 Kv2-28 Light (kappa) Chain Variable Region-protein |
| 48 | Sh29B06 Kv2-28 Light (kappa) Chain $CDR_1$ |
| 49 | Sh29B06 Kv2-28 Light (kappa) Chain $CDR_2$ |
| 50 | Sh29B06 Kv2-28 Light (kappa) Chain $CDR_3$ |

Humanized monoclonal antibody heavy chain CDR sequences (Kabat, Chothia, and IMGT definitions) are shown in Table 16.

TABLE 16

| | CDR1 | CDR2 | CDR3 |
|---|---|---|---|
| | | Kabat | |
| 07F01 | RHWMS (SEQ ID NO: 5) | EINPDSRTINYTPSLKE (SEQ ID NO: 6) | RVRIHYYGAMDC (SEQ ID NO: 7) |
| Chimeric 07F01 C102S | RHWMS (SEQ ID NO: 5) | EINPDSRTINYTPSLKE (SEQ ID NO: 6) | RVRIHYYGAMDS (SEQ ID NO: 123) |

TABLE 16-continued

| | CDR1 | CDR2 | CDR3 |
|---|---|---|---|
| Sh07F01 Hv3-48 | RHWMS (SEQ ID NO: 5) | EINPDSRTINYTPSLKE (SEQ ID NO: 6) | RVRIHYYGAMDS (SEQ ID NO: 123) |
| Sh07F01 Hv3-48 D28T T60A L63V E65G | RHWMS (SEQ ID NO: 5) | EINPDSRTINYAPSVKG (SEQ ID NO: 122) | RVRIHYYGAMDS (SEQ ID NO: 123) |
| 29B06 | SGYWN (SEQ ID NO: 45) | YISYSGKTYYNPSLKS (SEQ ID NO: 46) | SKYDYAMDY (SEQ ID NO: 47) |
| Sh29B06 Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 | SGYWN (SEQ ID NO: 45) | YISYSGKTYYNPSLKS (SEQ ID NO: 46) | SKYDYAMDY (SEQ ID NO: 47) |
| Hu29B06 Hv4-59 D27G T30S M48I I67V Y78F | SGYWN (SEQ ID NO: 45) | YISYSGKTYYNPSLKS (SEQ ID NO: 46) | SKYDYAMDY (SEQ ID NO: 47) |
| | | Chothia | |
| 07F01 | GFDFSRH (SEQ ID NO: 51) | NPDSRT (SEQ ID NO: 52) | RVRIHYYGAMDC (SEQ ID NO: 7) |
| Chimeric 07F01 C102S | GFDFSRH (SEQ ID NO: 51) | NPDSRT (SEQ ID NO: 52) | RVRIHYYGAMDS (SEQ ID NO: 125) |
| Sh07F01 Hv3-48 | GFDFSRH (SEQ ID NO: 51) | NPDSRT (SEQ ID NO: 52) | RVRIHYYGAMDS (SEQ ID NO: 125) |
| Sh07F01 Hv3-48 D28T T60A L63V E65G | GFTFSRH (SEQ ID NO: 124) | NPDSRT (SEQ ID NO: 52) | RVRIHYYGAMDS (SEQ ID NO: 125) |
| 29B06 | GDSITSG (SEQ ID NO: 59) | SYSGK (SEQ ID NO: 60) | SKYDYAMDY (SEQ ID NO: 47) |
| Sh29B06 Hv4-59 | GGSISSG (SEQ ID NO: 126) | SYSGK (SEQ ID NO: 60) | SKYDYAMDY (SEQ ID NO: 47) |
| Hu29B06 Hv4-59 | GDSITSG (SEQ ID NO: 59) | SYSGK (SEQ ID NO: 60) | SKYDYAMDY (SEQ ID NO: 47) |
| Hu29B06 Hv4-59 D27G T30S M48I I67V Y78F | GGSISSG (SEQ ID NO: 126) | SYSGK (SEQ ID NO: 60) | SKYDYAMDY (SEQ ID NO: 47) |
| | | IMGT | |
| 07F01 | GFDFSRHW (SEQ ID NO: 61) | INPDSRTI (SEQ ID NO: 62) | ARRVRIHYYGAMDC (SEQ ID NO: 63) |
| Chimeric 07F01 C102S | GFDFSRHW (SEQ ID NO: 61) | INPDSRTI (SEQ ID NO: 62) | ARRVRIHYYGAMDS (SEQ ID NO: 128) |
| Sh07F01 Hv3-48 | GFDFSRHW (SEQ ID NO: 61) | INPDSRTI (SEQ ID NO: 62) | ARRVRIHYYGAMDS (SEQ ID NO: 128) |
| Sh07F01 Hv3-48 D28T T60A L63V E65G | GFTFSRHW (SEQ ID NO: 127) | INPDSRTI (SEQ ID NO: 62) | ARRVRIHYYGAMDS (SEQ ID NO: 128) |
| 29B06 | GDSITSGY (SEQ ID NO: 73) | ISYSGKT (SEQ ID NO: 74) | ARSKYDYAMDY (SEQ ID NO: 75) |
| Sh29B06 Hv4-59 | GGSISSGY (SEQ ID NO: 129) | ISYSGKT (SEQ ID NO: 74) | ARSKYDYAMDY (SEQ ID NO: 75) |
| Hu29B06 Hv4-59 | GDSITSGY (SEQ ID NO: 73) | ISYSGKT (SEQ ID NO: 74) | ARSKYDYAMDY (SEQ ID NO: 75) |

TABLE 16-continued

| | CDR1 | CDR2 | CDR3 |
|---|---|---|---|
| Hu29B06 Hv4-59 D27G T30S M48I I67V Y78F | GGSISSGY (SEQ ID NO: 129) | ISYSGKT (SEQ ID NO: 74) | ARSKYDYAMDY (SEQ ID NO: 75) |

Humanized monoclonal antibody Kappa light chain CDR sequences (Kabat, Chothia, and IMGT definitions) are shown in Table 17.

TABLE 17

| | CDR1 | CDR2 | CDR3 |
|---|---|---|---|
| | Kabat/Chothia | | |
| 07F01 | KASQNVGSSLV (SEQ ID NO: 8) | SASFRYS (SEQ ID NO: 9) | QQYNNYPLT (SEQ ID NO: 10) |
| HE L 07F01 Kv1-9 | RASQNVGSSLV (SEQ ID NO: 130) | SASFLYS (SEQ ID NO: 131) | QQYNNYPLT (SEQ ID NO: 10) |
| Sh07F01 Kv1-9 F1 | RASQNVGSSLV (SEQ ID NO: 130) | SASFLYS (SEQ ID NO: 131) | QQYNNYPLT (SEQ ID NO: 10) |
| 29B06 | RASEIVDNFGISFMN (SEQ ID NO: 48) | AASNQGS (SEQ ID NO: 49) | QQSKEVPPT (SEQ ID NO: 50) |
| Sh29B06 Kv2-28 | RASEIVDNFGISFMN (SEQ ID NO: 48) | AASNQGS (SEQ ID NO: 49) | QQSKEVPPT (SEQ ID NO: 50) |
| | IMGT | | |
| 07F01 | QNVGSS (SEQ ID NO: 76) | SAS | QQYNNYPLT (SEQ ID NO: 10) |
| HE L 07F01 Kv1-9 | QNVGSS (SEQ ID NO: 76) | SAS | QQYNNYPLT (SEQ ID NO: 10) |
| Sh07F01 Kv1-9 F1 | QNVGSS (SEQ ID NO: 76) | SAS | QQYNNYPLT (SEQ ID NO: 10) |
| 29B06 | EIVDNFGISF (SEQ ID NO: 81) | AAS | QQSKEVPPT (SEQ ID NO: 50) |
| Sh29B06 Kv2-28 | EIVDNFGISF (SEQ ID NO: 81) | AAS | QQSKEVPPT (SEQ ID NO: 50) |

To create the complete chimeric and humanized heavy or kappa chain antibody sequences, each variable sequence above is combined with its respective human constant region. For example, a complete heavy chain comprises a heavy variable sequence followed by a human IgG1 heavy chain constant sequence. A complete kappa chain comprises a kappa variable sequence followed by the human kappa light chain constant sequence.

Nucleic Acid Sequence Encoding the Human IgG1 Heavy Chain Constant Region (SEQ ID NO: 150)

```
  1 gcctcaacaa aaggaccaag tgtgttccca ctcgccccta gcagcaagag tacatccggg

 61 ggcactgcag cactcggctg cctcgtcaag gattattttc cagagccagt aaccgtgagc

121 tggaacagtg gagcactcac ttctggtgtc catacttttc ctgctgtcct gcaaagctct

181 ggcctgtact cactcagctc cgtcgtgacc gtgccatctt catctctggg cactcagacc

241 tacatctgta atgtaaacca caagcctagc aatactaagg tcgataagcg ggtggaaccc

301 aagagctgcg acaagactca cacttgtccc ccatgccctg cccctgaact tctgggcggt

361 cccagcgtct ttttgttccc accaaagcct aaagatactc tgatgataag tagaacaccc

421 gaggtgacat gtgttgttgt agacgtttcc cacgaggacc cagaggttaa gttcaactgg
```

-continued

```
481 tacgttgatg gagtcgaagt acataatgct aagaccaagc ctagagagga gcagtataat

541 agtacatacc gtgtagtcag tgttctcaca gtgctgcacc aagactggct caacggcaaa

601 gaatacaaat gcaaagtgtc caacaaagca ctcccagccc ctatcgagaa gactattagt

661 aaggcaaagg ggcagcctcg tgaaccacag gtgtacactc tgccacccag tagagaggaa

721 atgacaaaga accaagtctc attgacctgc ctggtgaaag gcttctaccc cagcgacatc

781 gccgttgagt gggagagtaa cggtcagcct gagaacaatt acaagacaac cccccccagtg

841 ctggatagtg acgggtcttt ctttctgtac agtaagctga ctgtggacaa gtcccgctgg

901 cagcagggta acgtcttcag ctgttccgtg atgcacgagg cattgcacaa ccactacacc

961 cagaagtcac tgagcctgag cccagggaag
```

Protein Sequence Defining the Human IgG1 Heavy Chain Constant Region (SEQ ID NO: 151)

```
  1 astkgpsvfp lapsskstsg gtaalgclvk dyfpepvtvs wnsgaltsgv htfpavlqss

 61 glyslssvvt vpssslgtqt yicnvnhkps ntkvdkrvep kscdkthtcp pcpapellgg

121 psvflfppkp kdtlmisrtp evtcvvvdvs hedpevkfnw yvdgvevhna ktkpreeqyn

181 styrvvsvlt vlhqdwlngk eykckvsnka lpapiektis kakgqprepq vytlppsree

241 mtknqvsltc lvkgfypsdi avewesngqp ennykttppv ldsdgsffly skltvdksrw

301 qqgnvfscsv mhealhnhyt qkslslspgk
```

Nucleic Acid Sequence Encoding the Human Kappa Light Chain Constant Region (used for chimeric antibodies) (SEQ ID NO: 152)

```
  1 cgcacagtcg ccgctccctc cgtgttcatc tttccaccaa gtgatgagca actgaagtct

 61 ggtactgctt cagtcgtgtg tctgctgaac aatttctacc ctcgagaagc caaagtccaa

121 tggaaggtag acaacgcact gcagtccggc aatagccaag aatcagttac cgaacaggat

181 tcaaaggaca gtacatattc cctgagcagc actctgaccc tgtcaaaggc cgattacgag

241 aaacacaagg tctatgcttg cgaagtgaca catcagggac tgtccagccc agtgacaaaa

301 tcttttaacc gtggggagtg t
```

Nucleic Acid Sequence Encoding the Human Kappa Light Chain Constant Region (used for humanized antibodies) (SEQ ID NO: 153)

```
  1 cgcacagttg ctgcccccag cgtgttcatt ttcccaccta gcgatgagca gctgaaaagc

 61 ggtactgcct ctgtcgtatg cttgctcaac aacttttacc cacgtgaggc taaggtgcag

121 tggaaagtgg ataatgcact tcaatctgga aacagtcaag agtccgtgac agaacaggac

181 agcaaagact caacttattc actctcttcc accctgactc tgtccaaggc agactatgaa

241 aaacacaagg tatacgcctg cgaggttaca caccagggtt tgtctagtcc tgtcaccaag

301 tccttcaata ggggcgaatg t
```

Protein Sequence Defining the Human Kappa Light Chain Constant Region (used for chimeric and humanized antibodies) (SEQ ID NO: 154)

```
  1 rtvaapsvfi fppsdeqlks gtasvvclln nfypreakvq wkvdnalqsg nsqesvteqd

 61 skdstyslss tltlskadye khkvyacevt hqglsspvtk sfnrgec
```

The following sequences represent the actual or contemplated full length heavy and light chain sequence (i.e., containing both the variable and constant regions sequences) for each antibody described in this Example. Signal sequences for proper secretion of the antibodies (e.g., signal sequences at the 5' end of the DNA sequences or the amino terminal end of the protein sequences) are not shown in the full length heavy and light chain sequences disclosed herein and are not included in the final secreted protein. Also not shown are stop codons for termination of translation required at the 3' end of the DNA sequences. It is within ordinary skill in the art to select a signal sequence and/or a stop codon for expression of the disclosed full length IgG heavy chain and light chain sequences. It is also contemplated that the variable region sequences can be ligated to other constant region sequences to produce active full length IgG heavy and light chains.

Nucleic Acid Sequence Encoding the Full Length Chimeric 07F01 C102S Heavy Chain (Mouse Heavy Chain Variable Region and Human IgG1 Constant Region)

(SEQ ID NO: 155)

```
   1 gaggtgaagc ttctcgagtc tggaggtggc ctggtgcagc cgggtggatc cctgaaactc
  61 tcctgtgcag cctcaggatt cgattttagt agacactgga tgagttgggt ccggctggct
 121 ccagggaaag ggctagaatg gatcgcagaa attaatccag atagcagaac gataaactat
 181 acgccatctc taaaggagaa attcatcatc tccagagaca acgccaaaaa ttcgctgttt
 241 ctgcaaatga acagagtgag atctgaggac acagcccttt attactgtgc aagacgggta
 301 agaattcatt actacggcgc tatggacagc tggggtcaag gaacctcagt caccgtctcc
 361 tcagcctcaa caaaaggacc aagtgtgttc ccactcgccc ctagcagcaa gagtacatcc
 421 gggggcactg cagcactcgg ctgcctcgtc aaggattatt ttccagagcc agtaaccgtg
 481 agctggaaca gtggagcact cacttctggt gtccatactt ttcctgctgt cctgcaaagc
 541 tctggcctgt actcactcag ctccgtcgtg accgtgccat cttcatctct gggcactcag
 601 acctacatct gtaatgtaaa ccacaagcct agcaatacta aggtcgataa gcgggtggaa
 661 cccaagagct gcgacaagac tcacacttgt cccccatgcc ctgcccctga acttctgggc
 721 ggtcccagcg tctttttgtt cccaccaaag cctaaagata ctctgatgat aagtagaaca
 781 cccgaggtga catgtgttgt tgtagacgtt tcccacgagg acccagaggt taagttcaac
 841 tggtacgttg atggagtcga agtacataat gctaagacca agcctagaga ggagcagtat
 901 aatagtacat accgtgtagt cagtgttctc acagtgctgc accaagactg gctcaacggc
 961 aaagaataca aatgcaaagt gtccaacaaa gcactcccag cccctatcga gaagactatt
1021 agtaaggcaa aggggcagcc tcgtgaacca caggtgtaca ctctgccacc cagtagagag
1081 gaaatgacaa agaaccaagt ctcattgacc tgcctggtga aaggcttcta ccccagcgac
1141 atcgccgttg agtgggagag taacggtcag cctgagaaca attacaagac aacccccccca
1201 gtgctggata gtgacgggtc tttctttctg tacagtaagc tgactgtgga caagtcccgc
1261 tggcagcagg gtaacgtctt cagctgttcc gtgatgcacg aggcattgca caaccactac
1321 acccagaagt cactgagcct gagcccaggg aag
```

Protein Sequence Defining the Full Length Chimeric 07F01 C102S Heavy Chain (Mouse Heavy Chain Variable Region and Human IgG1 Constant Region)

(SEQ ID NO: 156)

```
   1 evkllesggg lvqpggslkl scaasgfdfs rhwmswvrla pgkglewiae inpdsrtiny
  61 tpslkekfii srdnaknslf lqmnrvrsed talyycarrv rihyygamds wgqgtsvtvs
 121 sastkgpsvf plapsskstS ggtaalgclv kdyfpepvtv swnsgaltsg vhtfpavlqs
 181 sglyslssvv tvpssslgtq tyicnvnhkp sntkvdkrve pkscdkthtc ppcpapellg
 241 gpsvflfppk pkdtlmisrt pevtcvvvdv shedpevkfn wyvdgvevhn aktkpreeqy
 301 nstyrvvsvl tvlhqdwlng keykckvsnk alpapiekti skakgqprep qvytlppsre
 361 emtknqvslt clvkgfypsd iavewesngq pennykttpp vldsdgsffl yskltvdksr
 421 wqqgnvfscs vmhealhnhy tqkslslspg k
```

Nucleic Acid Sequence Encoding the Full Length Chimeric 07F01 Light Chain (Mouse Kappa Chain Variable Region and Human Kappa Constant Region)

(SEQ ID NO: 157)

```
   1 gacattgtgt tgacccagtc tcaaaaaatc gtgtccacat cagtaggagc cagggtcagc
  61 gtcacctgca aggccagtca gaatgtgggt tctagtttag tctggtatca acagaaacca
 121 ggtcaatctc ctaaaacact gatttactcg gcatccttcc ggtacagtgg agtccctgat
 181 cgcttcacag gcagtggatc tgggacagat ttcactctca ccatcagcaa tgtgcagtct
 241 gaagacttgg cagattattt ctgtcaacaa tataataact atccgctcac gttcggtgct
```

-continued

```
301 gggaccaagc tggagctgaa acgcacagtc gccgctccct ccgtgttcat ctttccacca

361 agtgatgagc aactgaagtc tggtactgct tcagtcgtgt gtctgctgaa caatttctac

421 cctcgagaag ccaaagtcca atggaaggta gacaacgcac tgcagtccgg caatagccaa

481 gaatcagtta ccgaacagga ttcaaaggac agtacatatt ccctgagcag cactctgacc

541 ctgtcaaagg ccgattacga gaaacacaag gtctatgctt gcgaagtgac acatcaggga

601 ctgtccagcc cagtgacaaa atcttttaac cgtggggagt gt
```

Protein Sequence Defining the Full Length Chimeric 07F01 Light Chain (Mouse Kappa Chain Variable Region and Human Kappa Constant Region)

(SEQ ID NO: 158)

```
1 divltqsqki vstsvgarvs vtckasqnvg sslvwyqqkp gqspktliys asfrysgvpd

61 rftgsgsgtd ftltisnvqs edladyfcqq ynnypltfga gtklelkrtv aapsvfifpp

121 sdeqlksgta svvcllnnfy preakvqwkv dnalqsgnsq esvteqdskd styslsstlt

181 lskadyekhk vyacevthqg lsspvtksfn rgec
```

Nucleic Acid Sequence Encoding the Full Length Chimeric 29B06 Heavy Chain (Mouse Heavy Chain Variable Region and Human IgG1 Constant Region)

(SEQ ID NO: 159)

```
1 gaggtgcagc ttcaggagtc aggacctagc ctcgtgaaac cttctcagac tctgtccctc

61 acctgttctg tcactggcga ctccatcacc agtggttact ggaactggat ccggaaattc

121 ccagggaata aacttgagta catggggtac ataagctaca gtggtaaaac ttactacaat

181 ccatctctca aaagtcgaat ctccatcact cgagacacat ccaagaacca ttactacctg

241 cagttgattt ctgtgactgc tgaggacaca gccacatatt actgtgcaag gtctaagtac

301 gactatgcta tggactactg gggtcaagga acctcagtca ccgtctcctc agcctcaaca

361 aaaggaccaa gtgtgttccc actcgcccct agcagcaaga gtacatccgg gggcactgca

421 gcactcggct gcctcgtcaa ggattatttt ccagagccag taaccgtgag ctggaacagt

481 ggagcactca cttctggtgt ccatactttt cctgctgtcc tgcaaagctc tggcctgtac

541 tcactcagct ccgtcgtgac cgtgccatct tcatctctgg gcactcagac ctacatctgt

601 aatgtaaacc acaagcctag caatactaag gtcgataagc gggtggaacc caagagctgc

661 gacaagactc acacttgtcc cccatgccct gcccctgaac ttctgggcgg tcccagcgtc

721 tttttgttcc caccaaagcc taaagatact ctgatgataa gtagaacacc cgaggtgaca

781 tgtgttgttg tagacgtttc ccacgaggac ccagaggtta agttcaactg gtacgttgat

841 ggagtcgaag tacataatgc taagaccaag cctagagagg agcagtataa tagtacatac

901 cgtgtagtca gtgttctcac agtgctgcac caagactggc tcaacggcaa agaatacaaa

961 tgcaaagtgt ccaacaaagc actcccagcc cctatcgaga agactattag taaggcaaag

1021 gggcagcctc gtgaaccaca ggtgtacact ctgccaccca gtagagagga aatgacaaag

1081 aaccaagtct cattgacctg cctggtgaaa ggcttctacc ccagcgacat cgccgttgag

1141 tgggagagta acggtcagcc tgagaacaat tacaagacaa cccccccagt gctggatagt

1201 gacgggtctt tctttctgta cagtaagctg actgtggaca agtcccgctg gcagcagggt

1261 aacgtcttca gctgttccgt gatgcacgag gcattgcaca accactacac ccagaagtca

1321 ctgagcctga gcccagggaa g
```

Protein Sequence Defining the Full Length Chimeric 29B06 Heavy Chain (Mouse Heavy Chain Variable Region and Human IgG1 Constant Region)

(SEQ ID NO: 160)

```
1 evqlqesgps lvkpsqtlsl tcsvtgdsit sgywnwirkf pgnkleymgy isysgktyyn

61 pslksrisit rdtsknhyyl qlisvtaedt atyycarsky dyamdywgqg tsvtvssast

121 kgpsvfplap sskstsggta algclvkdyf pepvtvswns galtsgvhtf pavlqssgly
```

-continued

```
181 slssvvtvps sslgtqtyic nvnhkpsntk vdkrvepksc dkthtcppcp apellggpsv

241 flfppkpkdt lmisrtpevt cvvvdvshed pevkfnwyvd gvevhnaktk preeqynsty

301 rvvsvltvlh qdwlngkeyk ckvsnkalpa piektiskak gqprepqvyt lppsreemtk

361 nqvsltclvk gfypsdiave wesngqpenn ykttppvlds dgsfflyskl tvdksrwqqg

421 nvfscsvmhe alhnhytqks lslspgk
```

Nucleic Acid Sequence Encoding the Full Length Chimeric 29B06 Light Chain (Mouse Kappa Chain Variable Region and Human Kappa Constant Region)

(SEQ ID NO: 161)

```
  1 gacattgtgc tgacccaatc tccagcttct ttggctgtgt ctctaggaca gagggccacc

 61 atctcctgca gagccagcga aattgttgat aatttggca ttagttttat gaactggttc

121 caacagaaac caggacagcc acccaaactc ctcatctatg ctgcatccaa ccaaggatcc

181 ggggtccctg ccaggtttag tggcagtggg tctgggacag acttcagcct caacatccat

241 cctgtggagg aggatgatac tgcaatgtat ttctgtcagc aaagtaagga ggttcctccg

301 acgttcggtg gaggcaccaa gctggaaatc aaacgcacag tcgccgctcc ctccgtgttc

361 atctttccac caagtgatga gcaactgaag tctggtactg cttcagtcgt gtgtctgctg

421 aacaatttct accctcgaga agccaaagtc caatggaagg tagacaacgc actgcagtcc

481 ggcaatagcc aagaatcagt taccgaacag gattcaaagg acagtacata ttccctgagc

541 agcactctga ccctgtcaaa ggccgattac gagaaacaca aggtctatgc ttgcgaagtg

601 acacatcagg gactgtccag cccagtgaca aaatctttta accgtgggga gtgt
```

Protein Sequence Defining the Full Length Chimeric 29B06 Light Chain (Mouse Kappa Chain Variable Region and Human Kappa Constant Region)

(SEQ ID NO: 162)

```
  1 divltqspas lavslgqrat iscraseivd nfgisfmnwf qqkpgqppkl liyaasnqgs

 61 gvparfsgsg sgtdfslnih pveeddtamy fcqqskevpp tfgggtklei krtvaapsvf

121 ifppsdeqlk sgtasvvcll nnfypreakv qwkvdnalqs gnsqesvteq dskdstysls

181 stltlskady ekhkvyacev thqglsspvt ksfnrgec
```

Nucleic Acid Sequence Encoding the Full Length Humanized Sh07F01 Hv3-48 Heavy Chain (Humanized Heavy Chain Variable Region and Human IgG1 Constant Region)

(SEQ ID NO: 163)

```
  1 gaggttcagc tggtagaatc cggaggaggg ttggtccaac ctggtggatc actcagactt

 61 tcatgcgccg ccagcggctt tgacttctca cgacattgga tgagctgggt ccggcaggct

121 ccaggcaagg gcctcgagtg ggttagcgag atcaatccag acagcagaac cattaactat

181 acacccagtc tgaaggagcg gttcaccata agccgtgata atgccaagaa ctccctgtac

241 ttgcagatga actccttgcg cgctgaagat acagctgtgt actattgtgc aaggcgcgtg

301 cgaatccact attacggggc aatggattct tggggccagg gtactaccgt gactgtgagt

361 tctgcctcaa caaaaggacc aagtgtgttc ccactcgccc ctagcagcaa gagtacatcc

421 gggggcactg cagcactcgg ctgcctcgtc aaggattatt ttccagagcc agtaaccgtg

481 agctggaaca gtggagcact cacttctggt gtccatactt ttcctgctgt cctgcaaagc

541 tctggcctgt actcactcag ctccgtcgtg accgtgccat cttcatctct gggcactcag

601 acctacatct gtaatgtaaa ccacaagcct agcaatacta aggtcgataa gcgggtggaa

661 cccaagagct gcgacaagac tcacacttgt cccccatgcc ctgcccctga acttctgggc

721 ggtcccagcg tctttttgtt cccaccaaag cctaaagata ctctgatgat aagtagaaca

781 cccgaggtga catgtgttgt tgtagacgtt tcccacgagg acccagaggt taagttcaac

841 tggtacgttg atggagtcga agtacataat gctaagacca agcctagaga ggagcagtat

901 aatagtacat accgtgtagt cagtgttctc acagtgctgc accaagactg gctcaacggc
```

-continued

```
 961 aaagaataca aatgcaaagt gtccaacaaa gcactcccag cccctatcga gaagactatt

1021 agtaaggcaa aggggcagcc tcgtgaacca caggtgtaca ctctgccacc cagtagagag

1081 gaaatgacaa agaaccaagt ctcattgacc tgcctggtga aaggcttcta ccccagcgac

1141 atcgccgttg agtgggagag taacggtcag cctgagaaca attacaagac aacccccccca

1201 gtgctggata gtgacgggtc tttctttctg tacagtaagc tgactgtgga caagtcccgc

1261 tggcagcagg gtaacgtctt cagctgttcc gtgatgcacg aggcattgca caaccactac

1321 acccagaagt cactgagcct gagcccaggg aag
```

Protein Sequence Defining the Full Length Humanized Sh07F01 Hv3-48 Heavy Chain (Humanized Heavy Chain Variable Region and Human IgG1 Constant Region)

(SEQ ID NO: 164)

```
  1 evqlvesggg lvqpggslrl scaasgfdfs rhwmswvrqa pgkglewvse inpdsrtiny

 61 tpslkerfti srdnaknsly lqmnslraed tavyycarrv rihyygamds wgqgttvtvs

121 sastkgpsvf plapssksts ggtaalgclv kdyfpepvtv swnsgaltsg vhtfpavlqs

181 sglyslssvv tvpssslgtq tyicnvnhkp sntkvdkrve pkscdkthtc ppcpapellg

241 gpsvflfppk pkdtlmisrt pevtcvvvdv shedpevkfn wyvdgvevhn aktkpreeqy

301 nstyrvvsvl tvlhqdwlng keykckvsnk alpapiekti skakgqprep qvytlppsre

361 emtknqvslt clvkgfypsd iavewesngq pennykttpp vldsdgsffl yskltvdksr

421 wqqgnvfscs vmhealhnhy tqkslslspg k
```

Nucleic Acid Sequence Encoding the Full Length Humanized Sh07F01 Hv3-48 D28T T60A L63V E65G Heavy Chain (Humanized Heavy Chain Variable Region and Human IgG1 Constant Region)

(SEQ ID NO: 165)

```
   1 gaggttcagc tggtagaatc cggaggaggg ttggtccaac ctggtggatc actcagactt

  61 tcatgcgccg ccagcggctt taccttctca cgacattgga tgagctgggt ccggcaggct

 121 ccaggcaagg gcctcgagtg ggttagcgag atcaatccag acagcagaac cattaactat

 181 gcccccagtg tgaagggccg gttcaccata agccgtgata atgccaagaa ctccctgtac

 241 ttgcagatga actccttgcg cgctgaagat acagctgtgt actattgtgc aaggcgcgtg

 301 cgaatccact attacggggc aatggattct tggggccagg gtactaccgt gactgtgagt

 361 tctgcctcaa caaaaggacc aagtgtgttc ccactcgccc ctagcagcaa gagtacatcc

 421 gggggcactg cagcactcgg ctgcctcgtc aaggattatt ttccagagcc agtaaccgtg

 481 agctggaaca gtggagcact cacttctggt gtccatactt ttcctgctgt cctgcaaagc

 541 tctggcctgt actcactcag ctccgtcgtg accgtgccat cttcatctct gggcactcag

 601 acctacatct gtaatgtaaa ccacaagcct agcaatacta aggtcgataa gcgggtggaa

 661 cccaagagct gcgacaagac tcacacttgt cccccatgcc ctgcccctga acttctgggc

 721 ggtcccagcg tctttttgtt cccaccaaag cctaaagata ctctgatgat aagtagaaca

 781 cccgaggtga catgtgttgt tgtagacgtt tcccacgagg acccagaggt taagttcaac

 841 tggtacgttg atggagtcga agtacataat gctaagacca agcctagaga ggagcagtat

 901 aatagtacat accgtgtagt cagtgttctc acagtgctgc accaagactg gctcaacggc

 961 aaagaataca aatgcaaagt gtccaacaaa gcactcccag cccctatcga gaagactatt

1021 agtaaggcaa aggggcagcc tcgtgaacca caggtgtaca ctctgccacc cagtagagag

1081 gaaatgacaa agaaccaagt ctcattgacc tgcctggtga aaggcttcta ccccagcgac

1141 atcgccgttg agtgggagag taacggtcag cctgagaaca attacaagac aacccccccca

1201 gtgctggata gtgacgggtc tttctttctg tacagtaagc tgactgtgga caagtcccgc

1261 tggcagcagg gtaacgtctt cagctgttcc gtgatgcacg aggcattgca caaccactac
```

-continued 1321 acccagaagt cactgagcct gagcccaggg aag

Protein Sequence Defining the Full Length Humanized Sh07F01 Hv3-48 D28T T60A L63V E65G Heavy Chain (Humanized Heavy Chain Variable Region and Human IgG1 Constant Region)

(SEQ ID NO: 166)

1 evqlvesggg lvqpggslrl scaasgftfs rhwmswvrqa pgkglewvse inpdsrtiny 61 apsvkgrfti srdnaknsly lqmnslraed tavyycarrv rihyygamds wgqgttvtvs 121 sastkgpsvf plapssksts ggtaalgclv kdyfpepvtv swnsgaltsg vhtfpavlqs 181 sglyslssvv tvpssslgtq tyicnvnhkp sntkvdkrve pkscdkthtc ppcpapellg 241 gpsvflfppk pkdtlmisrt pevtcvvvdv shedpevkfn wyvdgvevhn aktkpreeqy 301 nstyrvvsvl tvlhqdwlng keykckvsnk alpapiekti skakgqprep qvytlppsre 361 emtknqvslt clvkgfypsd iavewesngq pennykttpp vldsdgsffl yskltvdksr 421 wqqgnvfscs vmhealhnhy tqkslslspg k Nucleic Acid Sequence Encoding the Full Length Humanized HE L 07F01 Kv1-9 Light Chain (Humanized Kappa Chain Variable Region and Human Constant Region)

(SEQ ID NO: 167)

1 gatatccagt tgactcagtc tcagtccttt gtgagtacat cagtgggcga cagggtcacc 61 gtgacctgcc gagcatcaca gaacgttgga agctctcttg tctggtatca gcaaaagcct 121 gggaagagcc ccaaaaccct catctattct gcttcctttc tgtactccgg cgtaccaagt 181 agattctctg gtagcggatc cgggacagag ttcactctca caattagcag tgtgcagcct 241 gaggatttcg ccgactactt ctgtcagcaa tacaataact atcccctgac ttttggtggc 301 ggcaccaaag tggaaatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt 601 ttgtctagtc ctgtcaccaa gtccttcaat aggggcgaat gt Protein Sequence Defining the Full Length Humanized HE L 07F01 Kv1-9 Light Chain (Humanized Kappa Chain Variable Region and Human Constant Region)

(SEQ ID NO: 168)

1 diqltqsqsf vstsvgdrvt vtcrasqnvg sslvwyqqkp gkspktliys asflysgvps 61 rfsgsgsgte ftltissvqp edfadyfcqq ynnypltfgg gtkveikrtv aapsvfifpp 121 sdeqlksgta svvcllnnfy preakvqwkv dnalqsgnsq esvteqdskd styslsstlt 181 lskadyekhk vyacevthqg lsspvtksfn rgec Nucleic Acid Sequence Encoding the Full Length Humanized sh07F01 Kv1-9 F1 Light Chain (Humanized Kappa Chain Variable Region and Human Constant Region)

(SEQ ID NO: 169)

1 gacattcagc tgactcagtc gccgtcgttt ttgtcggcgt ccgtgggtga cagagtgact 61 atcacatgtc gcgcttcgca aaacgtcgga tcatcgcttg tgtggtatca gcagaaaccc 121 ggtaaagccc ctaagaccct catctattca gcgtcatttc tgtatagcgg ggtcccctca 181 cggttcagcg gatccggctc cgggaccgag ttcacactca ctatttcgag cttgcagccg 241 gaagattttg caacgtacta ctgccagcaa tacaataact acccactcac gttcggaggg 301 ggaacgaagg tagagatcaa gcgcacagtt gctgccccca gcgtgttcat tttcccacct 361 agcgatgagc agctgaaaag cggtactgcc tctgtcgtat gcttgctcaa caacttttac 421 ccacgtgagg ctaaggtgca gtggaaagtg gataatgcac ttcaatctgg aaacagtcaa 481 gagtccgtga cagaacagga cagcaaagac tcaacttatt cactctcttc caccctgact 541 ctgtccaagg cagactatga aaaacacaag gtatacgcct gcgaggttac acaccagggt -continued

```
 601 ttgtctagtc ctgtcaccaa gtccttcaat aggggcgaat gt
```

Protein Sequence Defining the Full Length Humanized sh07F01 Kv1-9 F1 Light Chain (Humanized Kappa Chain Variable Region and Human Constant Region)

(SEQ ID NO: 170)

```
   1 diqltqspsf lsasvgdrvt itcrasqnvg sslvwyqqkp gkapktliys asflysgvps

  61 rfsgsgsgte ftltisslqp edfatyycqq ynnypltfgg gtkveikrtv aapsvfifpp

 121 sdeqlksgta svvcllnnfy preakvqwkv dnalqsgnsq esvteqdskd styslsstlt

 181 lskadyekhk vyacevthqg lsspvtksfn rgec
```

Nucleic Acid Sequence Encoding the Full Length Humanized Sh29B06 Hv4-59 Heavy Chain (Humanized Heavy Chain Variable Region and Human IgG1 Constant Region)

(SEQ ID NO: 171)

```
   1 caagttcagc tgcaagaatc cggaccagga ttggtcaaac cttcagagac actcagcctg

  61 acttgcaccg tgagcggtgg cagcatatcc tccggttatt ggaactggat ccggcagcca

 121 ccaggcaagg gcctcgagtg gattggctac atcagctata gcgggaaaac ctattacaac

 181 cccagtctga agagccgagt gaccataagc gtcgatacaa gtaagaacca gttctccctg

 241 aagctctcat ccgtgaccgc cgctgataca gctgtgtact attgtgcaag gtcaaagtat

 301 gactacgcaa tggactattg gggccagggt actctggtga ctgtgagttc tgcctcaaca

 361 aaaggaccaa gtgtgttccc actcgcccct agcagcaaga gtacatccgg gggcactgca

 421 gcactcggct gcctcgtcaa ggattatttt ccagagccag taaccgtgag ctggaacagt

 481 ggagcactca cttctggtgt ccatactttt cctgctgtcc tgcaaagctc tggcctgtac

 541 tcactcagct ccgtcgtgac cgtgccatct tcatctctgg gcactcagac ctacatctgt

 601 aatgtaaacc acaagcctag caatactaag gtcgataagc gggtggaacc caagagctgc

 661 gacaagactc acacttgtcc cccatgccct gcccctgaac ttctgggcgg tcccagcgtc

 721 tttttgttcc caccaaagcc taaagatact ctgatgataa gtagaacacc cgaggtgaca

 781 tgtgttgttg tagacgtttc ccacgaggac ccagaggtta agttcaactg gtacgttgat

 841 ggagtcgaag tacataatgc taagaccaag cctagagagg agcagtataa tagtacatac

 901 cgtgtagtca gtgttctcac agtgctgcac caagactggc tcaacggcaa agaatacaaa

 961 tgcaaagtgt ccaacaaagc actcccagcc cctatcgaga agactattag taaggcaaag

1021 gggcagcctc gtgaaccaca ggtgtacact ctgccaccca gtagagagga aatgacaaag

1081 aaccaagtct cattgacctg cctggtgaaa ggcttctacc ccagcgacat cgccgttgag

1141 tgggagagta acggtcagcc tgagaacaat tacaagacaa ccccccccagt gctggatagt

1201 gacgggtctt tctttctgta cagtaagctg actgtggaca agtcccgctg gcagcagggt

1261 aacgtcttca gctgttccgt gatgcacgag gcattgcaca accactacac ccagaagtca

1321 ctgagcctga gcccagggaa g
```

Protein Sequence Defining the Full Length Humanized Sh29B06 Hv4-59 Heavy Chain (Humanized Heavy Chain Variable Region and Human IgG1 Constant Region)

(SEQ ID NO: 172)

```
   1 qvqlqesgpg lvkpsetlsl tctvsggsis sgywnwirqp pgkglewigy isysgktyyn

  61 pslksrvtis vdtsknqfsl klssvtaadt avyycarsky dyamdywgqg tlvtvssast

 121 kgpsvfplap sskstsggta algclvkdyf pepvtvswns galtsgvhtf pavlqssgly

 181 slssvvtvps sslgtqtyic nvnhkpsntk vdkrvepksc dkthtcppcp apellggpsv

 241 flfppkpkdt lmisrtpevt cvvvdvshed pevkfnwyvd gvevhnaktk preeqynsty

 301 rvvsvltvlh qdwlngkeyk ckvsnkalpa piektiskak gqprepqvyt lppsreemtk

 361 nqvsltclvk gfypsdiave wesngqpenn ykttppvlds dgsfflyskl tvdksrwqqg

 421 nvfscsvmhe alhnhytqks lslspgk
```

-continued

Nucleic Acid Sequence Encoding the Full Length Humanized Hu29B06 Hv4-59 Heavy Chain (Humanized Heavy Chain Variable Region and Human IgG1 Constant Region)

(SEQ ID NO: 173)

```
   1 caagttcagc tgcaagaatc cggaccagga ttggtcaaac ccagcgaaac actctctctt

  61 acatgcaccg tgagcggcga ctctatcacc tcagggtatt ggaattggat tcggaaaccc

 121 ccaggcaaga agctcgagta catgggttac atcagttaca gcgggaaaac ctactataac

 181 cccagtctga agagcagaat caccataagc cgtgatacct ctaagaacca gtactccctg

 241 aagctgagtt ccgtaacagc agctgataca gctgtgtact attgtgcaag gagtaagtat

 301 gactacgcaa tggactattg gggccagggt actcttgtga ctgtgagttc tgcctcaaca

 361 aaaggaccaa gtgtgttccc actcgcccct agcagcaaga gtacatccgg gggcactgca

 421 gcactcggct gcctcgtcaa ggattatttt ccagagccag taaccgtgag ctggaacagt

 481 ggagcactca cttctggtgt ccatactttt cctgctgtcc tgcaaagctc tggcctgtac

 541 tcactcagct ccgtcgtgac cgtgccatct tcatctctgg gcactcagac ctacatctgt

 601 aatgtaaacc acaagcctag caatactaag gtcgataagc gggtggaacc caagagctgc

 661 gacaagactc acacttgtcc cccatgccct gcccctgaac ttctgggcgg tcccagcgtc

 721 tttttgttcc caccaaagcc taaagatact ctgatgataa gtagaacacc cgaggtgaca

 781 tgtgttgttg tagacgtttc ccacgaggac ccagaggtta agttcaactg gtacgttgat

 841 ggagtcgaag tacataatgc taagaccaag cctagagagg agcagtataa tagtacatac

 901 cgtgtagtca gtgttctcac agtgctgcac caagactggc tcaacggcaa agaatacaaa

 961 tgcaaagtgt ccaacaaagc actcccagcc cctatcgaga agactattag taaggcaaag

1021 gggcagcctc gtgaaccaca ggtgtacact ctgccaccca gtagagagga aatgacaaag

1081 aaccaagtct cattgacctg cctggtgaaa ggcttctacc ccagcgacat cgccgttgag

1141 tgggagagta acggtcagcc tgagaacaat tacaagacaa cccccccagt gctggatagt

1201 gacgggtctt tctttctgta cagtaagctg actgtggaca agtcccgctg gcagcagggt

1261 aacgtcttca gctgttccgt gatgcacgag gcattgcaca accactacac ccagaagtca

1321 ctgagcctga gcccagggaa g
```

Protein Sequence Defining the Full Length Humanized Hu29B06 Hv4-59 Heavy Chain (Humanized Heavy Chain Variable Region and Human IgG1 Constant Region)

(SEQ ID NO: 174)

```
   1 qvqlqesgpg lvkpsetlsl tctvsgdsit sgywnwirkp pgkkleymgy isysgktyyn

  61 pslksritis rdtsknqysl klssvtaadt avyycarsky dyamdywgqg tlvtvssast

 121 kgpsvfplap sskstsggta algclvkdyf pepvtvswns galtsgvhtf pavlqssgly

 181 slssvvtvps sslgtqtyic nvnhkpsntk vdkrvepksc dkthtcppcp apellggpsv

 241 flfppkpkdt lmisrtpevt cvvvdvshed pevkfnwyvd gvevhnaktk preeqynsty

 301 rvvsvltvlh qdwlngkeyk ckvsnkalpa piektiskak gqprepqvyt lppsreemtk

 361 nqvsltclvk gfypsdiave wesngqpenn ykttppvlds dgsfflyskl tvdksrwqqg

 421 nvfscsvmhe alhnhytqks lslspgk
```

Nucleic Acid Sequence Encoding the Full Length Humanized Hu29B06 Hv4-59 D27G T30S M48I I67V Y78F Heavy Chain (Humanized Heavy Chain Variable Region and Human IgG1 Constant Region)

(SEQ ID NO: 175)

```
   1 caagttcagc tgcaagaatc cggaccagga ttggtcaaac cttcagagac actcagcctg

  61 acttgcaccg tgagcggtgg cagcatatcc tccggttatt ggaactggat ccggaagcca

 121 ccaggcaaga agctcgagta cattggctac atcagctata gcgggaaaac ctattacaac

 181 cccagtctga agagccgagt gaccataagc agggatacaa gtaagaacca gttctccctg

 241 aagctctcat ccgtgaccgc cgctgataca gctgtgtact attgtgcaag gtcaaagtat
```

-continued

```
 301 gactacgcaa tggactattg gggccagggt actctggtga ctgtgagttc tgcctcaaca
 361 aaaggaccaa gtgtgttccc actcgcccct agcagcaaga gtacatccgg gggcactgca
 421 gcactcggct gcctcgtcaa ggattatttt ccagagccag taaccgtgag ctggaacagt
 481 ggagcactca cttctggtgt ccatactttt cctgctgtcc tgcaaagctc tggcctgtac
 541 tcactcagct ccgtcgtgac cgtgccatct tcatctctgg gcactcagac ctacatctgt
 601 aatgtaaacc acaagcctag caatactaag gtcgataagc gggtggaacc caagagctgc
 661 gacaagactc acacttgtcc cccatgccct gcccctgaac ttctgggcgg tcccagcgtc
 721 tttttgttcc caccaaagcc taaagatact ctgatgataa gtagaacacc cgaggtgaca
 781 tgtgttgttg tagacgtttc ccacgaggac ccagaggtta agttcaactg gtacgttgat
 841 ggagtcgaag tacataatgc taagaccaag cctagagagg agcagtataa tagtacatac
 901 cgtgtagtca gtgttctcac agtgctgcac caagactggc tcaacggcaa agaatacaaa
 961 tgcaaagtgt ccaacaaagc actcccagcc cctatcgaga agactattag taaggcaaag
1021 gggcagcctc gtgaaccaca ggtgtacact ctgccaccca gtagagagga aatgacaaag
1081 aaccaagtct cattgacctg cctggtgaaa ggcttctacc ccagcgacat cgccgttgag
1141 tgggagagta acggtcagcc tgagaacaat tacaagacaa cccccccagt gctggatagt
1201 gacgggtctt tctttctgta cagtaagctg actgtggaca agtcccgctg gcagcagggt
1261 aacgtcttca gctgttccgt gatgcacgag gcattgcaca accactacac ccagaagtca
1321 ctgagcctga gcccagggaa g
```

Protein Sequence Defining the Full Length Humanized Hu29B06 Hv4-59 D27G T30S M48I I67V Y78F Heavy Chain (Humanized Heavy Chain Variable Region and Human IgG1 Constant Region)

(SEQ ID NO: 176)

```
  1 qvqlqesgpg lvkpsetlsl tctvsggsis sgywnwirkp pgkkleyigy isysgktyyn
 61 pslksrvtis rdtsknqfsl klssvtaadt avyycarsky dyamdywgqg tlvtvssast
121 kgpsvfplap sskstsggta algclvkdyf pepvtvswns galtsgvhtf pavlqssgly
181 slssvvtvps sslgtqtyic nvnhkpsntk vdkrvepksc dkthtcppcp apellggpsv
241 flfppkpkdt lmisrtpevt cvvvdvshed pevkfnwyvd gvevhnaktk preeqynsty
301 rvvsvltvlh qdwlngkeyk ckvsnkalpa piektiskak gqprepqvyt lppsreemtk
361 nqvsltclvk gfypsdiave wesngqpenn ykttppvlds dgsfflyskl tvdksrwqqg
421 nvfscsvmhe alhnhytqks lslspgk
```

Nucleic Acid Sequence Encoding the Full Length Humanized Sh29B06 Kv2-28 Light Chain (Humanized Kappa Chain Variable Region and Human Constant Region)

(SEQ ID NO: 177)

```
  1 gatatcgtta tgacccagag cccacttagt ttgcctgtta ctcctggcga gcctgccagt
 61 atttcttgcc gtgctagcga aatcgtggat aactttggta tatcattcat gaattggtat
121 ctccaaaaac ctggccaaag cccccagctc cttatctacg ccgctagcaa ccaggggtcc
181 ggggtacctg atagattttc aggcagcggc tctggaaccg acttcacact gaagatttcc
241 cgggtggagg ccgaggacgt gggcgtgtac tattgtcaac agtccaagga agtccctccc
301 actttcggcg gtgggacaaa ggttgagatt aagcgcacag ttgctgcccc cagcgtgttc
361 attttcccac ctagcgatga gcagctgaaa agcggtactg cctctgtcgt atgcttgctc
```

-continued

```
421 aacaactttt acccacgtga ggctaaggtg cagtggaaag tggataatgc acttcaatct

481 ggaaacagtc aagagtccgt gacagaacag gacagcaaag actcaactta ttcactctct

541 tccaccctga ctctgtccaa ggcagactat gaaaaacaca aggtatacgc ctgcgaggtt

601 acacaccagg gtttgtctag tcctgtcacc aagtccttca ataggggcga atgt
```

Protein Sequence Defining the Full Length Humanized Sh29B06 Kv2-28 Light Chain (Humanized Kappa Chain Variable Region and Human Constant Region)

(SEQ ID NO: 178)

```
  1 divmtqspls lpvtpgepas iscraseivd nfgisfmnwy lqkpgqspql liyaasnqgs

 61 gvpdrfsgsg sgtdftlkis rveaedvgvy ycqqskevpp tfgggtkvei krtvaapsvf

121 ifppsdeqlk sgtasvvcll nnfypreakv qwkvdnalqs gnsqesvteq dskdstysls

181 stltlskady ekhkvyacev thqglsspvt ksfnrgec
```

For convenience, Table 18 provides a concordance chart showing the SEQ ID NO. of each sequence discussed in this Example.

TABLE 18

| SEQ ID NO. | Nucleic Acid or Protein |
|---|---|
| 150 | Human IgG1 constant-nucleic acid |
| 151 | Human IgG1 constant-protein |
| 152 | Human Kappa constant (used for chimeric antibodies)-nucleic acid |
| 153 | Human Kappa constant (used for humanized antibodies)-nucleic acid |
| 154 | Human Kappa constant (used for chimeric and humanized antibodies)-protein |
| 155 | Chimeric 07F01 C102S Mouse Heavy Chain Variable + Human IgG1 constant-nucleic acid |
| 156 | Chimeric 07F01 C102S Mouse Heavy Chain Variable + Human IgG1 constant-protein |
| 157 | Chimeric 07F01 Mouse Light Chain Variable + Human Kappa constant-nucleic acid |
| 158 | Chimeric 07F01 Mouse Light Chain Variable + Human Kappa constant-protein |
| 159 | Chimeric 29B06 Mouse Heavy Chain Variable + Human IgG1 constant-nucleic acid |
| 160 | Chimeric 29B06 Mouse Heavy Chain Variable + Human IgG1 constant-protein |
| 161 | Chimeric 29B06 Mouse Light Chain Variable + Human Kappa constant-nucleic acid |
| 162 | Chimeric 29B06 Mouse Light Chain Variable + Human Kappa constant-protein |
| 163 | Humanized Sh07F01 Hv3-48 Heavy Human Variable + Human IgG1 constant-nucleic acid |
| 164 | Humanized Sh07F01 Hv3-48 Heavy Human Variable + Human IgG1 constant-protein |
| 165 | Humanized Sh07F01 Hv3-48 D28T T60A L63V E65G Heavy Human Variable + Human IgG1 constant-nucleic acid |
| 166 | Humanized Sh07F01 Hv3-48 D28T T60A L63V E65G Heavy Human Variable + Human IgG1 constant-protein |
| 167 | Humanized HE L 07F01 Kv1-9 Human Variable + Human Kappa constant-nucleic acid |
| 168 | Humanized HE L 07F01 Kv1-9 Human Variable + Human Kappa constant-protein |
| 169 | Humanized sh07F01 Kv1-9 F1 Human Variable + Human Kappa constant-nucleic acid |
| 170 | Humanized sh07F01 Kv1-9 F1 Human Variable + Human Kappa constant-protein |
| 171 | Humanized Sh29B06 Hv4-59 Heavy Human Variable + Human IgG1 constant-nucleic acid |
| 172 | Humanized Sh29B06 Hv4-59 Heavy Human Variable + Human IgG1 constant-protein |
| 173 | Humanized Hu29B06 Hv4-59 Heavy Human Variable + Human IgG1 constant-nucleic acid |
| 174 | Humanized Hu29B06 Hv4-59 Heavy Human Variable + Human IgG1 constant-protein |
| 175 | Humanized Hu29B06 Hv4-59 D27G T30S M48I I67V Y78F Heavy Human Variable + Human IgG1 constant-nucleic acid |
| 176 | Humanized Hu29B06 Hv4-59 D27G T30S M48I I67V Y78F Heavy Human Variable + Human IgG1 constant-protein |
| 177 | Humanized Sh29B06 Kv2-28 Human Variable + Human Kappa constant-nucleic acid |
| 178 | Humanized Sh29B06 Kv2-28 Human Variable + Human Kappa constant-protein |

Table 19 below shows antibodies containing chimeric immunoglobulin heavy and light chains and each of the possible combinations of the full-length chimeric or humanized immunoglobulin heavy and light chains.

TABLE 19

| Antibody Name | Light Chain | Heavy Chain |
|---|---|---|
| Sh07F01-2 | Chimeric 07F01 Kappa (SEQ ID NO: 158) | Chimeric 07F01 C102S Heavy IgG1 (SEQ ID NO: 156) |
| Sh07F01-43 | HE L 07F01 Kv1-9 Kappa (SEQ ID NO: 168) | Sh07F01 Hv3-48 IgG1 (SEQ ID NO: 164) |
| Sh07F01-62 | HE L 07F01 Kv1-9 Kappa (SEQ ID NO: 168) | Sh07F01 Hv3-48 D28T T60A L63V E65G IgG1 (SEQ ID NO: 166) |
| Sh07F01-69 | Sh07F01 Kv1-9 F1 Kappa (SEQ ID NO: 170) | Sh07F01 Hv3-48 IgG1 (SEQ ID NO: 164) |
| Sh07F01-83 | Sh07F01 Kv1-9 F1 Kappa (SEQ ID NO: 170) | Sh07F01 Hv3-48 D28T T60A L63V E65G IgG1 (SEQ ID NO: 166) |
| Sh07F01-99 | Chimeric 07F01 Kappa (SEQ ID NO: 158) | Sh07F01 Hv3-48 IgG1 (SEQ ID NO: 164) |
| Sh07F01-100 | Chimeric 07F01 Kappa (SEQ ID NO: 158) | Sh07F01 Hv3-48 D28T T60A L63V E65G IgG1 (SEQ ID NO: 166) |
| Sh07F01-101 | HE L 07F01 Kv1-9 Kappa (SEQ ID NO: 168) | Chimeric 07F01 C102S Heavy IgG1 (SEQ ID NO: 156) |
| Sh07F01-102 | Sh07F01 Kv1-9 F1 Kappa (SEQ ID NO: 170) | Chimeric 07F01 C102S Heavy IgG1 (SEQ ID NO: 156) |
| Sh29B06-1 | Chimeric 29B06 Kappa (SEQ ID NO: 162) | Chimeric 29B06 Heavy IgG1 (SEQ ID NO: 160) |
| Sh29B06-2 | Chimeric 29B06 Kappa (SEQ ID NO: 162) | Hu29B06 Hv4-59 IgG1 (SEQ ID NO: 174) |
| Sh29B06-4 | Chimeric 29B06 Kappa (SEQ ID NO: 162) | Sh29B06 Hv4-59 IgG1 (SEQ ID NO: 172) |
| Sh29B06-9 | Sh29B06 Kv2-28 Kappa (SEQ ID NO: 178) | Chimeric 29B06 Heavy IgG1 (SEQ ID NO: 160) |
| Sh29B06-23 | Sh29B06 Kv2-28 Kappa (SEQ ID NO: 178) | Hu29B06 Hv4-59 IgG1 (SEQ ID NO: 174) |
| Sh29B06-25 | Sh29B06 Kv2-28 Kappa (SEQ ID NO: 178) | Sh29B06 Hv4-59 IgG1 (SEQ ID NO: 172) |
| Sh29B06-78 | Sh29B06 Kv2-28 Kappa (SEQ ID NO: 178) | Hu29B06 Hv4-59 D27G T30S M48I I67V Y78F IgG1 (SEQ ID NO: 176) |
| Sh29B06-84 | Chimeric 29B06 Kappa (SEQ ID NO: 162) | Hu29B06 Hv4-59 D27G T30S M48I I67V Y78F IgG1 (SEQ ID NO: 176) |

The antibody constructs containing the full length chimeric heavy and light chains are designated below:

Chimeric 07F01 C102S=Full Length Chimeric 07F01 C102S Heavy Chain (Mouse Variable Region with C102S mutation and Human IgG1 Constant Region) (SEQ ID NO: 156) plus Full Length Chimeric 07F01 Light Chain (Mouse Variable Region and Human Kappa Constant Region) (SEQ ID NO: 158)

Chimeric 29B06=Full Length Chimeric 29B06 Heavy Chain (Mouse Variable Region and Human IgG1 Constant Region) (SEQ ID NO: 160) plus Full Length Chimeric 29B06 Light Chain (Mouse Variable Region and Human Kappa Constant Region) (SEQ ID NO: 162)

Two of the possible antibody constructs containing the full length immunoglobulin heavy and light chains containing humanized variable regions are designated below:

Sh07F01-62=Humanized Sh07F01 Hv3-48 D28T T60A L63V E65G Heavy Chain Variable Region and Human IgG1 Constant Region (SEQ ID NO: 166) plus HE L 07F01 Kv1-9 Light Chain Variable Region and Human Kappa Constant Region (SEQ ID NO: 168)

Sh29B06-78=Humanized Hu29B06 Hv4-59 D27G T30S M48I I67V Y78F Heavy Chain Variable Region and Human IgG1 Constant Region (SEQ ID NO: 176) plus Sh29B06 Kv2-28 Light Chain Variable Region and Human Kappa Constant Region (SEQ ID NO: 178)

B. Binding Affinities of Humanized and Chimeric Anti-RON Monoclonal Antibodies

The binding affinities and kinetics of interaction of monoclonal antibodies produced in Example 14 against recombinant human RON SEMA and PSI domains (rhRON SEMA+PSI) (R&D Systems, Inc., Minneapolis, Minn.) were measured by surface plasmon resonance using a Biacore T100 (Biacore (GE Healthcare), Piscataway, N.J.) instrument.

Goat anti-human IgG Fc (Jackson ImmunoResearch, Catalog No. 109-005-098) was immobilized on carboxymethylated dextran CM4 sensor chips (Biacore) by amine coupling (Biacore) using a standard coupling protocol according to the vendor's instructions. The analyses were performed at 37° C. using PBS (Invitrogen) containing 0.05% surfactant P20 (Biacore) as running buffer.

The antibodies were captured in individual flow cells at a flow rate of 60 µl/minute. Injection time was varied for each antibody to yield an $R_{max}$ between 30 and 60 RU. Buffer or rhRON SEMA+PSI diluted in running buffer was injected sequentially over a reference surface (no antibody captured) and the active surface (antibody to be tested) for 300 seconds at 60 µl/minute. The dissociation phase was monitored for up to 1200 seconds. The surface was then regenerated with two 60 second injections of Glycine pH 2.25 (made from Glycine pH 2.0 (Biacore) and pH 2.5 (Biacore)) at 60 µl/minute. For the initial screening, only one or two concentrations of rhRON SEMA+PSI were tested, typically 10.0 and 2.5 nM (results are summarized in Table 20).

Kinetic parameters were determined using the kinetic function of the BIAevaluation software (Biacore) with double reference subtraction. Kinetic parameters for each antibody, $k_a$ (association rate constant), $k_d$ (dissociation rate constant) and $K_D$ (equilibrium dissociation constant) were determined. Certain monoclonal antibodies were screened using cell culture media supernatant containing secreted antibody, and kinetic values of the monoclonal antibodies on rhRON SEMA+PSI at 37° C. are summarized in Table 20.

TABLE 20

| Antibody | ka (1/Ms) | kd (1/s) | KD (M) | n |
|---|---|---|---|---|
| Sh07F01-2 | 2.0E+06 | 7.3E−04 | 3.8E−10 | 3 |
| Sh07F01-62 | 3.9E+06 | 1.4E−03 | 3.6E−10 | 2 |
| Sh07F01-69 | 2.3E+06 | 1.2E−03 | 5.6E−10 | 2 |
| Sh07F01-76 | 2.3E+06 | 1.3E−03 | 5.7E−10 | 2 |
| Sh07F01-83 | 2.6E+06 | 1.4E−03 | 5.4E−10 | 2 |
| Sh29B06-1 | 6.7E+05 | 7.6E−04 | 1.1E−09 | 3 |
| Sh29B06-9 | 8.7E+05 | 2.2E−04 | 2.6E−10 | 1 |
| Sh29B06-23 | 7.8E+05 | 4.8E−04 | 6.4E−10 | 4 |
| Sh29B06-25 | | No Binding | | |

The results in Table 20 demonstrate that the chimeric and each of the humanized antibodies, except Sh29B06-25, have fast association rates ($k_a$), very slow disassociation rates ($k_d$) and very high affinities ($K_D$). In particular, the antibodies have affinities ranging from about 260 pM to about 1.1 nM. No binding was observed for Sh29B06-25. Because Sh29B06-25 does not bind rhRON SEMA+PSI and Sh29B06-23 does, one or more of the back mutations present in the heavy chain of Sh29B06-23 appear to be required for binding with high affinity.

The binding affinities and kinetics of certain purified monoclonal antibodies were also determined. To further characterize certain antibodies, the surface plasmon resonance experiments described above were conducted using concentrations of rhRON SEMA+PSI between 0.3125 nM and 10.0 nM (a 2-fold serial dilution).

The kinetic values of certain purified monoclonal antibodies (i.e., Sh07F01-62 and Sh29B06-78) on rhRON SEMA+PSI at 25° C. and 37° C. are summarized in Table 21.

TABLE 21

| Antibody Binding to rhRON SEMA + PSI | | | | | | | | |
|---|---|---|---|---|---|---|---|---|
| | Measurements at 25° C. | | | | Measurements at 37° C. | | | |
| Antibody | ka (1/Ms) | kd (1/s) | KD (M) | n | ka (1/Ms) | kd (1/s) | KD (M) | n |
| Sh07F01-2 | 1.2E+06 | 9.8E−05 | 8.2E−11 | 9 | 1.7E+06 | 5.3E−04 | 3.1E−10 | 9 |
| Sh07F01-43 | 1.2E+06 | 1.1E−04 | 9.0E−11 | 3 | 1.8E+06 | 5.6E−04 | 3.0E−10 | 3 |
| Sh07F01-62 | 1.8E+06 | 1.6E−04 | 8.5E−11 | 4 | 2.8E+06 | 6.9E−04 | 2.5E−10 | 4 |
| Sh07F01-69 | 1.1E+06 | 1.4E−04 | 1.2E−10 | 2 | 2.5E+06 | 7.8E−04 | 3.0E−10 | 2 |
| Sh07F01-76 | 9.8E+05 | 1.3E−04 | 1.3E−10 | 2 | 2.4E+06 | 7.9E−04 | 3.3E−10 | 2 |
| Sh07F01-83 | 1.6E+06 | 1.8E−04 | 1.1E−10 | 2 | 3.2E+06 | 7.9E−04 | 2.4E−10 | 2 |
| Sh29B06-1 | 5.3E+05 | 2.0E−04 | 3.6E−10 | 6 | 8.2E+05 | 7.0E−04 | 8.6E−10 | 5 |
| Sh29B06-23 | 6.7E+05 | 9.5E−05 | 1.4E−10 | 4 | 7.3E+05 | 3.3E−04 | 4.6E−10 | 5 |
| Sh29B06-78 | 7.5E+05 | 3.9E−05 | 5.2E−11 | 7 | 1.0E+06 | 1.1E−04 | 1.1E−10 | 9 |

The results in Table 21 demonstrate the purified antibodies have affinities ranging from about 52 pM to 360 pM when tested at 25° C. or about 110 pM to about 860 pM when tested at 37° C.

Binding to cell surface human wild-type RON and the delta 160 RON variant by antibodies 07F01, Sh07F01-62, 29B06, and Sh29B06-78 was measured at 4° C., using Fluorescence Activated Cell Sorting (FACS). PC3 cells expressing the human wild-type RON, and HT29 cells expressing the delta 160 variant, were harvested using cell dissociation buffer (Invitrogen), washed twice with FACS buffer (PBS with 0.5% BSA), and treated 10 minutes with Cyto Q Antibody diluent and FC receptor block (Innovex Biosciences, Richmond, Calif.). Purified antibodies were diluted in FACS buffer over a concentration range from 0.01 nM to 25 nM. Cells were incubated with 100 µl of antibody for one hour, washed with FACS buffer three times, and incubated for 45 minutes with goat anti-mouse PE-conjugated antibody (Jackson ImmunoResearch Laboratories, West Grove, Pa.) or donkey anti-human PE-conjugated antibody (Jackson ImmunoResearch Laboratories, West Grove, Pa.). Cells were washed three times with FACS buffer, resuspended in 300 µl of FACS buffer, and analyzed using a Beckman Coulter Cytomics FC 500 FACS instrument. All four antibodies were compared in the same experiment. Results are summarized in Table 22.

TABLE 22

| | 07F01 | Sh07F01-62 | 29B06 | Sh29B06-78 |
|---|---|---|---|---|
| Human RON - $K_D$ (nM) | 0.053 | 0.043 | 0.136 | 0.090 |
| Human RON - $K_D$ range (nM) | 0.036 to 0.069 | 0.026 to 0.060 | 0.083 to 0.190 | 0.063 to 0.117 |
| Delta 160 RON - $K_D$ (nM) | 0.100 | 0.118 | 0.167 | 0.239 |
| Delta 160 RON - $K_D$ range (nM) | 0.071 to 0.129 | 0.045 to 0.191 | 0.066 to 0.267 | 0.202 to 0.277 |

The results in Table 22 demonstrate that the humanized antibodies Sh07F01-62 and Sh29B06-78 retain their ability to bind both wild-type RON and the delta 160 RON variant on the cell surface with affinities equivalent to their murine antibody counterparts (i.e., 07F01 and 29B06, respectively).

C. Comparison of Other Anti-RON Antibodies

Three antibodies that inhibit the function of human RON were constructed and expressed using published information. One antibody, referred to as 1P3B2-BIIB Ab, was constructed based on the disclosure of Huet et al., U.S. Patent Publication No. 2009/0226442 (Biogen Idec, Inc.). Two additional antibodies, referred to as RON6 and RON8, were constructed based on the disclosure of Pereira et al., U.S. Patent Publication No. 2009/0136510 (Imclone Systems, Inc.).

Kinetic parameters for the 1P3B2-BIIB Ab, RON6, and RON8 antibodies on rhRON SEMA+PSI at 25° C. and 37° C. were determined by Biacore as described above (See Section B. Binding Affinities of Humanized and Chimeric Anti-RON Monoclonal Antibodies). The kinetic values for each antibody are summarized in Table 23.

TABLE 23

| Antibody Binding to rhRON SEMA + PSI | | | | | | | | |
|---|---|---|---|---|---|---|---|---|
| | Measurements at 25° C. | | | | Measurements at 37° C. | | | |
| Antibody | ka (1/Ms) | kd (1/s) | KD (M) | n | ka (1/Ms) | kd (1/s) | KD (M) | n |
| Sh29B06-78 | 6.8E+05 | 3.1E−05 | 4.8E−11 | 6 | 9.6E+05 | 1.0E−04 | 1.1E−10 | 8 |
| Sh07F01-62 | 1.8E+06 | 1.6E−04 | 8.5E−11 | 4 | 2.8E+06 | 6.9E−04 | 2.5E−10 | 4 |
| 1P3B2-BIIB | 1.5E+06 | 1.2E−03 | 8.0E−10 | 1 | 2.2E+07 | 2.6E−02 | 1.2E−09 | 1 |
| RON6 | 2.3E+06 | 2.6E−03 | 1.1E−09 | 1 | 1.9E+10 | 1.9E−01 | 1.0E−09 | 1 |
| RON8 | 1.2E+06 | 6.8E−04 | 6.7E−10 | 3 | 7.0E+06 | 2.5E−03 | 9.2E−10 | 3 |

The results in Table 23 demonstrate that the overall equilibrium dissociation constant ($K_D$) for Sh29B06-78 and Sh07F01-62 were smaller (i.e., higher affinity) than the $K_D$ for 1P3B2-BIIB, RON6, and RON8 at both 25° C. and 37° C. The $K_D$ of 1P3B2-BIIB, RON6, and RON8 antibodies can also be compared with other humanized 29B06 or 07F01 variants by comparing Tables 21 and 23.

Therefore, the binding affinities of Sh29B06-78 and Sh07F01-62 are significantly higher than the affinities of 1P3B2-BIIB, RON6, and RON8 antibodies as disclosed herein.

Example 15

Inhibition of MSP-RON Binding

The chimeric and humanized antibodies produced in Example 14 were tested for inhibition of MSP binding to hRON SEMA+PSI, as measured by electrochemiluminescence (ECL) assay as described in Example 3. The antibodies (concentration range: 0.006-10 μg/mL) were incubated for 45 minutes at room temperature.

The MSP-hRON binding interaction was inhibited by the chimeric and humanized antibodies listed in Table 24, which were tested in this assay. The $IC_{50}$ for the antibodies (IgG1) are shown in Table 24.

TABLE 24

| Antibody | Mean $IC_{50}$ | Std Dev of $IC_{50}$ | N |
|---|---|---|---|
| Sh29B06-1 | 1.73 | 1.24 | 8 |
| Sh29B06-23 | 1.24 | 1.57 | 9 |
| Sh29B06-78 | 0.41 | 0.24 | 8 |
| Sh07F01-2 | 0.91 | 1.42 | 8 |
| Sh07F01-43 | 0.22 | 0.09 | 2 |
| Sh07F01-62 | 0.32 | 0.12 | 6 |
| Sh07F01-69 | 0.28 | 0.18 | 2 |
| Sh07F01-76 | 0.38 | 0.33 | 2 |
| Sh07F01-83 | 0.33 | 0.24 | 2 |

The results in Table 24 demonstrate that the chimeric and humanized anti-RON antibodies listed in Table 24 (i.e., Sh29B06-1, Sh29B06-23, Sh29B06-78, Sh07F01-2, Sh07F01-43, Sh07F01-62, Sh07F01-69, Sh07F01-76, and Sh07F01-83) retain the ability to block MSP binding to hRON SEMA+PSI with high potency.

Example 16

Inhibition of Downstream Signaling by Anti-RON Antibodies

The chimeric and humanized anti-RON antibodies produced in Example 14 were tested for their ability to inhibit MSP-induced phosphorylation of ERK, a RON downstream signaling molecule, using the cell-based assay described in Example 3. The antibodies (concentration range: 0.006-10 μg/mL) in RPMI were added to the cells and incubated for one hour at 37° C. The IC50s of ERK phosphorylation inhibition by the chimeric and humanized anti-RON antibodies tested in this assay are shown in Table 25.

TABLE 25

| Antibody | Mean $IC_{50}$ | Std Dev of $IC_{50}$ | N |
|---|---|---|---|
| Sh29B06-1 | 0.10 | 0.10 | 6 |
| Sh29B06-23 | 0.11 | 0.08 | 10 |
| Sh29B06-78 | 0.13 | 0.08 | 5 |
| Sh07F01-2 | 0.06 | 0.06 | 7 |
| Sh07F01-43 | 0.02 | 0.00 | 3 |
| Sh07F01-62 | 0.03 | 0.03 | 2 |
| Sh07F01-69 | 0.05 | 0.02 | 2 |
| Sh07F01-76 | 0.10 | 0.03 | 2 |
| Sh07F01-83 | 0.03 | 0.02 | 2 |

The results in Table 25 demonstrate that the chimeric and humanized anti-RON antibodies listed in Table 25 (i.e., Sh29B06-1, Sh29B06-23, Sh29B06-78, Sh07F01-2, Sh07F01-43, Sh07F01-62, Sh07F01-69, Sh07F01-76, and Sh07F01-83) inhibit MSP-induced ERK phosphorylation in T47D breast cancer cell line with high potency.

Example 17

Inhibition of MSP-Dependent Cell Migration

Figure 16:
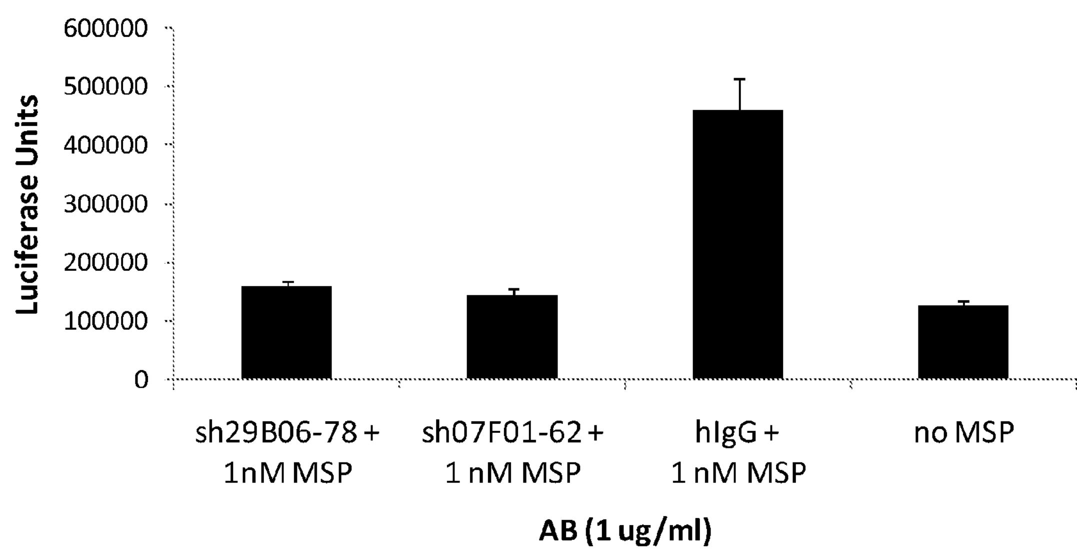
FIG. 16 is a histogram summarizing results from an experiment measuring inhibition of MSP induced HPAF-II cell migration by anti-RON antibodies Sh29B06-78 and Sh07F01-62, an IgG negative control (human IgG), and a no MSP control by transwell assay.

Humanized antibodies sh29B06-78 and sh07F01-62 as produced in Example 14 were tested for their ability to inhibit MSP-induced cell migration as described in Example 10. In this example, antibodies were added at a concentration of 1 μg/ml and serially diluted at a 1:5 dilution, and cells were incubated for 2 hours. Percent inhibition was determined by the following formula: 100−(anti-RON antibody treated-baseline)/(control huIgG treated-baseline)*100. Results on inhibition of MSP-induced HPAF-II cell migration by anti-RON antibodies, sh29B06-78 and sh07F01-62, are summarized in Table 26 and FIG. 16.

TABLE 26

| AB concentration | sh29B06-78 | | sh07F01-62 | |
|---|---|---|---|---|
| ng/ml | AVG | Std DEV | AVG | Std DEV |
| 1000.00 | 94.82 | 3.34 | 98.96 | 3.79 |
| 200.00 | 90.67 | 2.37 | 97.80 | 1.12 |
| 40.00 | 59.85 | 12.50 | 67.18 | 7.67 |
| 8.00 | 59.71 | 2.87 | 37.22 | 4.16 |
| 1.60 | 63.95 | 20.15 | 38.91 | 13.79 |
| 0.32 | 42.03 | 39.88 | 43.27 | 5.76 |
| 0.06 | 60.37 | 11.92 | 34.40 | 2.31 |

The results in Table 26 demonstrate that humanized anti-RON antibodies, sh29B06-78 and sh07F01-62, potently inhibit MSP-induced cell migration in HPAF-II pancreatic cancer cell lines.

Example 18

Inhibition of MSP-Induced Cell Invasion

Humanized antibodies sh29B06-78 and shO7F01-62 as produced in Example 14 were tested for their ability to inhibit MSP-induced cell invasion. HPAF-II pancreatic cancer cells were trypsinized, counted, and placed at a concentration of 50,000/well in 45 μl of 10% FBS/MEM in the upper chamber of a BD 96-well BD BIOCOAT™ MATRIGEL™ invasion FLUOROBLOK™ plate (Becton Dickinson). Antibodies were added at a concentration of 30 μg/ml and cells were incubated for 2 hours. The bottom chamber contained 10% FBS MEM (2000 and 1 nM MSP, and cells were incubated for 24 hours. The number of cells that underwent invasion through the membrane was determined by the addition of Calcien Dye at 4 μg/ml final concentration to the bottom chamber, followed by a one-hour incubation. Fluorescence intensity was measured using a WALLAC 1420 VICTOR™ instrument (Perkin Elmer). Results on inhibition of MSP-induced HPAFII cell invasion by anti-RON antibodies are summarized in FIG. 17.

Figure 17:
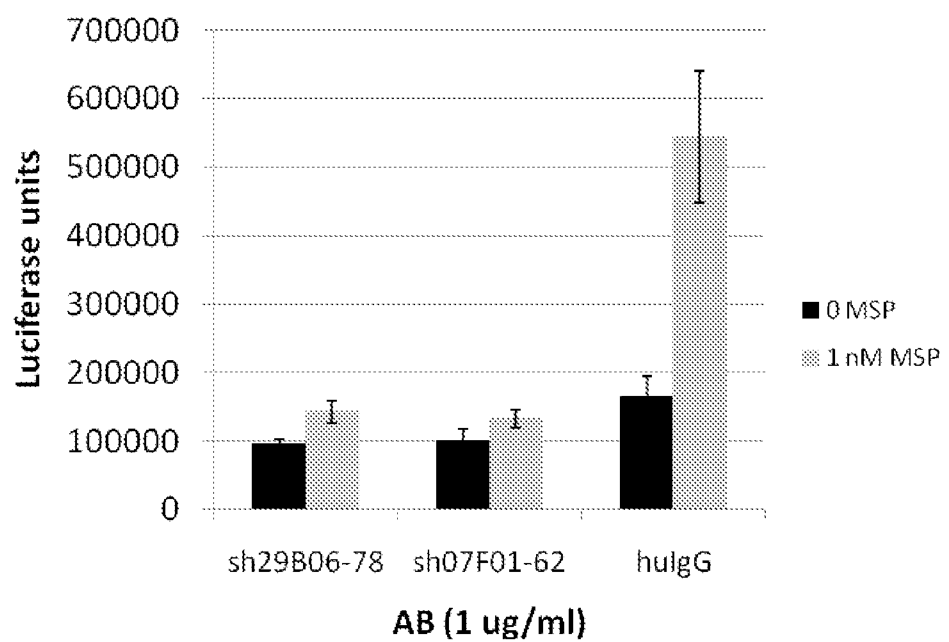
FIG. 17 is a histogram summarizing results from an experiment measuring inhibition of MSP induced HPAF-II cell invasion by anti-RON antibodies Sh29B06-78 and Sh07F01-62 and an IgG negative control (human IgG) at 0 and 1 nM MSP.

The results in FIG. 17 demonstrate that humanized anti-RON antibodies sh29B06-78 and sh07F01-6 potently inhibit MSP-dependent cell invasion in HPAF-II pancreatic cancer cell line.

Example 19

Inhibition of Growth of NCI-H358 Lung Xenograft Tumor Model

Inhibition of tumor growth by the humanized anti-RON antibodies was tested in an NCI-H358 lung xenograft model.

Figure 18:
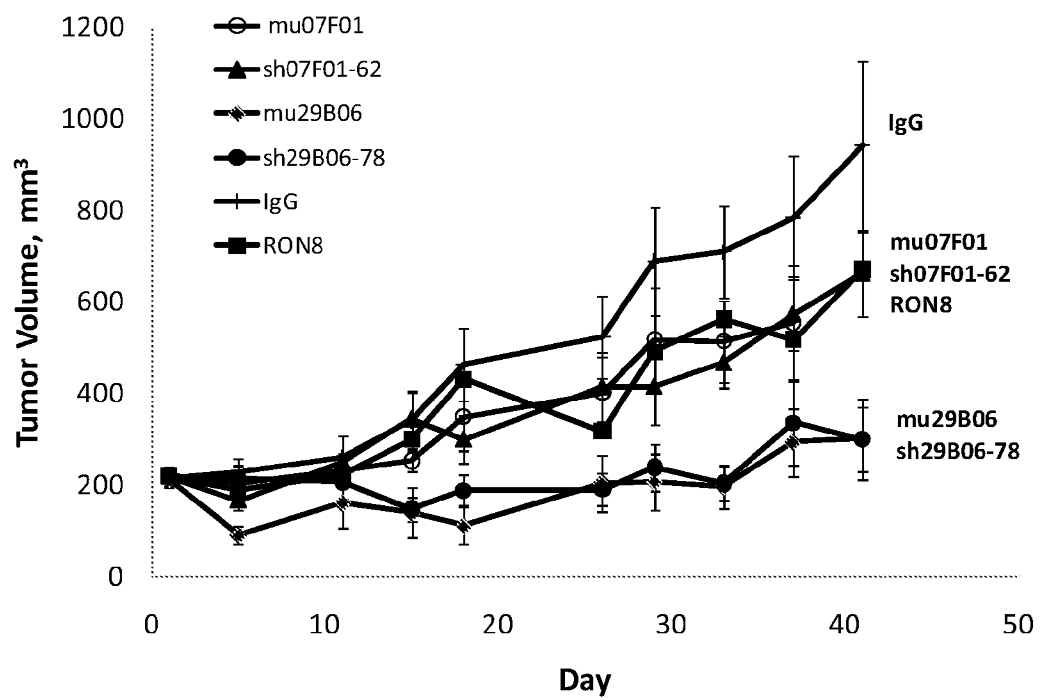
FIG. 18 is a graph summarizing data on inhibition of growth of an NCI-H358 xenograft tumor model by anti-RON antibodies mu07F01 (○), Sh07F01-62 (▲), mu29B06 (♦), RON8 (■), and Sh29B06-78 (●), and a human IgG control (+).

The NCI-H358 cells (ATCC) were grown in culture at 37° C. in an atmosphere containing 5% $CO_2$, using RMPI medium (Invitrogen) containing 10% FBS. Cells were inoculated subcutaneously into the flank of 8-week old female CB.17 SCID mice (Taconic Labs) with $5\times10^6$ cells per mouse in 50% matrigel (Becton Dickinson). Tumor measurements were taken twice weekly using vernier calipers. When tumors reached approximately 150 $mm^3$, the mice were randomized into six groups of ten mice each. Each group received one of the following treatments: human IgG (huIgG) control, mu29B06, sh29B06-78, mu07F01, sh07F01-62 and RON8. Treatment was administered by intra-peritoneal injection two times per week at 10 mg/kg for seven weeks. Treatment was well-tolerated, with no significant loss in body weight. Tumor growth inhibition is expressed as percent inhibition (baseline subtracted) to the huIgG control and statistical analysis was conducted using ANOVA. Results for tumor growth inhibition on day 41 in the NCI-H358 model are shown in FIG. 18 and Table 27.

TABLE 27

| Treatment | TGI % | ANOVA (compared to huIgG) |
|---|---|---|
| mu29B06 | 88.93 | P < 0.01 |
| sh29B06-78 | 89.02 | P < 0.01 |
| mu07F01 | 34.15 | P > 0.05 |
| sh07F01-62 | 39.05 | P > 0.05 |
| RON8 | 37.99 | P > 0.05 |

Anti-RON antibody treatments resulted in tumor growth inhibition compared to huIgG control. Specifically, mu29B06 antibody treatment resulted in tumor growth inhibition of 89% (P<0.01); sh29B06-78 antibody treatment resulted in tumor growth inhibition of 89% (P<0.01); mu07F01 antibody treatment resulted in tumor growth inhibition of 34% (P>0.05); sh07F01-62 antibody treatment resulted in tumor growth inhibition of 39% (P>0.05); and RON8 antibody treatment resulted in tumor growth inhibition of 38% (P>0.05). These results demonstrate that sh29B06-78 and mu29B06 inhibit tumor growth in a NCI-H358 xenograft model (P<0.01), whereas the mu07F01, sh07F01-62, and RON8 antibodies did not inhibit tumor growth in this model (P>0.05, which is not statically significant).

Example 20

RON Receptor Degradation

Western blots were performed to determine total levels of RON receptor at the end of treatment. Four tumor samples from each of the treatment groups were weighed, lysed in RIPA buffer (Boston Bioproducts), 1 mM EDTA Bioproducts), 1 mM Sodium OrthoVandadate (Sigma), 1× protease inhibitor (Sigma) and 1× Phosphatase Inhibitor I and II (Sigma). The samples were homogenized using a hand-held electric homogenizer and incubated for 10 minutes on ice. Samples are spun down at 11,000 RPM for 30 minutes at 4° C. Supernatants were collected and protein concentrations were determined using Pierce BCA™ assay kit according to the manufacturers protocol. The C-20 (Santa Cruz) antibody was used to detect total RON protein. β-tubulin (Cell Signaling Technologies) was blotted as loading control. The Western blots were blocked for one hour in 5% Milk in 1×TBST (TBS-0.1% TWEEN) (Sigma), followed by primary antibody incubation over night at 4° C. in 5% BSA 1×TBST at 1:1000 for both antibodies. Western blots were washed three times with 1×TBST, incubated with anti-rabbit HRP conjugated secondary antibody (Cell Signaling Technologies), for one hour at room temperature. Western blots were washed three times with 1×TBST and then developed using Dura Signal (Pierce).

Figure 19:
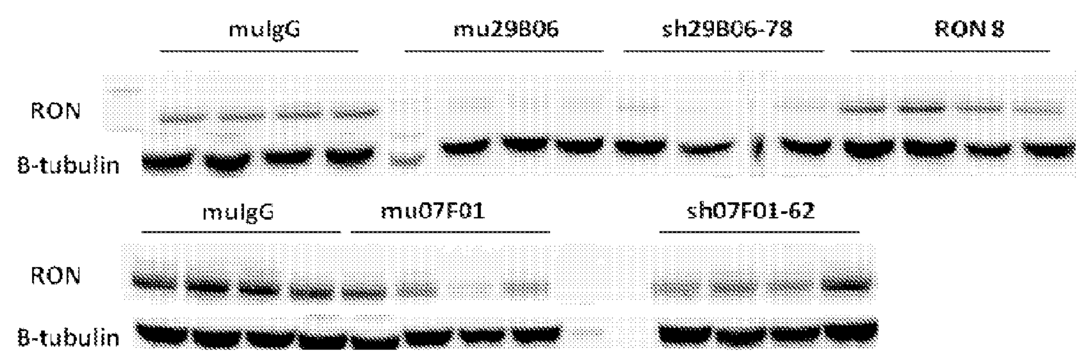
FIG. 19 depicts Western blots summarizing results from an experiment measuring RON receptor degradation by anti-RON antibodies mu07F01, Sh07F01-62, mu29B06, RON8, and Sh29B06-78.

The results in FIG. 19 demonstrate RON receptor degradation in the mu29B06 and sh29B06-78 treated samples and to a lesser extent in the mu07F01 and sh07F01-62 treated samples. RON receptor degradation was not observed in the RON8 treated samples.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. An isolated antibody that binds human RON (Recepteur d'Origine Nantais), comprising an immunoglobulin heavy chain variable region comprising a $CDR_{H1}$ comprising the amino acid sequence of SEQ ID NO: 45; a $CDR_{H2}$ comprising the amino acid sequence of SEQ ID NO: 46; and a $CDR_{H3}$ comprising the amino acid sequence of SEQ ID NO: 47; and an immunoglobulin light chain variable region comprising a $CDR_{L1}$ comprising the amino acid sequence of SEQ ID NO: 48, a $CDR_{L2}$ comprising the amino acid sequence of SEQ ID NO: 49, and a $CDR_{L3}$ comprising the amino acid sequence of SEQ ID NO: 50.

2. The antibody of claim 1, wherein the CDR sequences are interposed between humanized framework sequences.

3. An isolated antibody that binds human RON (Recepteur d'Origine Nantais) comprising an immunoglobulin heavy chain variable region comprising the amino acid sequence of SEQ ID NO: 147 and an immunoglobulin light chain variable region comprising the amino acid sequence of SEQ ID NO: 149.

4. An isolated antibody that binds human RON (Recepteur d'Origine Nantais) comprising an immunoglobulin heavy chain comprising the amino acid sequence of SEQ ID NO: 176 and an immunoglobulin light chain comprising the amino acid sequence of SEQ ID NO: 178.

5. The antibody of claim 1, wherein the antibody binds human RON with a $K_D$ of 900 pM or lower as measured by surface plasmon resonance.

6. The antibody of claim 5, wherein the antibody binds human RON with a $K_D$ of 500 pM or lower as measured by surface plasmon resonance.

7. The antibody of claim 6, wherein the antibody binds human RON with a $K_D$ of 250 pM or lower as measured by surface plasmon resonance.

8. The antibody of claim 1, wherein the CDR sequences are interposed between human framework sequences.

9. An isolated antibody that binds human RON (Recepteur d'Origine Nantais), comprising an immunoglobulin heavy chain variable region comprising a $CDR_{H1}$ comprising the amino acid sequence of SEQ ID NO: 126; a $CDR_{H2}$ comprising the amino acid sequence of SEQ ID NO: 46; and a $CDR_{H3}$ comprising the amino acid sequence of SEQ ID NO: 47; and an immunoglobulin light chain variable region comprising a $CDR_{L1}$ comprising the amino acid sequence of SEQ ID NO: 48, a $CDR_{L2}$ comprising the amino acid sequence of SEQ ID NO: 49, and a $CDR_{L3}$ comprising the amino acid sequence of SEQ ID NO: 50.

10. The antibody of claim 9, wherein the CDR sequences are interposed between humanized framework sequences.

11. The antibody of claim 9, wherein the CDR sequences are interposed between human framework sequences.

12. The antibody of claim 9, wherein the antibody binds human RON with a $K_D$ of 900 pM or lower as measured by surface plasmon resonance.

13. The antibody of claim 12, wherein the antibody binds human RON with a $K_D$ of 500 pM or lower as measured by surface plasmon resonance.

14. The antibody of claim 13, wherein the antibody binds human RON with a $K_D$ of 250 pM or lower as measured by surface plasmon resonance.

* * * * *